(12) United States Patent
Kong et al.

(10) Patent No.: US 7,253,306 B2
(45) Date of Patent: Aug. 7, 2007

(54) PHARMACEUTICAL DRUG CANDIDATES AND METHODS FOR PREPARATION THEREOF

(75) Inventors: Xianqi Kong, Dollard-des-Ormeaux (CA); David Migneault, Laval (CA); Xinfu Wu, Laval (CA)

(73) Assignee: Neurochem (International) Limited, Lausanne (CH)

( * ) Notice: Subject to any disclaimer, the term of this patent is extended or adjusted under 35 U.S.C. 154(b) by 249 days.

(21) Appl. No.: 10/871,543

(22) Filed: Jun. 18, 2004

(65) Prior Publication Data

US 2005/0143462 A1    Jun. 30, 2005

Related U.S. Application Data

(60) Provisional application No. 60/482,058, filed on Jun. 23, 2003, provisional application No. 60/480,906, filed on Jun. 23, 2003, provisional application No. 60/512,135, filed on Oct. 17, 2003, provisional application No. 60/512,047, filed on Oct. 17, 2003.

(51) Int. Cl.
*C07C 309/00* (2006.01)

(52) U.S. Cl. ......................................... 562/58; 562/101

(58) Field of Classification Search ...................... None
See application file for complete search history.

(56) References Cited

U.S. PATENT DOCUMENTS

| | | | |
|---|---|---|---|
| 4,085,134 A | | 4/1978 | Redmore et al. |
| 5,972,328 A | * | 10/1999 | Kisilevsky et al. ...... 424/78.31 |
| 6,562,836 B1 | * | 5/2003 | Szarek et al. ................ 514/307 |

FOREIGN PATENT DOCUMENTS

| | | | |
|---|---|---|---|
| CN | 1442405 A | * | 9/2003 |
| CN | 1200929 C | | 11/2005 |
| EP | 0 293 672 A1 | | 12/1988 |
| EP | 0 293 672 B1 | | 10/1991 |
| EP | 0 860 519 A1 | | 8/1998 |
| ES | 307776 | * | 1/1965 |
| FR | 1568065 | * | 5/1969 |
| GB | 764 340 A | | 12/1956 |
| GB | 1 319 841 A | | 6/1973 |
| WO | WO 96/28187 | | 9/1996 |
| WO | WO 99/40909 | | 8/1999 |
| WO | WO 00/64420 | | 11/2000 |

OTHER PUBLICATIONS

Science Lab, Science Lab.com, 1987,www.sciencelab .com/page/S/PVAR/10423/SLP4327.*
AcrosOrganics AcrosOrganics w/MSDS , 1996 , www.chemexper.com/index.shtml?main=http://www.chemexper.com/search/cas/3687-18.1.*
Allen, CFH et al. "Sultones as Agents for Derivatizing Aliphatic Amines in Qualitative Organic Analysis" *Anal. Chem.* 37(1): 156-158 (1965).
Helberger et al. *Justus Liebigs Ann. Chem.* 586: 158-63 (1954); abs. from Beilstein Database, Database accession No. Reaction ID 69948.
King, JF et al. *Can J. Chem.* 61: 235-43 (1983); abs. from Beilstein Database, Database accession No. BRN 5931024.
Helferich B et al. *Justus Liebigs Ann. Chem.* 37-40 (1971); abs. from Beilstein Database, Database accession No. BRN 2434022.
Erman, WF et al. "Synthesis and Facile Cleavage of Five-membered Ring Sultams" *J. Org. Chem.* 26: 4841-50 (1961).
International Search Report and Written Opinion from PCT/IB2004/002563.

* cited by examiner

*Primary Examiner*—Paul A. Zucker
(74) *Attorney, Agent, or Firm*—Lahive & Cockfield LLP

(57) ABSTRACT

The present invention is directed to methods of preparation of sulfonate derivatized compounds, e.g., 3-amino-1-propanesulfonic acid and 1,3-propanedisulfonic acid disodium salt with increased purity, with reduced potential for toxic by-products, and that are pharmaceutically useful, e.g., for the treatment of amyloidosis.

17 Claims, No Drawings

PHARMACEUTICAL DRUG CANDIDATES AND METHODS FOR PREPARATION THEREOF

RELATED APPLICATIONS

This application claims priority to U.S. provisional patent application No. 60/482,058, filed Jun. 23, 2003, U.S. provisional patent application No. 60/512,135, filed Oct. 17, 2003, both entitled Synthetic Process for Preparing Compounds for Treating Amyloidosis, U.S. provisional patent application No. 60/480,906, filed Jun. 23, 2003, and U.S. provisional patent application No. 60/512,047, filed Oct. 17, 2003.

This application is related to U.S. provisional patent application No. 60/480,984, filed Jun. 23, 2003, U.S. provisional patent application No. 60/512,116, filed Oct. 17, 2003, both entitled Pharmaceutical Formulations of Amyloid-Inhibiting Compounds, and U.S. application Ser. No. 10/871,549, filed Jun. 18, 2004, entitled Pharmaceutical Formulations of Amyloid-Inhibiting Compounds. This application is related to U.S. provisional application No. 60/436,379, filed Dec. 24, 2002, entitled Combination Therapy for the Treatment of Alzheimer's Disease, U.S. provisional application 60/482,214, filed Jun. 23, 2003, U.S. utility patent application Ser. No. 10/746,138, filed Dec. 24, 2003, and International patent application No. PCT/CA2003/002011, entitled Therapeutic Formulations for the Treatment of Beta-Amyloid Related Diseases. This application is also related to U.S. provisional patent application No. 60/480,918, filed Jun. 23, 2003, U.S. provisional application 60/512,017, filed Oct. 17, 2003, and U.S. patent application Ser. No. 10/871,613 filed Jun. 18, 2004, entitled Methods for Treating Protein Aggregation Disorders. This application is also related to U.S. application Ser. No. 10/871,514 filed Jun. 18, 2004, and U.S. application Ser. No. 10/871,365 filed Jun. 18, 2004, all entitled Methods and Compositions for Treating Amyloid-Related Diseases; and U.S. provisional patent application No. 60/480,928, also filed 23 Jun. 2003, U.S. provisional patent application No. 60/512,018, filed Oct. 17, 2003, and U.S. application Ser. No. 10/871,512 filed Jun. 18, 2004, all entitled Methods and Compositions for the Treatment of Amyloid- and Epileptogenesis-Associated Diseases; This application is also related to Method for Treating Amyloidosis, U.S. patent application Ser. No. 08/463,548, now U.S. Pat. No. 5,972,328.

The entire contents of each of the foregoing patent applications and patents are expressly incorporated by reference in their entirety including, without limitation, the specification, claims, and abstract, as well as any figures, tables, or drawings thereof.

BACKGROUND OF THE INVENTION

The compound, 1,3-propanedisulfonic acid, disodium salt, is a compound known in the literature since the 1930's (e.g., see G. C. H. Stone, J. Am. Chem. Soc., 58, 488 (1936)). The synthesis of 1,3-propanedisulfonic acid disodium salt was based on the reaction of 1,3-dibromopropane with sodium sulfite in aqueous media, as indicated in the following scheme:

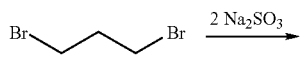

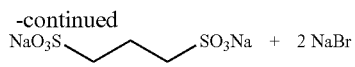

However, a number of significant problems exist with the known synthetic strategy that make this method of preparation of 1,3-propanedisulfonic acid disodium salt non-optimal, e.g., non-efficient, for large scale preparation of pharmaceutically acceptable compositions. For example, the original synthesis (by Stone) involved a work-up procedure using salts of lead, barium, and silver to remove inorganic materials followed by repeated precipitation, resulting in a very low yield.

In particular, the potential for the production of by-products that would be considered toxic to animals, e.g., humans, such as alkylating agents, exists. In addition to the starting materials and the reaction product, there are several related possible organic by-products, as well as other inorganic compounds (sulfate and sulfite). The following scheme outlines all the possible compounds in the reaction mixture.

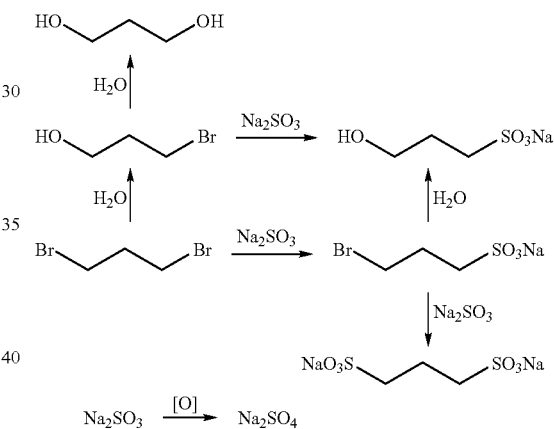

An additional problem with the existing methodology involves the large amount of ethanol required for purification of the product. The reaction produces two-mole-equivalent of NaBr for one mole of 1,3-propanedisulfonic acid disodium salt, creating an unfavorable product mass balance, i.e., creating significant waste. In order to remove the large amount of sodium bromide, ethanol is employed to precipitate the product, leaving the sodium bromide in the supernatant.

There are two direct effects of using a large volume of ethanol. The first is the cost of the solvent, and the second is the throughput reduction (limited by the reaction vessel capacity) that in turn increases the cost of the entire process. Furthermore, due to the large volume of ethanol used in the purification, the batch size is relatively small. As a result the throughput of production is reduced, and consequently the actual cost of the final product increases.

Additionally, the known synthesis of 3-amino-1-propanesulfonic acid is based on the reaction of 3-chloro-1-propylamine (3-CPA) hydrochloride with sodium sulfite in aqueous solution.

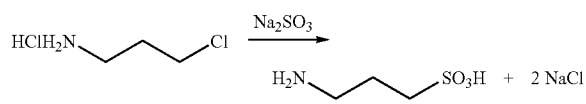

This reaction produces two-mole-equivalents of NaCl for one mole of the product, creating an unfavorable product mass balance, i.e., creating significant waste. Moreover, in the manufacturing process, concentrated HCl is required to precipitate the sodium chloride, followed by ethanol precipitation of the product from aqueous solution.

Again, the potential for the production of by-products that would be considered toxic to animals, e.g., humans, such as alkylating agents, exists. For example, the starting material, 3-CPA, may persist in the target product; even at a low level, this could cause concern in the administration of the compound in a pharmaceutical composition.

Application to Amyloidosis

Compounds such as 3-amino-1-propanesulfonic acid and 1,3-propanedisulfonic acid disodium salt have recently been discovered to be useful for the treatment of amyloidosis. Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Amyloid-related diseases can either be restricted to one organ or spread to several organs. The first instance is referred to as "localized amyloidosis" while the second is referred to as "systemic amyloidosis."

Some amyloid diseases can be idiopathic, but most of these diseases appear as a complication of a previously existing disorder. For example, primary amyloidosis (AL amyloid) can appear without any other pathology or can follow plasma cell dyscrasia or multiple myeloma.

Secondary amyloidosis is usually seen associated with chronic infection (such as tuberculosis) or chronic inflammation (such as rheumatoid arthritis). A familial form of secondary amyloidosis is also seen in other types of familial amyloidosis, e.g., Familial Mediterranean Fever (FMF). This familial type of amyloidosis is genetically inherited and is found in specific population groups. In both primary and secondary amyloidosis, deposits are found in several organs and are thus considered systemic amyloid diseases.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the amyloid plaques found in the parenchyma and the blood vessel is formed by the deposition of fibrillar Aβ amyloid protein. Other diseases such as adult-onset diabetes (type II diabetes) are characterized by the localized accumulation of amyloid fibrils in the pancreas.

Once these amyloids have formed, there is no known, widely accepted therapy or treatment which significantly dissolves amyloid deposits in situ, prevents further amyloid deposition or prevents the initiation of amyloid deposition.

Each amyloidogenic protein has the ability to undergo a conformational change and to organize into β-sheets and form insoluble fibrils which may be deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, show similarities such as regions with the ability to bind to the glycosaminoglycan (GAG) portion of proteoglycan (referred to as the GAG binding site) as well as other regions which promote β-sheet formation. Proteoglycans are macromolecules of various sizes and structures that are districuted almost everywhere in the body. They can be found in the intracellular compartment, on the surface of cells, and as part of the extracellular matrix. The basic structure of all proteoglycans is comprised of a core protein and at least one, but frequently more, polysaccharide chains (GAGs) attached to the core protein. Many different GAGs have been discovered including chondroitin sulfate, dermatan sulfate, keratan sulfate, heparin, and hyaluronan.

In specific cases, amyloid fibrils, once deposited, can become toxic to the surrounding cells. For example, the Aβ fibrils organized as senile plaques have been shown to be associated with dead neuronal cells, dystrophic neurites, astrocytosis, and microgliosis in patients with Alzheimer's disease. When tested in vitro, oligomeric (soluble) as well as fibrillar Aβ peptide was shown to be capable of triggering an activation process of microglia (brain macrophages), which would explain the presence of microgliosis and brain inflammation found in the brain of patients with Alzheimer's disease. Both oligomeric and fibrillar Aβ peptide can also induce neuronal cell death in vitro. See, e.g., M P Lambert, et al., *Proc. Natl. Acad. Sci. USA* 95, 6448-53 (1998).

In another type of amyloidosis seen in patients with type II diabetes, the amyloidogenic protein IAPP, when organized in oligomeric forms or in fibrils, has been shown to induce β-islet cell toxicity in vitro. Hence, appearance of IAPP fibrils in the pancreas of type II diabetic patients contributes to the loss of the β islet cells (Langerhans) and organ dysfunction which can lead to insulinemia.

Another type of amyloidosis is related to $\beta_2$ microglobulin and is found in long-term hemodialysis patients. Patients undergoing long term hemodialysis will develop $\beta_2$-microglobulin fibrils in the carpal tunnel and in the collagen rich tissues in several joints. This causes severe pains, joint stiffness and swelling.

Amyloidosis is also characteristic of Alzheimer's disease. Alzheimer's disease is a devastating disease of the brain that results in progressive memory loss leading to dementia, physical disability, and death over a relatively long period of time. With the aging populations in developed countries, the number of Alzheimer's patients is reaching epidemic proportions.

People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals (dystrophic neurites) and activated microglia (microgliosis and astrocytosis). A main constituent of these amyloid plaques is the amyloid-β peptide (Aβ), a 39-43 amino-acid protein that is produced through cleavage of the β-amyloid precursor protein (APP). Extensive research has been conducted on the relevance of Aβ deposits in Alzheimer's disease, see, e.g., Selkoe, *Trends in Cell Biology* 8, 447-453 (1998). Aβ naturally arises from the metabolic processing of the amyloid precursor protein ("APP") in the endoplasmic reticulum ("ER"), the Golgi apparatus, or the endosomal-lysosomal pathway, and most is normally secreted as a 40 ("Aβ1-40") or 42 ("Aβ1-42") amino acid peptide (Selkoe, *Annu. Rev. Cell Biol.* 10, 373-403 (1994)). A role for Aβ as a primary cause for Alzheimer's disease is supported by the presence of extracellular Aβ deposits in senile plaques of Alzheimer's disease, the increased production of Aβ in cells harboring mutant Alzheimer's disease associated genes, e.g., amyloid precursor protein, presenilin I and presenilin II; and the toxicity of extracellular soluble (oligomeric) or fibrillar Aβ to cells in culture. See, e.g., Gervais, *Eur. Biopharm. Review*, 40-42 (Autumn 2001); May, *DDT* 6, 459-62 (2001). Although symptomatic treatments exist for Alzheimer's disease, this disease cannot be prevented or cured at this time.

Alzheimer's disease is characterized by diffuse and neuritic plaques, cerebral angiopathy, and neurofibrillary tangles. Plaque and blood vessel amyloid is believed to be formed by the deposition of insoluble Aβ amyloid protein, which may be described as diffuse or fibrillary. Both soluble oligomeric Aβ and fibrillar Aβ are also believed to be neurotoxic and inflammatory.

Another type of amyloidosis is cerebral amyloid angiopathy (CAA). CAA is the specific deposition of amyloid β fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)).

Presently available therapies for treatment of β-amyloid diseases are almost entirely symptomatic, providing only temporary or partial clinical benefit. Although some pharmaceutical agents have been described that offer partial symptomatic relief, no comprehensive pharmacological therapy is currently available for the prevention or treatment of, for example, Alzheimer's disease.

SUMMARY OF THE INVENTION

A need exists for novel methods of preparation of sulfonate derivatized compounds, e.g., 3-amino-1-propanesulfonic acid and 1,3-propanedisulfonic acid disodium salt with increased purity, with reduced potential for toxic by-products, that are pharmaceutically useful, e.g., for the treatment of amyloidosis, and at reasonable cost.

Accordingly, in one aspect, the invention is directed to a method of large scale preparation of a sulfonate derivatized compound comprising opening a sultone ring with a nucleophile, such that a sulfonate derivatized compound is produced in large scale.

In another aspect, the invention pertains to a method of preparation of a pharmaceutically-useful sulfonate derivatized compound comprising opening a sultone ring with a nucleophile, such that a pharmaceutically-useful sulfonate derivatized compound is produced.

Another aspect of the invention is a method of preparation of a purity-enhanced sulfonate derivatized pharmaceutical drug candidate comprising opening a sultone ring with a nucleophile, such that a purity-enhanced sulfonate derivatized pharmaceutical drug candidate is produced.

An additional aspect of the invention is directed to a method of preparation of a sulfonate derivatized compound comprising opening a sultone ring with a nucleophile, such that a sulfonate derivatized compound is produced, wherein the sulfonate derivatized compound is selected from the group consisting of 1,3-propanedisulfonic acid disodium salt, 1,4-butanedisulfonic acid disodium salt, 3-amino-1-propanesulfonic acid, 3-amino-1-propanesulfonic acid, sodium salt, 3-(dimethylamino)-1-propanesulfonic acid, 3-(1,2,3,6-tetrahydropyridinyl)-1-propanesulfonic acid, 3-(1,2,3,4-tetrahydroisoquinolinyl)-1-propanesulfonic acid, 3-(4-cyano-4-phenylpiperidin-1-yl)-1-propanesulfonic acid, 3-[4-(4-fluorophenyl)-1,2,3,6-tetrahydropyridin-1-yl]-1-propanesulfonic acid, 3-[4-(4-bromophenyl)-4-hydroxypiperidin-1-yl]-1-propanesulfonic acid, 3-[4-(4-chlorophenyl)-4-hydroxypiperidin-1-yl]-1-propanesulfonic acid, 3-(4-acetyl-4-phenylpiperidin-1-yl)-1-propanesulfonic acid, 3-[4-(4-chlorophenyl)-1,2,3,6-tetrahydropyridin-1-yl]-1-propanesulfonic acid, 3-tryptamino-1-propanesulfonic acid, 3-(1,2,3,4-tetrahydro-naphthylamino)-1-propanesulfonic acid, 3-(1-adamantylamino)-1-propanesulfonic acid, 3-(2-norbornylamino)-1-propanesulfonic acid, 3-(2-admantylamino)-1-propanesulfonic acid, 3-(4-(hydroxy-2-pentyl)amino)-1-propanesulfonic acid, and 3-(t-butylamino)-1-propanesulfonic acid.

In another aspect, the invention pertains to a method of preparation of a sulfonate derivatized compound comprising opening a sultone ring with a nucleophile, such that the sulfonate derivatized compound is produced, wherein the sulfonate derivatized compound is selected from the group consisting of the compounds listed in Table 2 or Table 3.

In yet another aspect, the invention pertains to a method of preparation of a sulfonate derivatized compound comprising opening a sultone ring with a nucleophile, such that the sulfonate derivatized compound is produced, wherein the sulfonate derivatized compound is 3-amino-1-propanesulfonic acid.

An additional aspect of the invention is directed to a method of preparation of a sulfonate derivatized compound comprising opening a sultone ring with a nucleophile, such that the sulfonate derivatized compound is produced, wherein the sulfonate derivatized compound is 1,3-propanedisulfonic acid.

In yet another aspect, the invention pertains to a method of preparation of a sulfonate derivatized compound comprising opening a sultone ring with a nucleophile, such that the sulfonate derivatized compound is produced, wherein the sulfonate derivatized compound is 3-(dimethylamino)-1-propanesulfonic acid.

In another aspect, the invention pertains to a method of preparation of a sulfonate derivatized compound comprising opening a sultone ring with a nucleophile, such that the sulfonate derivatized compound is produced, wherein the sulfonate derivatized compound is 3-(t-butyl)amino-1-propanesulfonic acid.

In yet another aspect, the invention is a method of preparation of a sulfonate derivatized compound comprising opening a sultone ring with a nucleophile, such that the sulfonate derivatized compound is produced, wherein the sulfonate derivatized compound is 3-(1-adamantylamino)-1-propanesulfonic acid.

In an additional aspect, the invention pertains to a method of preparation of a sulfonate derivatized compound comprising opening a sultone ring with a nucleophile, such that the sulfonate derivatized compound is produced, wherein the sulfonate derivatized compound is 3-(2-adamantylamino)-1-propanesulfonic acid.

Another aspect of the present invention is directed to a method of preparation of a sulfonate derivatized compound comprising opening a sultone ring with a nucleophile, such that the sulfonate derivatized compound is produced, wherein the sulfonate derivatized compound is 3-nonylamino-1-propanesulfonic acid.

Yet another aspect of the invention is directed to a method of preparation of a pharmaceutical composition comprising a pharmaceutical drug candidate and a pharmaceutically acceptable carrier, the method comprising opening a sultone ring with a nucleophile, resulting in a pharmaceutical drug candidate; and combining the pharmaceutical drug candidate with a pharmaceutically acceptable carrier, forming a pharmaceutical composition.

In an additional aspect, the present invention pertains to a method of preparation of a pharmaceutical composition comprising a pharmaceutical drug candidate useful for inhibiting amyloid deposition in a subject, and a pharmaceutically acceptable carrier, the method comprising opening a sultone ring with a nucleophile, resulting in a pharmaceutical drug candidate; and combining the pharmaceutical drug candidate with a pharmaceutically acceptable carrier, forming a pharmaceutical composition.

In another aspect, the invention is a method of preparation of a pharmaceutical composition comprising a pharmaceutical drug candidate useful for treating amyloidosis in a subject, and a pharmaceutically acceptable carrier, the method comprising opening a sultone ring with a nucleophile, resulting in a pharmaceutical drug candidate; and combining the pharmaceutical drug candidate with a pharmaceutically acceptable carrier, forming a pharmaceutical composition.

In yet another aspect, the invention is directed to a method of preparation of a pharmaceutical composition comprising a pharmaceutical drug candidate useful for treating or preventing an amyloid-related disease in a subject, and a pharmaceutically acceptable carrier, the method comprising opening a sultone ring with a nucleophile, resulting in a pharmaceutical drug candidate; and combining the pharmaceutical drug candidate with a pharmaceutically acceptable carrier, forming a pharmaceutical composition.

An additional aspect of the invention pertains to a method of preparation of a 1,3-propanedisulfonic acid compound comprising opening a sultone ring with a nucleophile, wherein said nucleophile is a sulfite anion, such that a 1,3-propanedisulfonic acid compound is produced.

Another aspect of the invention is directed to a method of preparation of a 3-amino-1-propanesulfonic acid compound comprising opening a sultone ring with a nucleophile, wherein said nucleophile is ammonia, such that a 3-amino-1-propanesulfonic acid compound is produced.

In another aspect, the invention pertains to a method of preparation of a 3-amino-1-propanesulfonic acid compound comprising opening a sultone with a nucleophile, wherein said nucleophile is azide, and reducing the azide to an amino group, such that a 3-amino-1-propanesulfonic acid compound is produced.

In yet another aspect, the present invention is a method of preparation of a 3-amino-1-propanesulfonic acid compound comprising opening a sultone with a nucleophile, wherein said nucleophile is benzylamine, and debenzylating the opened sultone, such that a 3-amino-1-propanesulfonic acid compound is produced.

Another aspect of the invention is a compound, e.g., a 1,3-propanedisulfonic acid compound or a 3-amino-1-propanesulfonic acid compound, produced by the methods of the invention described herein.

Yet another aspect of the invention is directed to a sulfonate derivatized compound prepared by the method comprising opening a sultone ring with a nucleophile, resulting in a sulfonate derivatized compound, wherein said nucleophile is a sulfite, such that a sulfonate derivatized compound is produced.

An additional aspect of the invention pertains to a sulfonate derivatized compound prepared by the method comprising opening a sultone ring with a nucleophile, resulting in a sulfonate derivatized compound, wherein said nucleophile is an amine, such that an amino sulfonate derivatized compound is produced.

In another aspect, the invention is directed to a method of preparation of a pharmaceutical composition comprising a pharmaceutical drug candidate (PDC) useful for inhibiting amyloid deposition in a subject, and a pharmaceutically acceptable carrier, comprising: opening a sultone ring with a nucleophile, resulting in a pre-selected pharmaceutical drug candidate, wherein the PDC is pre-selected for its ability to inhibit amyloid deposition in a subject; and combining the pharmaceutical drug candidate with a pharmaceutically acceptable carrier, forming a pharmaceutical composition. In certain embodiments, the method comprises the step of purifying the pharmaceutical drug candidate.

In yet another aspect, the invention pertains to a method of preparation of a pharmaceutical composition comprising a pharmaceutical drug candidate useful for treating amyloidosis in a subject, and a pharmaceutically acceptable carrier, comprising: opening a sultone ring with a nucleophile, resulting in a pharmaceutical drug candidate, wherein the PDC is pre-selected for its ability to treat amyloidosis in a subject; and combining the pharmaceutical drug candidate with a pharmaceutically acceptable carrier, forming a pharmaceutical composition. In certain embodiments, the method comprises the step of purifying the pharmaceutical drug candidate.

Another aspect of the invention is a method of preparation of a pharmaceutical composition comprising a pharmaceutical drug candidate useful for treating or preventing an amyloid-related disease in a subject, and a pharmaceutically acceptable carrier, comprising: opening a sultone ring with a nucleophile, resulting in a pharmaceutical drug candidate, wherein the PDC is pre-selected for its ability to treat or prevent an amyloid-related disease in a subject; and combining the pharmaceutical drug candidate with a pharmaceutically acceptable carrier, forming a pharmaceutical composition. In certain embodiments, the method comprises the step of purifying the pharmaceutical drug candidate.

Another aspect of the invention is a method of enhanced throughput production of a sulfonate derivatized compound comprising opening a sultone ring with a nucleophile, such that enhanced throughput of a sulfonate derivatized compound occurs.

Another aspect of the invention is directed to a purity-enhanced pharmaceutical drug candidate comprising a sulfonate derivatized compound which is significantly free of by-products.

In yet another aspect, the invention is a pharmaceutically-useful pharmaceutical drug candidate comprising a sulfonate derivatized compound which is suitable for use in a pharmaceutical composition.

In another aspect, the invention is directed to a purity-enhanced pharmaceutical drug candidate comprising: 1,3-propanedisulfonic acid or a salt thereof, wherein the pharmaceutical drug candidate is free of bromide.

In another aspect, the invention is directed to a purity-enhanced pharmaceutical drug candidate comprising: 1,3-propanedisulfonic acid or a salt thereof, wherein the pharmaceutical drug candidate is free of sodium.

In yet another aspect, the invention is directed to a purity-enhanced pharmaceutical drug candidate comprising: 1,3-propanedisulfonic acid or a salt thereof, wherein the sulfate content is less than 1.4%.

In an additional aspect, the invention pertains to a purity-enhanced pharmaceutical drug candidate comprising: 1,3-propanedisulfonic acid or a salt thereof, wherein the pharmaceutical drug candidate is free of at least one of the by-products selected from the group consisting of 1,3-propanediol, 3-bromo-propan-1-ol, 1,3-dibromopropane, and 3-bromo-propanesulfonate.

Another aspect of the invention is directed to a purity-enhanced pharmaceutical drug candidate comprising: 3-amino-1-propanesulfonic acid or a salt thereof, wherein the pharmaceutical drug candidate is free of chloride.

An aspect embodiment of the invention pertains to a purity-enhanced pharmaceutical drug candidate comprising: 3-amino-1-propanesulfonic acid or a salt thereof, wherein the pharmaceutical drug candidate is free of sodium.

In another aspect, the invention is a purity-enhanced pharmaceutical drug candidate comprising: 3-amino-1-propanesulfonic acid or a salt thereof, wherein the pharmaceutical drug candidate is free of 3-CPA.

An additional aspect of the invention is directed to a pharmaceutical drug candidate comprising a sulfonate derivatized compound, which is greater than or equal to 95% pure and is fress of a bromide and free of chloride.

DETAILED DESCRIPTION OF THE INVENTION

This invention pertains to methods of preparation of sulfonate derivatized compounds, e.g., 3-amino-1-propanesulfonic acid and 1,3-propanedisulfonic acid disodium salt with increased purity, with reduced potential for toxic by-products, and that are pharmaceutically useful, e.g., for the treatment of amyloidosis.

It is envisioned that the methods of preparation of the present invention, i.e., synthetic strategies, are applicable to the preparation of a large number of commercially valuable compounds.

I. Methods of the Invention

Accordingly in one embodiment, the invention is directed to a method of large scale preparation of a sulfonate derivatized compound comprising opening a sultone ring with a nucleophile, such that a sulfonate derivatized compound is produced in large scale.

In one embodiment, the sultone ring opening reaction is represented by:

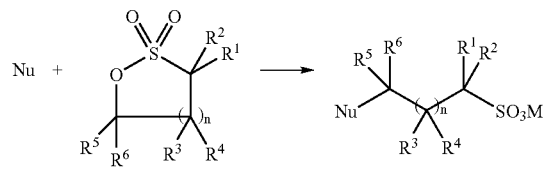

wherein n=1 to 5, e.g., 1 or 2; Nu is the nucleophile; M is a hydrogen or a salt-forming group; $R^1$, $R^2$, $R^3$, $R^4$, $R^5$, and $R^6$ are independently selected from any substituent that does not significantly interefere with the ability of the reaction to proceed, e.g., substituents noted herein, e.g., hydrogen, or a substituted or unsubstituted alkyl group. For example, in certain embodiments, substituents that would not be contemplated by the present application would be those substituents that would be more reactive than the sulfur of the sultone ring or those substituents, e.g., certain amines, which would result in polymerization of the starting material. In organic synthesis, sulfonate is often used as a leaving group.

In $SN_2$ reactions, a nucleophile can attack the carbon atom where a sulfonate group is covalently connected through the single-bounded oxygen atom. This reaction results in the displacement of the sulfonate group by the nucleophile. In the case of α,ω-alkane sultone, where the sulfonate has a cyclic structure having sulfur bounded to Cα and oxygen bounded to Cω, this reaction leads to the formation of a ω-substituted-α-alkanesulfonic acid derivative. Typical, commercially available sultones are 1,3-propane sultone and 1,4-butane sultone.

In a particular embodiment, the sultone ring opening reaction is represented by:

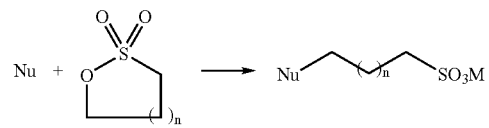

wherein n=1 or 2; Nu is the nucleophile; M is a hydrogen or a salt-forming group, e.g., sodium.

The language "sulfonate derivatized compound" includes any compound that contains a sulfonate group as a functional moiety that can be prepared by the methods of the present invention.

A "sulfonate group" as used herein is an —SO₃H or —SO₃X group bonded to a carbon atom, where X is a cationic group or an ester forming group. Similarly, a "sulfonic acid" compound has a —SO₃H group bonded to a carbon atom. A "sulfate" as used herein is a —OSO₃H or —OSO₃X group bonded to a carbon atom, where X is a cationic group or an ester group; and a "sulfuric acid" compound has a —OSO₃H group bonded to a carbon atom. According to the invention, a suitable cationic group may be a hydrogen atom or a salt-forming metal ion. In certain cases, the cationic group may actually be another group on the sulfonate derivatized compound that is positively charged at physiological pH, for example an amino group. Such compounds containing such a cationic group covalently bonded to the sulfonate derivatized compound itself may be referred to as an "inner salt" or a "zwitterion."

In a specific embodiment, when Nu is a sulfite anion, n is equal to 1, $R^1$, $R^2$, $R^3$, $R^4$, $R^5$, and $R^6$ are hydrogen, and M is sodium, the above reaction becomes the following:

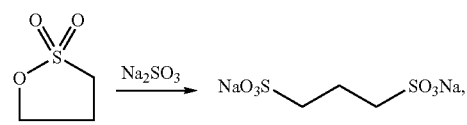

and 1,3-propanedisulfonic acid disodium salt is the product.

In another specific embodiment, when Nu is ammonia (either in organic solvent or in aqueous solution), n is equal to 1, $R^1$, $R^2$, $R^3$, $R^4$, $R^5$, and $R^6$ are hydrogen, and M is hydrogen, the above reaction becomes the following:

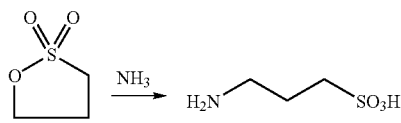

and 3-amino-1-propanesulfonic acid is the product.

The language "nucleophile (Nu)" is art-recognized and includes any chemical group having a reactive pair of electrons that is capable of participating in nucleophilic substitution, e.g., $S_N2$ type, ring opening of a sultone ring. For example, a nucleophile of the present invention includes but is not limited to an anionic nucleophile, such as a halide ($Cl^-$, $Br^-$, $I^-$), azide, nitrate, nitrile carbonate, hydroxide, cyanide, phosphate, phosphate, sulfide, sulfite, sulfate, carboxylate, phosphonate, sulfonate; a nitrogen-containing nucleophile, such as ammonia (or ammonium hydroxide), amine (primary, secondary, and tertiary), a natural or unnatural amino acid, aromatics (such as pyridine and its derivatives, pyrazine and its derivatives, triazine and its derivatives, pyrrole and its derivatives, pyrazole and its derivatives, piperidine and its derivatives, triazole and its derivatives, tetrazole), hydrazines, urea, thiourea, guanidine, amide, and urethane; an oxygen or a sulfur-containing nucleophile, such as an alcohol (alkoxide), phenol (phenoxide), thiol (alkyl and aryl sulfide). Particular examples of nucleophiles of the invention include, but are not limited to sodium sulfite, gaseous ammonia, ammonium hydroxide, dimethylamine, azide, benzyldimethylamine, 1,2,3,6-tetrahydropyridine, 1,2,3,6-tetrahydoisoquinoline, 4-cyano-4-phenylpiperidine, 4-(4-fluorophenyl)-1,2,3,6-tetrahydropyridine, 4-(4-bromophenyl)-4-piperidinol, 4-(4-chlorophenyl)-4-piperidinol, 4-acetyl-4-phenylpiperidine hydrochloride, 4-(4-chlorophenyl)-1,2,3,6-tetrahydropyridine, tryptamine, 1,2,3,4-tetrahydro-1-naphthylamine, 1-adamantanamine, 2-aminonorbornane, 2-aminoadamantane, 2-amino-1-pentanol, and tert-butylamine. In specific embodiments, the nucleophile is a sulfite anion. In another embodiment, phosphorus acid or its equivalent such as its esters may be used as a nucleophile (to produce phosphonoalkanesulfonic acid).

The language "large scale" as used in the language "large scale preparation" includes reactions which result in product in an amount, e.g., greater than 26 g, e.g., greater than 30 g, e.g., greater than 35 g, e.g., greater than 40 g, e.g., greater than 45 g, e.g., greater than 50 g, e.g., greater than 60 g, e.g., greater than 70 g, e.g., greater than 80 g, e.g., greater than 90 g, e.g., greater than 100 g, e.g., greater than 200 g, e.g., greater than 500 g, e.g., greater than 1 kg, e.g., greater than 2 kg, e.g., greater than 5 kg, e.g., greater than 10 kg, e.g., greater than 20 kg, e.g., greater than 40 kg, e.g., greater than 60 kg, and e.g., greater than 100 kg.

Pharmaceutical Drug Candidates

In one embodiment, the invention pertains to a method of preparation of a purity-enhanced sulfonate derivatized pharmaceutical drug candidate comprising opening a sultone ring with a nucleophile, such that a purity-enhanced sulfonate derivatized pharmaceutical drug candidate is produced.

The language "pharmaceutical drug candidate (PDC)" includes sulfonate derivatized compounds that are pharmaceutically useful or purity-enhanced, e.g., including, but not limited to the sulfonate derivatized compound prepared by the methods of the invention, and which are suitable for use in the treatment of disease e.g., disorders. In one embodiment, the PDC is useful for the treatment or prevention of amyloid-related disease. In a particular embodiment, the pharmaceutical drug candidate is useful in inhibiting amyloid deposition in a subject. In another particular embodiment, the pharmaceutical drug candidate is useful in treating amyloidosis in a subject. In another particular embodiment, the pharmaceutical drug candidate is useful in treating Alzheimer's disease, cerebral amyloid angiopathy, inclusion body myositis, macular degeneration, AA amyloidosis, AL amyloidosis, Down's syndrome, Mild Cognitive Impairment, type II diabetes, and hereditary cerebral hemorrhage. In another embodiment, the pharmaceutical drug candidate prevents or inhibits amyloid oligomerization or deposition, cellular toxicity or neurodegeneration.

The language "purity-enhanced" is used in reference to a final product of a sulfonate derivatized compound, e.g., a pharmaceutical drug candidate, i.e., derived from a crude or purified reaction mixture, e.g., including, but not limited to the sulfonate derivatized compounds produced by the methods of the invention, which is significantly free of by-products, e.g., toxic by-products (i.e., by-products that are side-products of the reaction or residual starting material that would be considered unsuitable for administration to a subject, e.g., a human, or preferentially omitted by a skilled artisan from a pharmaceutical composition prepared for administration to a subject). It should be noted that purity-enhanced compounds of the invention are not intended to be limited by scale of the reaction that produces the compounds.

The language "significantly free of" as used in the language "significantly free of by-products" characterizes the presence of by-products, e.g., in a final product, e.g., a pharmaceutically acceptable drug candidate, in an amount that is less than or equal to 10%, e.g., less than or equal to 9%, e.g., less than or equal to 8%, e.g., less than or equal to 7%, e.g., less than or equal to 6%, e.g., less than or equal to 5%, e.g., less than or equal to 4%, e.g., less than or equal to 3%, e.g., less than or equal to 2%, e.g., less than or equal to 1.5%, e.g., less than or equal to 1.4%, e.g., less than or equal to 1%, e.g., less than or equal to 0.5%, e.g., less than or equal to 0.4%, e.g., less than or equal to 0.3%, e.g., less than or equal to 0.2%, e.g., less than or equal to 0.175%, e.g., less than or equal to 0.15%, e.g., less than or equal to 0.125%, e.g., less than or equal to 0.1%, e.g., less than or equal to 0.75%, e.g., less than or equal to 0.5%, e.g., less than or equal to 0.25%, and e.g., 0%. In specific embodiments the purity-enhanced sulfonate derivatized compound comprises significantly free of organic by-products, e.g., by-products composed, at least partially, of carbon atoms, e.g., 3-bromopropan-1-ol (or any other of possible intermediates shown above the in the Background section). In additional specific embodiments, the purity-enhanced sulfonate derivatized compound comprises significantly free of nitrogen-containing organic by-products, i.e., organic by-products containing nitrogen, e.g., 3-CPA. In yet another specific embodiment of the invention, the purity-enhanced sulfonate derivatized compound is significantly free of inorganic by-products, e.g., by-products not containing any carbon atoms, e.g., inorganic salts such as Br salts (e.g., NaBr), Cl salts (e.g., NaCl), $SO_3$ salts or $SO_4$ salts. It should be noted that the percentages used in the context of percentage of by-products is intended to describe percentages relative to the weight of the final product, e.g., pharmaceutical composition (i.e., weight by weight, w/w).

In one embodiment in which the sulfonate derivatized compound is a 1,3-propanedisulfonic acid or ester, or salt thereof, the sulfate content is less than or equal to 1.5%, and any other by-products have a content of less than 0.5% each. In another embodiment in which the sulfonate derivatized compound is 3-amino-1-propanesulfonic acid or ester, or salt thereof, the sulfate content is less than or equal to 0.2%, the sulfite content is less than or equal to 0.2%, the sodium content is less than or equal to 1.0%, the chloride content is less than or equal to 0.2%, with a total by-product content of less than 2.0%.

In another embodiment, the invention is directed to a method of preparation of a pharmaceutically-useful sulfonate derivatized compound comprising opening a sultone ring with a nucleophile, such that a pharmaceutically-useful sulfonate derivatized compound is produced.

The language "pharmaceutically-useful" includes sulfonate derivatized compounds that are of a purity such that they would be suitable in pharmaceutical compositions, i.e., capable of being administered to a subject, e.g., a human, e.g., including, but not limited to the sulfonate derivatized compounds produced by the methods of the invention. In certain embodiments, pharmaceutically-useful compounds are obtained from the crude reaction mixture, without the need for further purification. In alternative embodiments, the pharmaceutically-useful compounds that are obtained from the crude reaction mixture are purified prior to incorporation into a pharmaceutical composition. In certain embodiments, the pharmaceutically-useful compounds are greater than or equal to 90% pure, e.g., greater than or equal to 91% pure, e.g., greater than or equal to 92% pure, e.g., greater than or equal to 93% pure, e.g., greater than or equal to 94% pure, e.g., greater than or equal to 95% pure, e.g., greater than or equal to 96% pure, e.g., greater than or equal to 97% pure, e.g., greater than or equal to 98% pure, e.g., greater than or equal to 98.2% pure, e.g., greater than or equal to 98.4% pure, e.g., greater than or equal to 98.6% pure, e.g., greater than or equal to 98.8% pure, e.g., greater than or equal to 98.9% pure, e.g., greater than or equal to 99% pure, e.g., greater than or equal to 99.1% pure, e.g., greater than or equal to 99.2% pure, e.g., greater than or equal to 99.3% pure, e.g., greater than or equal to 99.4% pure, e.g., greater than or equal to 99.5% pure, e.g., greater than or equal to 99.6% pure, e.g., greater than or equal to 99.7% pure, e.g., greater than or equal to 99.8% pure, e.g., greater than or equal to 99.9% pure, and e.g., equal to 100% pure. It should be noted that pharmaceutically-useful compounds of the invention are not intended to be limited by scale of the reaction that produces the compounds.

In an additional embodiment, the invention is directed to a method of preparation of a pharmaceutical composition comprising a pharmaceutical drug candidate and a pharmaceutically acceptable carrier, the method comprising opening a sultone ring with a nucleophile, resulting in a pharmaceutical drug candidate; and combining the pharmaceutical drug candidate with a pharmaceutically acceptable carrier, forming the pharmaceutical composition.

In another embodiment, the invention is directed to a purity-enhanced pharmaceutical drug candidate comprising: 1,3-propanedisulfonic acid or a salt thereof, wherein the pharmaceutical drug candidate is free of bromide.

The language "free of" is used herein, in reference to a final product of a sulfonate derivatized compound, e.g., a pharmaceutical drug candidate, i.e., derived from a crude or purified reaction mixture, which is completely lacking a referenced item, for example, a by-product (such as bromide), which has been introduced into the reaction through the synthetic process. For example, in certain embodiments, the language "free of" is not intended to encompass impurities, for example, residual sodium, which has been introduced through environmental factors rather than through the synthetic process.

In another embodiment, the invention is directed to a purity-enhanced pharmaceutical drug candidate comprising: 1,3-propanedisulfonic acid or a salt thereof, wherein the pharmaceutical drug candidate is free of sodium.

In yet another embodiment, the invention is directed to a purity-enhanced pharmaceutical drug candidate comprising: 1,3-propanedisulfonic acid or a salt thereof, wherein the sulfate content is less than 1.4%. In certain embodiments, the sulfate content is less than 1.0%, e.g., less than 0.9%, e.g., less than 0.8%, e.g., less than 0.7%, e.g., less than 0.6%, e.g., less than 0.5%, e.g., less than 0.4%, e.g., less than 0.3%, e.g., less than 0.2%, e.g., less than 0.1%, e.g., and less than 0.05%.

In an additional embodiment, the invention pertains to a purity-enhanced pharmaceutical drug candidate comprising: 1,3-propanedisulfonic acid or a salt thereof, wherein the pharmaceutical drug candidate is free of at least one of the by-products selected from the group consisting of 1,3-propanediol, 3-bromo-propan-1-ol, 1,3-dibromopropane, and 3-bromo-propanesulfonate. In particular embodiment, the pharmaceutical drug candidate is free of at least two of the by-products selected from the group consisting of 1,3-propanediol, 3-bromo-propan-1-ol, 1,3-dibromopropane, and 3-bromo-propanesulfonate. In another particular embodiment, the pharmaceutical drug candidate is free of at least three of the by-products selected from the group consisting of 1,3-propanediol, 3-bromo-propan-1-ol, 1,3-dibromopropane, and 3-bromo-propanesulfonate. In yet another particular embodiment, the pharmaceutical drug candidate is free of the four by-products selected from the group consisting of 1,3-propanediol, 3-bromo-propan-1-ol, 1,3-dibromopropane, and 3-bromo-propanesulfonate.

Another embodiment of the invention is directed to a purity-enhanced pharmaceutical drug candidate comprising: 3-amino-1-propanesulfonic acid or a salt thereof, wherein the pharmaceutical drug candidate is free of chloride.

An additional embodiment of the invention pertains to a purity-enhanced pharmaceutical drug candidate comprising: 3-amino-1-propanesulfonic acid or a salt thereof, wherein the pharmaceutical drug candidate is free of sodium.

In another embodiment, the invention is a purity-enhanced pharmaceutical drug candidate comprising: 3-amino-1-propanesulfonic acid or a salt thereof, wherein the pharmaceutical drug candidate is free of 3-CPA.

An additional embodiment of the invention is directed to a pharmaceutical drug candidate comprising a sulfonate derivatized compound, which is greater than or equal to 95%, e.g., greater than or equal to 96%, e.g., greater than or equal to 97%, e.g., greater than or equal to 97.5%, e.g., greater than or equal to 98%, e.g., greater than or equal to 98.5%, e.g., greater than or equal to 98.75%, e.g., greater than or equal to 99%, e.g., greater than or equal to 99.25%, e.g., greater than or equal to 99.5%, and e.g., greater than or equal to 99.9%, pure and is fress of a bromide and free of chloride.

Another embodiment of the invention is directed to a purity-enhanced pharmaceutical drug candidate comprising a sulfonate derivatized compound which is significantly free of by-products.

In another embodiment aspect, the invention is a pharmaceutically-useful pharmaceutical drug candidate comprising a sulfonate derivatized compound which is suitable for use in a pharmaceutical composition.

Furthermore, it should be noted that the compounds, e.g., compounds of the invention, may be both purity-enhanced and pharmaceutically useful, as described herein.

The methods of the invention may further comprise a step of purifying the reaction product, i.e., a sulfonate derivatized compound, e.g., a pharmaceutical drug candidate, obtained from the sultone ring opening reaction methodology of the present invention. The methods may also additionally comprise the step of further modifying the pharmaceutical drug candidate, e.g., structurally altering the PDC or reformulating the PDC such that the PDC performs its intended function.

The reactions/methodologies are advantageous or beneficial as compared with the existing methodology in several ways.

I. Analysis of Beneficial Reaction Properties

In one embodiment, the methods of preparation of the invention are advantageous over the methods that are currently in use. In certain embodiments, a method of the invention possesses a beneficial reaction property (BRP).

The language "beneficial reaction property or BRP" includes a property of one reaction that is beneficial over an existing manner of performing the same reaction. The property may be any property suitable to comparison to the existing methodology, such that the property is equal to or better in nature than the property of the existing methodology. Examples of such properties include, without limitation, starting material safety, reaction time, energy cost, reaction safety, product mass balance (reduction of waste), reaction cleanliness, waste, throughput, sulfate levels/workup (i.e., with respect to workup of the reaction), overall process time, and the overall cost of the target product. Several particular examples of beneficial reaction properties as applied to the preparation of 1,3-propanedisulfonic acid disodium salt are discussed below.

Safety of the Starting Materials

In the methodology that is currently used to prepare 1,3-propanedisulfonic acid disodium salt, the starting material is 1,3-dibromopropane, which is a toxic lacrymor liquid. As such, storage and use of the starting material in the reactions is made difficult. In contrast, while 1,3-propane sultone is toxic, the advantage of 1,3-propane sultone is that it is a crystalline solid at room temperature. Therefore, storage in a dry environment of this starting material has obvious advantages, e.g., in the situation in which there is a damaged container. Moreover, containment of such a spill is made easier by the ability to rapidly hydrolyze 1,3-propane sultone to the less harmful 3-hydroxy-1-propanesulfonic acid.

Energy Cost and Reaction Safety

The 1,3-dibromopropane reaction requires high temperature (90 to 100° C.), while in certain embodiments, the 1,3-propane sultone reaction is performed under cooling conditions (10 to 15° C.), at least at the beginning, to minimize the hydrolysis of the starting material (side reaction) and to absorb the exotherm. The exotherm is contained by a controlled addition rate of the 1,3-propane sultone, as a solution, to the cold aqueous solution of sodium sulfite. A steady temperature is reached during the course of the addition. Then, the temperature of the mixture is reduced, for example, to the temperature of a circulating cooling system.

In one embodiment, it is possible to allow the reaction to cool to room temperature after the end of the addition without the assistance of a cooling apparatus, thus reducing the energy costs.

Waste

Theoretically, for the 1,3-dibromopropane route, 45% of the mass on the product side is waste; as compared to 0% for the 1,3-propane sultone route. Moreover, in the 1,3-dibromopropane route the mass of solid waste is in solution in the filtrate of the precipitations. The filtrate is halogenated waste, and therefore disposal costs are higher.

In regard to the total amount of waste, the 1,3-propane sultone route can reduce waste by about 50% over the 1,3-dibromopropane route, if only two precipitations are used in the 1,3-dibromopropane route. If more precipitations are required for the 1,3-dibromopropane route, the advantage of the 1,3-propane sultone route will be even greater.

Product Mass Balance

The mass balance of product is only 55% for the 1,3-dibromopropane route; as compared to 100 percent for the 1,3-propane sultone route.

Impurities/Cleanliness

The 1,3-propane sultone synthetic route has only one side reaction: the hydrolysis of 1,3-propane sultone by water which produces only one by-product from the reaction (3-hydroxy-1-propanesulfonic acid sodium salt, see below).

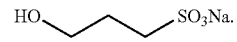

As this side product is ionic, it is easily detected by ion liquid chromatography. In addition, in the methods of the present application, there is no apparent further oxidation of sulfite into sulfate (which is present as an impurity in the sodium sulfite, regardless of the grade).

In an additional advantage, there is no NaBr or other inorganic salt produced by the reaction. As a result, the cleanup of the reaction mixture becomes much easier. In fact, even if ethanol precipitation is utilized for final product purification, the amount of ethanol utilized would be reduced dramatically as compared to that used to remove inorganic salts in the 1,3-dibromopropane route. Decreasing the volume of ethanol will increase the throughput of the production by increasing batch size, and will also reduce production cost. Eliminating the step of removal of NaBr in the purification also reduces the time required for the process.

In contrast, several by-products are theoretically possible and are commonly obtained in the 1,3-dibromopropane route, as described above. Some of these by-products, like 1,3-propanediol, are non-ionic, resulting in the need for the use of additional analytical techniques, such as gas chromatography. Moreover, in the 1,3-dibromopropane route, there is some oxidation of the sulfite into sulfate during the course of the reaction.

Furthermore, the level of sulfates reached for the 1,3-dibromopropane route may sometimes require additional treatments to lower sulfate below acceptable limits for pharmaceutical compositions. The known methodology for the reduction/removal of sulfates has been the use of barium, i.e., precipitating the sulfate as an insoluble barium salt (in aqueous solutions). There are two concerns about the barium treatment for the removal of sulfate and sulfite: (1) the presence of a residual heavy metal (barium) in the final drug candidate that may cause concern when administered to animal subjects, e.g., humans, and (2) the increase in the labor/steps in the process of preparation.

Throughput

The throughput for the 1,3-dibromopropane route ranges within 33 to 38 kg per batch for a 2,000-L reactor. The expected throughput for the 1,3-propane sultone route is about 260 kilograms per batch for a 2,000-L reactor (i.e., a 5.8 to 6.8-fold increase as compared with the current 1,3-dibromopropane route).

In certain embodiments the throughput may be defined by the "load capacity," which, in turn, may be calculated by using the following equation:

$$\frac{\text{Amount of Product}}{\text{Reaction Size}} \times 100\% = \text{Load Capacity}$$

For example, the load capacity of the 260 kilogram sultone batch (described above) in a 2,000-L reactor is 13% as compared with about 1.8% load capacity for the 1,3-dibromopropane route.

In one embodiment, the invention is a method of enhanced throughput production of a sulfonate derivatized compound comprising opening a sultone ring with a nucleophile, such that enhanced throughput of a sulfonate derivatized compound occurs.

The language "enhanced throughput production," is a characteristic of a process (independent of scale), e.g., a chemical synthetic process of the invention, which demonstrates improved throughput. Moreover, enhanced throughput is a measurable quantity, which may be measured both qualitatively, i.e., showing qualitative improvement in throughput, or quantitatively, i.e., showing quantitative or quantifiable improvement in the throughput, and may be measured/determined, for example, by comparing the load capacity of the processes. In certain embodiments of the invention, the load capacity is greater than the load capacity of the existing methodology. In particular embodiments, the load capacity of the sultone route is greater than or equal to 2%, e.g., greater than or equal to 3%, e.g., greater than or equal to 4%, e.g., greater than or equal to 5%, e.g., greater than or equal to 6%, e.g., greater than or equal to 7%, e.g., greater than or equal to 8%, e.g., greater than or equal to 9%, e.g., greater than or equal to 10%, e.g., greater than or equal to 11%, e.g., greater than or equal to 12%, e.g., greater than or equal to 13%, and e.g., greater than or equal to 15%

III. Chemistry Development

The synthetic chemistry of the present invention was examined for selection of the appropriate reaction conditions. The following aspects were examined for possible optimization: the solvent and co-solvent in which to perform the reaction; the reaction profile as applicable to starting material consumption and side product formation; temperature profile as applicable to starting material consumption and side product formation; the work-up and purification of the reaction mixture; and the water content of the product. The scheme (Scheme 1) listed below, with examples of conditions such as starting material, solvent and temperature, are only intended to be instructive, and are not intended to be limiting.

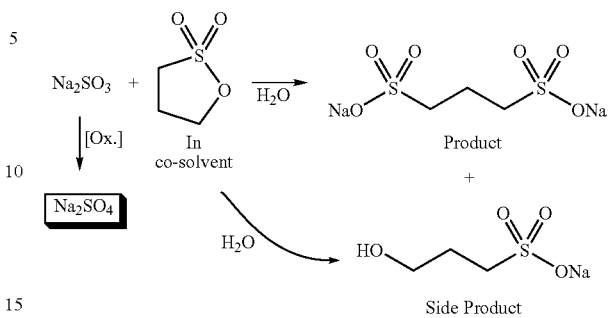

Scheme 1

Solvent

In one embodiment, the main solvent useful in the methods of the invention is selected such that the solvent has the ability to solubilize, at least in part, the starting material, e.g., the nucleophile (i.e., when sodium sulfite is the starting material nucleophile, water may be selected as the main solvent). In an alternative embodiment, the main solvent useful in the methods of the invention is selected such that the solvent does not affect, e.g., increase or insignificantly decrease, the nucleophilic character of the desired nucleophile (i.e., the desired atom within complex molecules). For example, in certain embodiments of the invention, when the desired nucleophile is the sulfur of a sulfite anion, the solvent is selected to be $H_2O$, which increases the nucleophilicity of the sulfur in the sulfite anion.

The co-solvent may include any solvent that is: at least partially miscible with the main solvent (such that the reaction may proceed); at least partially miscible with the starting material, e.g., the sultone ring; and does not substantially affect the sultone ring opening reaction. Exemplary solvents include, but are not limited to methanol, toluene, tetrahydrofuran, acetonitrile, acetone, and 1,4-dioxane. In particular embodiments, the co-solvent is acetone. Acetone is relatively inexpensive, not too toxic, and easy to recover. In embodiments in which acetone is selected as the co-solvent, relatively little degradation, e.g., no degradation, of 1,3-propane sultone by acetone occurs.

There are many reasons for the use of a co-solvent to dissolve the sultone, e.g., 1,3-propane sultone: (1) The sultone may be a solid at room temperature. (2) The melted sultone may be viscous and a co-solvent would therefore help to lower the viscosity and facilitates transfer. (3) The sultone may have a limited solubility in water (e.g., for 1,3-propane sultone, the limited solubility was observed, not measured). However, the partition coefficient of 1,3-propane sultone for water/toluene is 1.4. Therefore, even if only a small amount of toluene is used to keep the 1,3-propane sultone liquid, 1,3-propane sultone prefers to associate with the aqueous phase. (4) Dilution of the sultone helps control the exothermic reaction, even if a bath with a thermostat is used (i.e., heat exchangers have limits).

Furthermore, the amount of co-solvent used should be adequate to allow the ring opening reaction to proceed. In one particular embodiment, the amount of co-solvent used is 1 mL of acetone per gram of 1,3-propane sultone. In certain embodiments, the solvents, i.e., the main solvent and the cosolvent, are selected based on the characteristic of substantial non-toxicity.

Moreover, suitable solvents are liquids at ambient room temperature and pressure or remain in the liquid state under the temperature and pressure conditions used in the reaction. Useful solvents are not particularly restricted provided that they do not interfere with the reaction itself (that is, they preferably are inert solvents), and they dissolve a certain amount of the reactants. Depending on the circumstances, solvents may be distilled or degassed. Solvents may be, for example, aliphatic hydrocarbons (e.g., hexanes, heptanes, ligroin, petroleum ether, cyclohexane, or methylcyclohexane) and halogenated hydrocarbons (e.g., methylenechloride, chloroform, carbontetrachloride, dichloroethane, chlorobenzene, or dichlorobenzene); aromatic hydrocarbons (e.g., benzene, toluene, tetrahydronaphthalene, ethylbenzene, or xylene); ethers (e.g., diglyme, methyl-tert-butyl ether, methyl-tert-amyl ether, ethyl-tert-butyl ether, diethylether, diisopropylether, tetrahydrofuran or methyltetrahydrofurans, dioxane, dimethoxyethane, or diethyleneglycol dimethylether); nitrites (e.g., acetonitrile); ketones (e.g., acetone); esters (e.g., methyl acetate or ethyl acetate); and mixtures thereof.

Reaction Profile

In certain embodiments, the reaction is fast upon addition of the first aliquot of nucleophile to the sultone, i.e., as observed by NMR the first half-equivalent is completely consumed as it is added. At the end of the addition with 10% excess, about 5% of the starting material (seen in the aqueous layer, by NMR) remains unreacted a few minutes after the end of the addition. After this point, the disappearance of the sultone, e.g., 1,3-propane sultone, slows down as the acidity increases.

In one embodiment, the excess sultone, e.g., 1,3-propane sultone, is removed in the reaction work-up. In an alternative embodiment, the excess sultone, e.g., 1,3-propane sultone, is removed by hydrolysis. Furthermore, HPLC analysis can be used to determine how much of an excess of the sultone is required to consume the nucleophile, e.g., sodium sulfite, in order to limit unnecessary purification steps.

Temperature Profile

In one embodiment, the sulfite anion solution is equilibrated at the temperature of the circulating cooling system, e.g., a water bath equipped with a copper coil. It was observed that the temperature of reaction mixture increases rapidly to a plateau where a steady state is obtained, i.e., the exotherm of the reaction is in equilibrium with the heat removal capacity of the cooling system. In certain embodiments (as shown below), the change in temperature increase was less than 5° C. for a 300-g scale reaction.

In certain embodiments, the changes in relative concentration of the starting material at about 1 hour after the addition, occur relatively slowly. HPLC (in real time) can be used to monitor the reaction. However, a method to quench the remaining sulfite (e.g., peroxide) and to destroy the excess sultone, e.g., 1,3-propane sultone, may be necessary because the sultone, e.g., 1,3-propane sultone, may not degrade in a regular fashion in the mobile phase of the HPLC column depending on the time it is sitting in the HPLC auto-sampler area.

In one example, in which the starting material is 1,3-propane sultone, it has been determined that the lower the temperature, the slower is the hydrolysis of the starting material. In one embodiment, the temperature is increased at the end of the reaction, e.g., to increase the speed of the desired reaction and/or increase the hydrolysis of the excess starting material. In another embodiment, in parallel to the temperature increase, the pH is maintained in a range of 4-6.

IV. Compounds Prepared Using Methods of the Invention

In general, the sulfonate derivatized compounds appropriate for use in the therapeutic formulations of the invention comprise at least one sulfonate group covalently bonded to a substituted or unsubstituted aliphatic group, e.g., substituted or unsubstituted alkyl, e.g., propyl or butyl.

In an additional embodiment, the sulfonate derivatized compound has at least two sulfonate groups covalently bonded to a substituted or unsubstituted aliphatic group. In another embodiment, the sulfonate derivatized compound has at least one sulfonate group covalently bonded to a substituted or unsubstituted lower alkyl group. In a similar embodiment the sulfonate derivatized compound has at least two sulfonate groups covalently bonded to a substituted or unsubstituted lower alkyl group.

In certain embodiments, the invention is directed to the preparation of a substituted or unsubstituted alkylsulfonic acid, substituted or unsubstituted alkylsulfuric acid, substituted or unsubstituted alkylthiosulfonic acid, substituted or unsubstituted alkylthiosulfuric acid, or an ester or amide thereof, including pharmaceutically acceptable salts thereof. For example, the invention relates to a compound that is a substituted or unsubstituted alkylsulfonic acid, or an ester or amide thereof, including pharmaceutically acceptable salts thereof. In another embodiment, the invention pertains to a compound that is a substituted or unsubstituted lower alkylsulfonic acid, or an ester or amide thereof, including pharmaceutically acceptable salts thereof. Similarly, the invention includes a compound that is a (substituted- or unsubstituted-amino)-substituted alkylsulfonic acid, or an ester or amide thereof, including pharmaceutically acceptable salts thereof. In yet another embodiment, the compound is a (substituted- or unsubstituted-amino)-substituted lower alkylsulfonic acid, or an ester or amide thereof, including pharmaceutically acceptable salts thereof.

Compositions of alkylsulfonic acids, including, for example, 3-amino-1-propanesulfonic acid and certain salts thereof have been shown to be useful in the treatment of amyloid-β related diseases, including Alzheimer's disease and cerebral amyloid angiopathy. See WO 96/28187, WO 01/85093, and U.S. Pat. No. 5,840,294.

The term "alkylsulfonic acid" as used herein includes substituted or unsubstituted alkylsulfonic acids, and substituted or unsubstituted lower alkylsulfonic acids. Amino-substituted compounds are especially noteworthy and the invention pertains to substituted- or unsubstituted-amino-substituted alkylsulfonic acids, and substituted- or unsubstituted-amino-substituted lower alkylsulfonic acids, an example of which is 3-amino-1-propanesulfonic acid. Also, it should be noted that the term "alkylsulfonic acid" as used herein is to be interpreted as being synonymous with the term "alkanesulfonic acid."

A "sulfonic acid" or "sulfonate" group is a —$SO_3H$ or —$SO_3^-X^+$ group bonded to a carbon atom, where $X^+$ is a cationic counter ion group. Similarly, a "sulfonic acid" compound has a —$SO_3H$ or —$SO_3^-X^+$ group bonded to a carbon atom, where X+ is a cationic counter ion group. A "sulfate" as used herein is a —$OSO_3H$ or —$OSO_3^-X^+$ group bonded to a carbon atom, and a "sulfuric acid" compound has a —$SO_3H$ or —$OSO_3^-X^+$ group bonded to a carbon atom, where $X^+$ is a cationic counter ion group. According to the invention, a suitable cationic group may be a hydrogen atom. In certain cases, the cationic group may actually be another group on the therapeutic compound that is positively charged at physiological pH, for example an amino group. A "counter ion" is helpful in maintaining electroneutrality, and is pharmaceutically acceptable in the compositions of the invention. Compounds containing a cationic group covalently bonded to an anionic group may be referred to as an "inner salt."

One group of example alkylsulfonic acids have the following structure

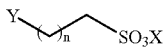

where Y is either an amino group (having the formula —NR$^a$R$^b$, wherein R$^a$ and R$^b$ are each independently hydrogen, alkyl, aryl, or heterocyclyl, or R$^a$ and R$^b$, taken together with the nitrogen atom to which they are attached, form a cyclic moiety having from 3 to 8 atoms in the ring) or a sulfonic acid group (having the formula —SO$_3^-$X$^+$), n is an integer from 1 to 5, and X is hydrogen or a cationic group (e.g., sodium). Some exemplary alkylsulfonic acids include the following

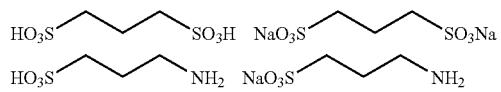

In general, the compounds of the present invention may be prepared by the methods illustrated in the general reaction schemes as, for example, described herein, or by modifications thereof, e.g., using readily available starting materials, reagents and conventional synthesis procedures. In these reactions, it is also possible to make use of variants which are in themselves known, but are not mentioned here. For example, functional and structural equivalents of the compounds described herein and which have the same general properties, (wherein one or more simple variations of substituents are made that do not adversely affect the essential nature or the utility of the compound) may be prepared according to a variety of methods known in the art. The agents of the present invention may be readily prepared in accordance with the synthesis schemes and protocols described herein, as illustrated in the specific procedures provided. It will be further recognized that various protecting and deprotecting strategies will be employed that are standard in the art (See, e.g., "Protective Groups in Organic Synthesis" by Greene and Wuts). Those skilled in the relevant arts will recognize that the selection of any particular protecting group (e.g., amine and carboxyl protecting groups) will depend on the stability of the protected moiety with regards to the subsequent reaction conditions and will understand the appropriate selections. Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Comprehensive Organic Transformations" by R. Larock, VCH Publishers (1989); T. D. Ocain, et al., J. Med. Chem. 31, 2193-99 (1988); E. M. Gordon, et al., J. Med. Chem. 31, 2199-10 (1988); "Practice of Peptide Synthesis" by M. Bodansky and A. Bodanszky, Springer-Verlag, New York (1984); "Protective Groups in Organic Synthesis" by T. Greene and P. Wuts (1991); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992).

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like, as well as polymorphic forms, e.g., including pseudopolymorphic forms. The term "solvate" represents an aggregate that comprises one or more molecules of a compound, with one or more molecules of a pharmaceutical solvent, such as water, ethanol, and the like.

In an embodiment, the invention pertains, at least in part to the preparation of a composition having a compound that is a compound of Formula I-A:

(I-A)

wherein:

R$^1$ is a substituted or unsubstituted cycloalkyl, aryl, arylcycloalkyl, bicyclic or tricyclic ring, a bicyclic or tricyclic fused ring group, or a substituted or unsubstituted C$_2$-C$_{10}$ alkyl group;

R$^2$ is selected from the group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is SO$_3^-$X$^+$, OSO$_3^-$X$^+$, or SSO$_3^-$X$^+$;

X$^+$ is hydrogen, a cationic group, or an ester forming group (i.e., as in a prodrug); and each of L$^1$ and L$^2$ is independently a substituted or unsubstituted C$_1$-C$_5$ alkyl group or absent, or a pharmaceutically acceptable salt thereof, provided that when R$^1$ is alkyl, L$^1$ is absent.

In another embodiment, the invention pertains, at least in part to the preparation of a composition having a compound that is a compound of Formula II-A:

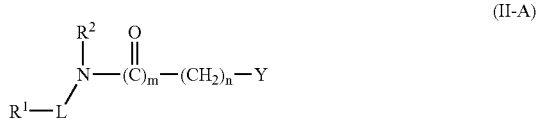

(II-A)

wherein:

R¹ is a substituted or unsubstituted cyclic, bicyclic, tricyclic, or benzoheterocyclic group or a substituted or unsubstituted $C_2$-$C_{10}$ alkyl group;

R² is hydrogen, alkyl, mercaptoalkyl, alkenyl, alkynyl, cycloalkyl, aryl, arylalkyl, thiazolyl, triazolyl, imidazolyl, benzothiazolyl, benzoimidazolyl, or linked to R¹ to form a heterocycle;

Y is $SO_3^{-X+}$, $OSO_3^-X^+$, or $SSO_3^-X^+$;

X⁺ is hydrogen, a cationic group, or an ester forming moiety;

m is 0 or 1;

n is 1, 2, 3, or 4;

L is substituted or unsubstituted $C_1$-$C_3$ alkyl group or absent, or a pharmaceutically acceptable salt thereof, provided that when R¹ is alkyl, L is absent. In a particular embodiment, n is 3 or 4.

In yet another embodiment, the invention pertains, at least in part to the preparation of a composition having a compound that is a compound of Formula III-A:

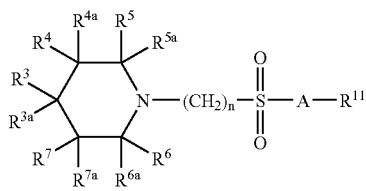

(III-A)

wherein:

A is nitrogen or oxygen;

R¹¹ is hydrogen, salt-forming cation, ester forming group, —(CH₂)ₓ—Q, or when A is nitrogen, A and R¹¹ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

R³, R³ᵃ, R⁴, R⁴ᵃ, R⁵, R⁵ᵃ, R⁶, R⁶ᵃ, R⁷ and R⁷ᵃ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond. In a particular embodiment, n is 3 or 4. In certain embodiments, one of R³, R³ᵃ, R⁴, R⁴ᵃ, R⁵, R⁵ᵃ, R⁶, R⁶ᵃ, R⁷ and R⁷ᵃ is a moiety of Formula IIIa-A:

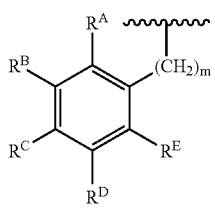

(IIIa-A)

wherein:

m is 0, 1, 2, 3, or 4;

Rᴬ, Rᴮ, Rᶜ, Rᴰ, and Rᴱ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; and pharmaceutically acceptable salts and esters thereof. In a particular embodiment, n is 3 or 4. In certain embodiments, said compound is not 3-(4-phenyl-1,2,3,6-tetrahydro-1-pyridyl)-1-propanesulfonic acid.

An ester forming group or moiety includes groups, which when bound, form an ester. Examples of such groups include substituted or unsubstituted alkyl, aryl, alkenyl, alkynyl, or cycloalkyl. Particular examples of possible esters include methyl, ethyl, and t-butyl. Additionally, examples of salt forming cations include pharmaceutically acceptable salts described herein as well as lithium, sodium, potassium, magnesium, calcium, barium, zinc, iron, and ammonium. In a further embodiment, the salt forming cation is a sodium salt.

In yet another embodiment, the invention pertains at least in part to the preparation of a composition having a compound that is a compound of Formula IV:

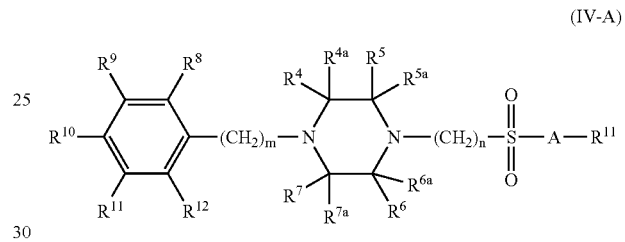

(IV-A)

wherein:

A is nitrogen or oxygen;

R¹¹ is hydrogen, salt-forming cation, ester forming group, —(CH₂)ₓ—Q, or when A is nitrogen, A and R¹¹ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

R⁴, R⁴ᵃ, R⁵, R⁵ᵃ, R⁶, R⁶ᵃ, R⁷, and R⁷ᵃ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, R⁴ and R⁵ taken together, with the ring atoms they are attached to, form a double bond, or R⁶ and R⁷ taken together, with the ring atoms they are attached to, form a double bond;

m is 0, 1, 2, 3, or 4;

R⁸, R⁹, R¹⁰, R¹¹, and R¹² are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl, and pharmaceutically acceptable salts and esters thereof. In a particular embodiment, n is 3 or 4.

In another embodiment, the invention includes the preparation of a composition having a compound that is a compound of Formula V-A:

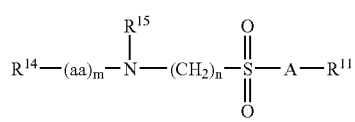

(V-A)

wherein:

A is nitrogen or oxygen;

$R^{11}$ is hydrogen, salt-forming cation, ester forming group, —$(CH_2)_x$—Q, or when A is nitrogen, A and $R^{11}$ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

aa is a natural or unnatural amino acid residue;

m is 0, 1, 2, or 3;

$R^{14}$ is hydrogen or protecting group;

$R^{15}$ is hydrogen, alkyl or aryl, and pharmaceutically acceptable salts and prodrugs thereof. In a particular embodiment, n is 3 or 4.

In another embodiment, the invention includes the preparation of a composition having a compound that is a compound of the Formula VI-A:

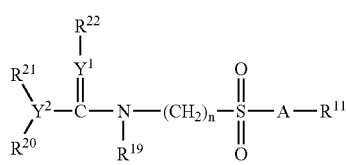

(VI-A)

wherein:

n is 1, 2, 3, 4, 5, 6, 7, 8, 9, or 10;

A is oxygen or nitrogen;

$R^{11}$ is hydrogen, salt-forming cation, ester forming group, —$(CH_2)_x$—Q, or when A is nitrogen, A and $R^{11}$ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

$R^{19}$ is hydrogen, alkyl or aryl;

$Y^1$ is oxygen, sulfur, or nitrogen;

$Y^2$ is carbon, nitrogen, or oxygen;

$R^{20}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl;

$R^{21}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl, or absent if $Y^2$ is oxygen;

$R^{22}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl; or $R^{22}$ is hydrogen, hydroxyl, alkoxy or aryloxy if $Y^1$ is nitrogen; or $R^{22}$ is absent if $Y^1$ is oxygen or sulfur; or $R^{22}$ and $R^{21}$ may be linked to form a cyclic moiety if $Y^1$ is nitrogen;

or pharmaceutically acceptable salts thereof. In a particular embodiment, n is 3 or 4.

In another embodiment, the invention includes the preparation of a composition having a compound that is a compound of Formula VII-A:

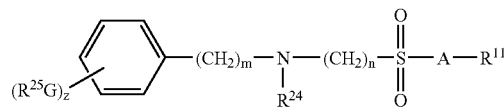

(VII-A)

wherein:

n is 2, 3, or 4;

A is oxygen or nitrogen;

$R^{11}$ is hydrogen, salt-forming cation, ester forming group, —$(CH_2)_x$—Q, or when A is nitrogen, A and $R^{11}$ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

G is a direct bond or oxygen, nitrogen, or sulfur;

z is 0, 1, 2, 3, 4, or 5;

m is 0 or 1;

$R^{24}$ is selected from the group consisting of hydrogen, alkyl, mercaptoalkyl, alkenyl, alkynyl, aroyl, alkylcarbonyl, aminoalkylcarbonyl, cycloalkyl, aryl, arylalkyl, thiazolyl, triazolyl, imidazolyl, benzothiazolyl, and benzoimidazolyl;

each $R^{25}$ is independently selected from hydrogen, halogen, cyano, hydroxyl, alkoxy, thiol, amino, nitro, alkyl, aryl, carbocyclic, or heterocyclic, and pharmaceutically acceptable salts thereof. In a particular embodiment, n is 1 or 2.

Additional compounds that may prepared by the methods of the present invention include, for example, compounds of Formula (I-B):

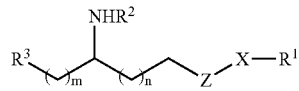

(I-B)

wherein:

X is oxygen or nitrogen;

Z is C=O, $S(O)_2$, or $P(O)OR^7$;

m and n are each independently 0, 1, 2, 3, 4, 5, 6, 7, 8, 9 or 10;

$R^1$ and $R^7$ are each independently hydrogen, metal ion, alkyl, mercaptoalkyl, alkenyl, alkynyl, cycloalkyl, aryl, a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

p is 0, 1, 2, 3, or 4;

$R^2$ is hydrogen, alkyl, mercaptoalkyl, alkenyl, alkynyl, cycloalkyl, aryl, alkylcarbonyl, arylcarbonyl, or alkoxycarbonyl;

$R^3$ is hydrogen, amino, cyano, alkyl, mercaptoalkyl, alkenyl, alkynyl, cycloalkyl, heterocyclic, sunbstituted or unsubstituted aryl, heteroaryl, thiazolyl, triazolyl, tetrazolyl, imidazolyl, benzothiazolyl, or benzoimidazolyl, and pharmaceutically acceptable salts, esters, and prodrugs thereof.

In a further embodiment, m is 0, 1, or 2. In another further embodiment, n is 0, 1, or 2, e.g., 1 or 2. In another further embodiment, $R^3$ is aryl, e.g., heteroaryl or phenyl. In yet another embodiment, Z is $S(O)_2$.

In another embodiment, the compound prepared by the methods of the invention is of the Formula (II-B)

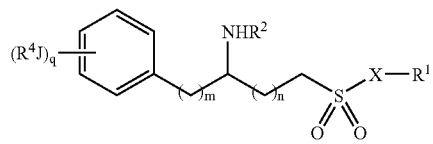
(II-B)

wherein:

X is oxygen or nitrogen;

m and n are each independently 0, 1, 2, 3, 4, 5, 6, 7, 8, 9 or 10;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

each $R^4$ is independently selected from the group consisting of hydrogen, halogen, hydroxyl, thiol, amino, cyano, nitro, alkyl, aryl, carbocyclic or heterocyclic;

$R^2$ is hydrogen, alkyl, mercaptoalkyl, alkenyl, alkynyl, cycloalkyl, aryl, alkylcarbonyl, arylcarbonyl, or alkoxycarbonyl;

J is absent, oxygen, nitrogen, sulfur, or a divalent link-moiety consisting of, without limitation to, lower alkylene, alkylenyloxy, alkylenylamino, alkylenylthio, alkylenyloxyalkyl, alkylenylamonialkyl, alkylenylthioalkyl, alkenyl, alkenyloxy, alkenylamino, or alkenylthio; and q is 1, 2, 3, 4, or 5, and pharmaceutically acceptable salts, esters and prodrugs thereof. In a particular embodiment, n is 1 or 2.

In a yet further embodiment, the compound prepared by the methods of the invention is of the Formula (III-B):

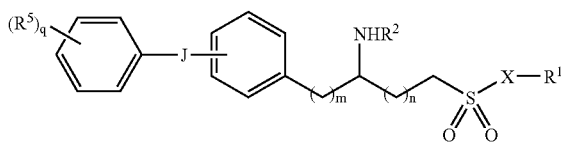
(III-B)

wherein:

X is oxygen or nitrogen;

m and n are each independently 0, 1, 2, 3, 4, 5, 6, 7, 8, 9 or 10;

q is 1, 2, 3, 4, or 5;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

p is 0, 1, 2, 3, or 4;

$R^2$ is hydrogen, alkyl, mercaptoalkyl, alkenyl, alkynyl, cycloalkyl, aryl, alkylcarbonyl, arylcarbonyl, or alkoxycarbonyl;

$R^5$ is selected from the group consisting of hydrogen, halogen, amino, nitro, hydroxy, carbonyl, thiol, carboxy, alkyl, alkoxy, alkoxycarbonyl, acyl, alkylamino, and acylamino;

J is absent, oxygen, nitrogen, sulfur, or a divalent link-moiety consisting of, without limitation to, lower alkylene, alkylenyloxy, alkylenylamino, alkylenylthio, alkylenyloxyalkyl, alkylenylamonialkyl, alkylenylthioalkyl, alkenyl, alkenyloxy, alkenylamino, or alkenylthio; and pharmaceutically acceptable salts, esters, and prodrugs thereof. In a particular embodiment, n is 1 or 2.

In yet another embodiment, the compound prepared by the methods of the invention is:

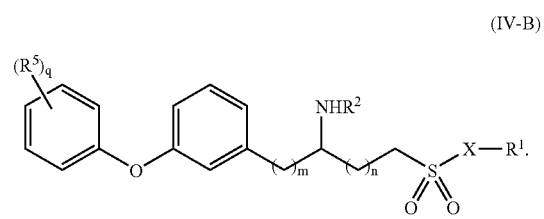
(IV-B)

wherein:

X is oxygen or nitrogen;

m and n are each independently 0, 1, 2, 3, 4, 5, 6, 7, 8, 9 or 10;

q is 1, 2, 3, 4, or 5;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

p is 0, 1, 2, 3, or 4;

$R^2$ is hydrogen, alkyl, mercaptoalkyl, alkenyl, alkynyl, cycloalkyl, aryl, alkylcarbonyl, arylcarbonyl, or alkoxycarbonyl;

$R^5$ is selected from the group consisting of hydrogen, halogen, amino, nitro, hydroxy, carbonyl, thiol, carboxy, alkyl, alkoxy, alkoxycarbonyl, acyl, alkylamino, acylamino; and pharmaceutically acceptable salts, esters, and prodrugs thereof. In a further embodiment, m is 0. In a particular embodiment, n is 1 or 2.

In another embodiment, the invention pertains to compounds of Formula (V-B):

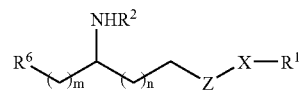
(V-B)

wherein:

Z is C=O, S(O)$_2$, or P(O)OR$^7$;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

m and n are each independently 0, 1, 2, 3, 4, 5, 6, 7, 8, 9 or 10;

$R^2$ is hydrogen, alkyl, mercaptoalkyl, alkenyl, alkynyl, cycloalkyl, aryl, alkylcarbonyl, arylcarbonyl, or alkoxycarbonyl; and $R^6$ is a substituted or unsubstituted heterocyclic moiety. In a further embodiment, m is 0 or 1. In another embodiment, n is 0 or 1. In another further embodiment, $R^6$ is thiazolyl, oxazoylyl, pyrazolyl, indolyl, pyridinyl, thiazinyl, thiophenyl, benzothiophenyl, dihydroimidazolyl, dihydrothiazolyl, oxazolidinyl, thiazolidinyl, tetrahydropyrimidinyl, or oxazinyl. In yet another embodiment, Z is $S(O)_2$. In a particular embodiment, n is 1 or 2.

In yet another embodiment, the sulfonate derivatized compound has at least one sulfonate group covalently bonded to an amino-substituted aliphatic group. In a similar embodiment the sulfonate derivatized compound has at least two sulfonate groups covalently bonded to an amino-substituted aliphatic group. In still yet another embodiment, the sulfonate derivatized compound has at least one sulfonate group covalently bonded to an amino-substituted lower alkyl group. In a similar embodiment the sulfonate derivatized compound has at least two sulfonate groups covalently bonded to an amino-substituted lower alkyl group.

An additional embodiment of the invention pertains to a method of preparation of a 1,3-propanedisulfonic acid compound comprising opening a sultone ring with a nucleophile, wherein said nucleophile is a sulfite anion, such that a 1,3-propanedisulfonic acid compound is produced.

The language "1,3-propanedisulfonic acid compound" includes 1,3-propanedisulfonic acid or any derivative thereof, including substituted derivatives and pharmaceutically acceptable salts, which are capable of being prepared by the methods of the invention.

Another embodiment of the invention is a method of preparation of a 3-amino-1-propanesulfonic acid compound comprising opening a sultone ring with a nucleophile, wherein said nucleophile is ammonia (or ammonium hydroxide), such that a 3-amino-1-propanesulfonic acid compound is produced.

A further embodiment of the invention is a method of preparation of a 3-amino-1-propanesulfonic acid compound comprising opening a sultone with a nucleophile, wherein said nucleophile is azide; and reducing the azide to an amino group, such that a 3-amino-1-propanesulfonic acid compound is produced.

Another further embodiment of the invention is a method of preparation of a 3-amino-1-propanesulfonic acid compound comprising opening a sultone with a nucleophile, wherein said nucleophile is benzylamine; and debenzylating the benzylated intermediate, such that a 3-amino-1-propanesulfonic acid compound is produced.

The language "3-amino-1-propanesulfonic acid compound" is intended to 3-amino-1-propanesulfonic acid or any derivative thereof, including substituted derivatives and pharmaceutically acceptable salts, which are capable of being prepared by the methods of the invention.

In one embodiment, the invention is directed to a sulfonate derivatized compound prepared by the method comprising opening a sultone ring with a nucleophile, resulting in a sulfonate derivatized compound, wherein said nucleophile is a sulfite anion or ammonia, such that a sulfonate derivatized compound is produced. In specific embodiments, the sulfonate derivatized compound is a 1,3-propanedisulfonic acid compound or a 3-amino-1-propanesulfonic acid compound.

In yet another embodiment, the invention includes any novel compound or pharmaceutical compositions containing compounds of the invention described herein. For example, compounds and pharmaceutical compositions containing compounds set forth herein (e.g., Tables 3 and 4) are intended to be a part of this invention.

Additionally, the compounds described above are intended to include analogs containing art-recognized substituents that do not significantly affect the analog's ability to perform its intended function and do not significantly affect the analog's ability to be prepared by the methods of the invention.

In certain embodiments of the invention, the sulfonate derivatized compounds of the invention include, but are not limited to 1,3-propanedisulfonic acid disodium salt, 1,4-butanedisulfonic acid disodium salt, 3-amino-1-propanesulfonic acid, 3-amino-1-propanesulfonic acid, sodium salt, 3-(dimethylamino)-1-propanesulfonic acid, 3-(1,2,3,6-tetrahydropyridinyl)-1-propanesulfonic acid, 3-(1,2,3,4-tetrahydroisoquinolinyl)-1-propanesulfonic acid, 3-(4-cyano-4-phenylpiperidin-1-yl)-1-propanesulfonic acid, 3-[4-(4-fluorophenyl)-1,2,3,6-tetrahydropyridin-1-yl]-1-propanesulfonic acid, 3-[4-(4-bromophenyl)-4-hydroxypiperidin-1-yl]-1-propanesulfonic acid, 3-[4-(4-chlorophenyl)-4-hydroxypiperidin-1-yl]-1-propanesulfonic acid, 3-(4-acetyl-4-phenylpiperidin-1-yl)-1-propanesulfonic acid, 3-[4-(4-chlorophenyl)-1,2,3,6-tetrahydropyridin-1-yl]-1-propanesulfonic acid, 3-tryptamino-1-propanesulfonic acid, 3-(1,2,3,4-tetrahydro-naphthylamino)-1-propanesulfonic acid, 3-(1-adamantylamino)-1-propanesulfonic acid, 3-(2-norbornylamino)-1-propanesulfonic acid, 3-(2-admantylamino)-1-propanesulfonic acid, 3-((4-hydroxy-2-pentyl)amino)-1-propanesulfonic acid, and 3-(t-butylamino)-1-propanesulfonic acid. In another particular embodiment, the sulfonate derivatized compounds of the invention include, but are not limited to the compounds listed in Tables 3 and 4. In one embodiment, the sulfonate derivatized compound is not 4-phenyl-1-(3-sulfopropyl)-1,2,3,6-tetrahydropyridine. In another embodiment, the sulfonate derivatized compound is not 3-(1-Methyl-2-phenylethylamino)-propane-1-sulfonic acid or a salt thereof. In particular embodiments, the sulfonate derivatized compounds of the invention may be prepared in large scale, may be a pharmaceutically-useful sulfonate derivatized compound, and/or may be a purity-enhanced sulfonate derivatized compound.

Further examples of compounds that may be used as a compound according to the present invention include those described in the U.S. provisional patent application No. 60/480,906, filed Jun. 23, 2003, and U.S. provisional patent application No. 60/512,047, filed Oct. 17, 2003, U.S. application Ser. No. 10/871,514, filed Jun. 18, 2004, and U.S. application Ser. No. 10/871,365, filed Jun. 18, 2004, all entitled Methods and Compositions for Treating Amyloid-Related Diseases; and U.S. provisional patent application No. 60/480,928, also filed 23 Jun. 2003, U.S. provisional patent application No. 60/512,018, filed Oct. 17, 2003, and U.S. application Ser. No. 10/871,512, filed Jun. 18, 2004, all entitled Methods and Compositions for the Treatment of Amyloid- and Epileptogenesis-Associated Diseases.

Unless otherwise stipulated, the chemical moieties herein may be substituted or unsubstituted. In some embodiments, the term "substituted" means that the moiety has substituents placed on the moiety other than hydrogen which allow the molecule to perform its intended function. Examples of substituents, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $—NH_2$), $(CR'R'')_{0-3}CN$ (e.g., $—CN$), $—NO_2$, halogen (e.g., $—F$, $—Cl$, $—Br$, or $—I$), $(CR'R'')_{0-3}C(halogen)_3$ (e.g., $—CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $—SO_3H$, $—OSO_3H$), $(CR'R'')_{0-3}O(CR'R'')_{0-3}H$ (e.g., $—CH_2OCH_3$ and $—OCH_3$), $(CR'R'')_{0-3}S(CR'R'')_{0-3}H$ (e.g., $—SH$ and $—SCH_3$), $(CR'R'')_{0-3}OH$ (e.g., $—OH$), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., $—CO_2H$), or $(CR'R'')0$-$3OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group. "Substituents" may also include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfate, sulfonato, sulfamoyl, sulfonamido, nitro, trifluoromethyl, azido, heterocyclyl, aralkyl, or an aromatic or heteroaromatic moiety.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" includes all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds.

In certain embodiments, a "substituent" may be selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

The term "amine" or "amino," as used herein, refers to an unsubstituted or substituted moiety of the formula $—NR^aR^b$, in which $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated. Thus, the term "alkylamino" as used herein means an alkyl group having an amino group attached thereto. Suitable alkylamino groups include groups having 1 to about 12 carbon atoms, for example,1 to about 6 carbon atoms. The term amino includes compounds or moieties in which a nitrogen atom is covalently bonded to at least one carbon or heteroatom. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group.

The term "aliphatic group" includes organic compounds characterized by straight or branched chains, typically having between 1 and 22 carbon atoms. Aliphatic groups include alkyl groups, alkenyl groups and alkynyl groups. The chains may be branched or cross-linked. Alkyl groups include saturated hydrocarbons having one or more carbon atoms, including straight-chain alkyl groups and branched-chain alkyl groups. The term "alicyclic group" includes closed ring structures of three or more carbon atoms. Alicyclic groups include cycloparaffins or naphthenes that are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include polycyclic rings, e.g., fused ring structures, and substituted alicyclic groups such as alkyl substituted alicyclic groups. "Polycyclyl" or "polycyclic group" includes two or more cyclic rings (e.g., cycloalkyls, cycloalkenyls, cycloalkynyls, aryls or heterocyclyls) in which one or more carbons are common to two adjoining rings, e.g., the rings are "fused rings" or spiro-rings. Rings that are joined through non-adjacent atoms are termed "bridged" rings.

As used herein, "alkyl" groups include saturated hydrocarbons having one or more carbon atoms, including straight-chain alkyl groups, e.g., methyl, ethyl, propyl, butyl, pentyl, hexyl, heptyl, octyl, nonyl, decyl, etc.; cyclic alkyl groups (or "cycloalkyl" or "alicyclic" or "carbocyclic" groups), e.g., cyclopropyl, cyclopentyl, cyclohexyl, cycloheptyl, cyclooctyl, etc.; branched-chain alkyl groups, e.g., isopropyl, tert-butyl, sec-butyl, isobutyl, etc.; and alkyl-substituted alkyl groups, e.g., alkyl-substituted cycloalkyl groups and cycloalkyl-substituted alkyl groups.

Accordingly, the invention relates to, for example, substituted or unsubstituted alkylsulfonic acids that are substituted or unsubstituted straight-chain alkylsulfonic acids, substituted or unsubstituted cycloalkylsulfonic acids, and substituted or unsubstituted branched-chain alkylsulfonic acids.

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more particularly, for example, 18 or fewer. Additionally, example cycloalkyl groups have from 4-10 carbon atoms in their ring structure, e.g., 4-7 carbon atoms in the ring structure.

The term "lower alkyl" refers to alkyl groups having from 1 to 8 carbons in the chain, and to cycloalkyl groups having from 3 to 8 carbons in the ring structure. Unless the number of carbons is otherwise specified, "lower" as in "lower alkyl," means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain),for example, methyl, ethyl, propyl, isopropyl, butyl, isobutyl, sec-butyl, and tert-butyl. Likewise, cycloalkyl groups may have from 3-8 carbon atoms in their ring structure, for example, 5 or 6 carbons in the ring structure. The term "C1-C6" as in "C1-C6 alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or aromatic (including heteroaromatic) groups.

The terms "alkenyl" and "alkynyl" refer to unsaturated aliphatic groups analogous to alkyls, including straight and branched chains, and cyclical structures, but which contain at least one double or triple bond respectively. Suitable alkenyl and alkynyl groups include groups having 2 to about 12 carbon atoms, preferably from 2 to about 6 carbon atoms.

Aryl groups may also be fused or bridged with alicyclic or heterocyclic rings which are not aromatic so as to form a polycycle (e.g., tetralin). Those aryl groups having heteroatoms in the ring structure may also be referred to as aryl heterocycles, heterocycles, heteroaryls, or heteroaromatics, which, for example, include any ring formed that incorporates a heteroatom or an atom that is not carbon. The ring may be saturated or unsaturated and may contain one or more double bonds. Examples of some heterocyclic groups include pyridyl, furanyl, thiophenyl, morpholinyl, and indolyl groups.

The term "heteroatom" includes atoms of any element other than carbon or hydrogen. Preferred heteroatoms are nitrogen, oxygen, sulfur and phosphorus. Heterocyclic groups also include closed ring structures in which one or more of the atoms in the ring is an element other than carbon, for example, nitrogen, sulfur, or oxygen. Heterocyclic groups may be saturated or unsaturated and heterocyclic groups such as pyrrole and furan may have aromatic character. They include fused ring structures such as quinoline and isoquinoline. Other examples of heterocyclic groups include pyridine and purine. Examples of heteroaromatic and heteroalicyclic groups may have 1 to 3 separate or fused rings with 3 to about 8 members per ring and one or more N, O, or S atoms, e.g., coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino, and pyrrolidinyl.

In addition, it should be understood that pharmaceutically acceptable salts of the compounds of the invention are also within the scope of the present invention.

Pharmaceutically Acceptable Salts

The invention also includes pharmaceutically acceptable salts of the compounds described herein. "Pharmaceutically acceptable" denotes compounds, materials, compositions, or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" include, for example, derivatives of compounds modified by making acid or base salts thereof, which are known by the skilled artisan and/or described further below, and elsewhere in the present application. Examples of pharmaceutically acceptable salts include mineral or organic acid salts of basic residues, such as amines; and alkali or organic salts of acidic residues, such as carboxylic acids. Pharmaceutically acceptable salts include conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid (See, e.g., Berge et al. (1977) "Pharmaceutical Salts", *J. Pharm. Sci.* 66, 1-19). Pharmaceutically acceptable salts may be synthesized from the parent compound, which contains a basic or acidic moiety, by conventional chemical methods. Generally, such salts may be prepared by reacting the free acid or base forms of these compounds with a stoichiometric amount of the appropriate base or acid in water or in an organic solvent, or in a mixture of the two.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein.

Moreover, the compounds of the invention or pharmaceutically acceptable salts thereof are generally administered to a subject in a pharmaceutical composition/formulation.

V. Pharmaceutical Compositions

The formulations of the invention may further include a pharmaceutically acceptable carrier. The term "pharmaceutically acceptable carrier" includes a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

In certain embodiments, active compounds of the invention are administered at a therapeutically effective dosage sufficient to inhibit amyloid deposition or treat or prevent amyloidosis in a subject. A "therapeutically effective dosage" preferably inhibits amyloid deposition by at least about 20%, e.g., by at least about 40%, e.g., by at least about 60%, e.g., or by at least about 80% relative to untreated subjects. The ability of a compound to inhibit amyloid deposition can be evaluated in an animal model system that may be predictive of efficacy in inhibiting amyloid deposition in human diseases. Alternatively, the ability of a compound to inhibit amyloid deposition can be evaluated by examining the ability of the compound to inhibit an interaction between an amyloidogenic protein and a basement membrane constituent, e.g., using a binding assay such as that described hereinbefore.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The term "subject" includes living organisms in which amyloidosis can occur, or which are susceptible to amyloid diseases, e.g., Alzheimer's disease, Down's syndrome, CAA, dialysis-related ($\beta_2$M) amyloidosis, secondary (AA) amyloidosis, primary (AL) amyloidosis, hereditary amyloidosis, diabetes, etc. Examples of subjects include humans, monkeys, cows, sheep, goats, dogs, and cats. The language "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, peking ducks, geese, and transgenic species thereof.

In certain embodiments of the invention, the subject is in need of treatment by the methods of the invention, and is selected for treatment based on this need. A subject in need of treatment is art-recognized, and includes subjects that have been identified as having a disease or disorder related to amyloid-deposition or amyloidosis, having a symptom of such a disease or disorder, or at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

Administration of the compositions of the present invention to a subject to be treated can be carried out using known procedures, at dosages and for periods of time effective to inhibit amyloid deposition in the subject. An effective amount of the sulfonate derivatized compound necessary to achieve a therapeutic effect may vary according to factors such as the amount of amyloid already deposited at the clinical site in the subject, the age, sex, and weight of the subject, and the ability of the sulfonate derivatized compound to inhibit amyloid deposition in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a sulfonate derivatized compound of the invention (e.g., 3-amino-1-propanesulfonic acid) is between 1 and 500 mg/kg of body weight/per day. One of ordinary skill in the art would be able to study the relevant factors and make the determination regarding the effective amount of the sulfonate derivatized compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, the time of administration, the rate of excretion of the particular compound being employed, the duration of the treatment, other drugs, compounds or materials used in combination with the particular compound employed, the age, sex, weight, condition, general health and prior medical history of the patient being treated, and like factors well known in the medical arts.

A medical doctor, e.g., physician or veterinarian, having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The regimen of administration can affect what constitutes an effective amount. The formulations can be administered to the subject either prior to or after the onset of amyloidosis. Further, several divided dosages, as well as staggered dosages, can be administered daily or sequentially, or the dose can be continuously infused, or can be a bolus injection. Further, the dosages of the formulations can be proportionally increased or decreased as indicated by the exigencies of the therapeutic or prophylactic situation.

In particular embodiments, it is especially advantageous to formulate compositions in dosage unit form for ease of administration and uniformity of dosage. Dosage unit form as used herein refers to physically discrete units suited as unitary dosages for the subjects to be treated; each unit containing a predetermined quantity of sulfonate derivatized compound calculated to produce the desired therapeutic effect in association with the required pharmaceutical carrier. The specification for the dosage unit forms of the invention are dictated by and directly dependent on (a) the unique characteristics of the sulfonate derivatized compound and the particular therapeutic effect to be achieved, and (b) the limitations inherent in the art of compounding/formulating such a sulfonate derivatized compound for the treatment of amyloid deposition in subjects.

The formulations described hereinbefore, can be incorporated into a pharmaceutical composition in an amount effective to inhibit amyloidosis in a pharmaceutically acceptable carrier.

In another embodiment, the present invention relates to pharmaceutical compositions comprising compounds according to any of the formulae recited herein, and/or any of the specifically recited compounds, e.g., compounds included in Tables 2, 3 and 4, for the treatment of an amyloid-related disease, as well as methods of manufacturing such pharmaceutical compositions.

The sulfonate derivatized compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

To administer the sulfonate derivatized compound by other than parenteral administration, it may be necessary to coat the compound with, or co-administer the compound with, a material to prevent its inactivation. For example, the sulfonate derivatized compound may be administered to a subject in an appropriate carrier, for example, liposomes, or a diluent. Pharmaceutically acceptable diluents include, for example, saline and aqueous buffer solutions. Liposomes include water-in-oil-in-water CGF emulsions as well as conventional liposomes (Strejan et al., (1984) J. Neuroimmunol. 7:27).

In one embodiment, the pharmaceutical compositions suitable for injectable use include sterile aqueous solutions (where water soluble) or dispersions and sterile powders for the extemporaneous preparation of sterile injectable solutions or dispersion. The composition must be sterile and must be fluid to the extent that easy syringability exists. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the sulfonate derivatized compound in the required amount in an appropriate solvent with one or a combination of ingredients enumerated above, as required, followed by filtered sterilization. Generally, dispersions are prepared by incorporating the sulfonate derivatized compound into a sterile carrier, which contains, for example, a basic dispersion medium and the required other ingredients from those enumerated above. In the case of sterile powders for the preparation of sterile injectable solutions, the preferred methods of preparation are vacuum drying and freeze-drying, which yield a powder of the active ingredient (i.e., the sulfonate derivatized compound) plus any additional desired ingredient from a previously sterile-filtered solution thereof.

The sulfonate derivatized compound can be orally administered, for example, with an inert diluent or an assimilable edible carrier. The sulfonate derivatized compound and other ingredients may also be enclosed in a hard or soft shell gelatin capsule, compressed into tablets, or incorporated directly into the subject's diet. For oral therapeutic administration, the sulfonate derivatized compound may be incorporated with excipients and used in the form of ingestible tablets, buccal tablets, troches, capsules, elixirs, suspensions, syrups, wafers, and the like. The percentage of the sulfonate derivatized compound in the compositions and preparations may, of course, be varied. The amount of the sulfonate derivatized compound in such therapeutically useful compositions is such that a suitable dosage is obtained.

The formulations suitable for oral administration may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The sulfonate derivatized compounds of the invention are effective when administered orally. Accordingly, in one embodiment, a preferred route of administration is oral administration. To administer the sulfonate derivatized compound it may be necessary to coat the compound with, or co-administer the compound with, a material to prevent its inactivation. For example, the therapeutically active compound may be coated in a material to protect the compound from the action of acids and other natural conditions that may inactivate the compound.

The compounds of the invention may be formulated to ensure proper distribution in vivo. Liposomes include water-in-oil-in-water CGF emulsions as well as conventional liposomes (Strejan et al., (1984) J Neuroimmunol. 7:27). For example, the blood-brain barrier (BBB) excludes many highly hydrophilic compounds; and to ensure that the sulfonate derivatized compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al., (1995) FEBS Lett. 357:140; M. Owais et al., (1995) Antimicrob. Agents Chemother. 39:180); surfactant protein A receptor (Briscoe et al., (1995) Am. J. Physiol. 1233:134); gp120 (Schreier et aL.,(1994) J. Biol. Chem. 269:9090); see also K. Keinanen; M. L. Laukkanen (1994) FEBS Lett. 346:123; J. J. Killion; I. J. Fidler (1994) Immunomethods 4:273.

In specific embodiments of the invention, the sulfonate derivatized compound is administered with an agent selected from the group consisting of an agent that modifies the release of the sulfonate derivatized compound, e.g., hydroxypropylmethylcellulose (HPMG), a glidant/diluent, e.g., silicated mycrocrystalline, a filler, e.g., dibasic calcium phosphate, a binder/desintegrant, e.g., Starch 1500, a lubricant, e.g., stearic acid powder or magnesium stearate, a subcoat, e.g., Opadry II White, a topcoat, e.g., Opadry II White or Opadry Clear, an enteric coat, e.g., Acryleze, and any combination thereof. Several embodiments of the invention are discussed in U.S. provisional patent application No. 60/480,984, filed Jun. 23, 2003, U.S. provisional patent application No. 60/512,116, filed Oct. 17, 2003, both entitled, and U.S. application Ser. No. 10/871,549, filed Jun. 18, 2004, entitled Pharmaceutical Formulations of Amyloid-Inhibiting Compounds.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Powders can contain, in addition to a compound of this invention, excipients such as lactose, talc, silicic acid, aluminum hydroxide, calcium silicates and polyamide powder, or mixtures of these substances.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of sulfonate derivatized compound calculated to produce the desired therapeutic effect in association with the required pharmaceutical carrier. The specification for the dosage unit forms of the invention are dictated by and directly dependent on (a) the unique characteristics of the sulfonate derivatized compound and the particular therapeutic effect to be achieved, and (b) the limitations inherent in the art of compounding such a sulfonate derivatized compound for the treatment of amyloid deposition in subjects.

The present invention therefore includes pharmaceutical formulations comprising the compounds of the Formulae described herein, including pharmaceutically acceptable salts thereof, in pharmaceutically acceptable carriers for aerosol, oral and parenteral administration. Also, the present invention includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, a compound of the Formulae described herein, and pharmaceutically acceptable salts thereof, may be administered orally or through inhalation as a solid, or may be administered intramuscularly or intravenously as a solution, suspension or emulsion. Alternatively, the compounds or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired compound of any Formula herein, or a salt thereof, or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of any Formula described herein, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of any Formula described herein, or a salt thereof, in a carrier that comprises water. A surfactant may be present that lowers the surface tension of the formulation sufficiently to result in the formation of droplets within the desired size range when subjected to nebulization.

Peroral compositions also include liquid solutions, emulsions, suspensions, and the like. The pharmaceutically acceptable carriers suitable for preparation of such compositions are well known in the art. Typical components of carriers for syrups, elixirs, emulsions, and suspensions include ethanol, glycerol, propylene glycol, polyethylene glycol, liquid sucrose, sorbitol, and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise an effective amount, usually at least about 0.1%, and preferably from about 1% to about 5%, of a compound of the invention. Suitable carriers for topical administration preferably remain in place on the skin as a continuous film, and resist being removed by perspiration or immersion in water. Generally, the carrier is organic in nature and capable of having dispersed or dissolved therein the therapeutic compound. The carrier may include pharmaceutically acceptable emollients, emulsifiers, thickening agents, solvents and the like.

Blood-Brain Barrier

The compounds of the invention can also be formulated to ensure proper distribution in vivo. For example, the blood-brain barrier (BBB) excludes many highly hydrophilic compounds. To ensure that the more hydrophilic sulfonate derivatized compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) J. Clin. Pharmacol. 29:685).

Exemplary targeting moieties include folate or biotin (see, e.g., U.S. Pat. No. 5,416,016 to Low et al.); mannosides (Umezawa et al. (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); gp120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In a preferred embodiment, the sulfonate derivatized compounds of the invention are formulated in liposomes; in a more preferred embodiment, the liposomes include a targeting moiety.

To ensure that compounds of the invention cross the BBB, they may be coupled to a BBB transport vector (for review of BBB transport vectors and mechanisms, see Bickel, et al., *Adv. Drug Delivery Reviews*, vol. 46, pp. 247-279, 2001). Exemplary transport vectors include cationized albumin or the OX26 monoclonal antibody to the transferrin receptor; these proteins undergo absorptive-mediated and receptor-mediated transcytosis through the BBB, respectively.

Examples of other BBB transport vectors that target receptor-mediated transport systems into the brain include factors such as insulin, insulin-like growth factors (IGF-I, IGF-II), angiotensin II, atrial and brain natriuretic peptide (ANP, BNP), interleukin I (IL-1) and transferrin. Monoclonal antibodies to the receptors which bind these factors may also be used as BBB transport vectors. BBB transport vectors targeting mechanisms for absorptive-mediated transcytosis include cationic moieties such as cationized LDL, albumin or horseradish peroxidase coupled with polylysine, cationized albumin or cationized immunoglobulins. Small basic oligopeptides such as the dynorphin analogue E-2078 and the ACTH analogue ebiratide can also cross the brain via absorptive-mediated transcytosis and are potential transport vectors.

Other BBB transport vectors target systems for transporting nutrients into the brain. Examples of such BBB transport vectors include hexose moieties, e.g. glucose, monocarboxylic acids, e.g. lactic acid, neutral amino acids, e.g. phenylalanine, amines, e.g. choline, basic amino acids, e.g. arginine, nucleosides, e.g. adenosine, purine bases, e.g. adenine, and thyroid hormone, e.g. triiodothyridine. Antibodies to the extracellular domain of nutrient transporters can also be used as transport vectors. Other possible vectors include angiotensin II and ANP, which may be involved in regulating BBB permeability.

In some cases, the bond linking the sulfonate derivatized compound to the transport vector may be cleaved following transport into the brain in order to liberate the biologically active compound. Exemplary linkers include disulfide bonds, ester-based linkages, thioether linkages, amide bonds, acid-labile linkages, and Schiff base linkages. Avidin/biotin linkers, in which avidin is covalently coupled to the BBB drug transport vector, may also be used. Avidin itself may also be a drug transport vector.

In certain embodiments, the methods of the invention are useful for treating amyloidosis associated with any disease in which amyloid deposition occurs. Clinically, amyloidosis can be primary, secondary, familial or isolated. Moreover, amyloids have been categorized by the type of amyloidogenic protein contained within the amyloid.

VI. Amyloid-Related Diseases

In one embodiment, the sulfonate derivatized compounds prepared by the methods of the present invention have use in pharmaceutical compositions useful in the treatment of amyloid-related diseases. Many amyloid-related diseases are known, and others doubtless exist.

AA (Reactive) Amyloidosis

Generally, AA amyloidosis is a manifestation of a number of diseases that provoke a sustained acute phase response. Such diseases include chronic inflammatory disorders, chronic local or systemic microbial infections, and malignant neoplasms. The most common form of reactive or secondary (AA) amyloidosis is seen as the result of long-standing inflammatory conditions. For example, patients with Rheumatoid Arthritis or Familial Mediterranean Fever (which is a genetic disease) can develop AA amyloidosis. The terms "AA amyloidosis" and "secondary (AA) amyloidosis" are used interchangeably.

AA fibrils are generally composed of 8,000 Dalton fragments (AA peptide or protein) formed by proteolytic cleavage of serum amyloid A protein (ApoSAA), a circulating apolipoprotein which is mainly synthesized in hepatocytes in response to such cytokines as IL-1, IL-6 and TNF. Once secreted, ApoSAA is complexed with HDL. Deposition of AA fibrils can be widespread in the body, with a preference for parenchymal organs. The kidneys are usually a deposition site, and the liver and the spleen may also be affected. Deposition is also seen in the heart, gastrointestinal tract, and the skin.

Underlying diseases which can lead to the development of AA amyloidosis include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia. Other underlying conditions that may be associated with AA amyloidosis are Castleman's disease and Schnitzler's syndrome.

AL Amyloidoses (Primary Amyloidosis)

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia. AL amyloidosis is also described in detail in *Current Drug Targets*, 2004, 5 159-171.

Fibrils of AL amyloid deposits are composed of monoclonal immunoglobulin light chains or fragments thereof. More specifically, the fragments are derived from the N-terminal region of the light chain (kappa or lambda) and contain all or part of the variable ($V_L$) domain thereof. Deposits generally occur in the mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. However, it should be noted that almost any tissue, particularly visceral organs such as the kidney, liver, spleen and heart, may be involved.

Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 1 summarizes the fibril composition of exemplary forms of these disorders.

Transthyretin (TTR) is a 14 kiloDalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amy-

TABLE 1

Fibril Composition of Exemplary Amyloid-Related Diseases

| Fibril Peptide/Protein | Genetic Variant | Clinical Syndrome |
|---|---|---|
| ATTR protein from Transthyretin and fragments | Met30, many others | Familial amyloid polyneuropathy (FAP), (Mainly peripheral nerves) |
| ATTR protein from Transthyretin and fragments | Thr45, Ala60, Ser84, Met111, Ile122 | Cardiac involvement predominant without neuropathy, familial amyloid polyneuropathy, senile systemic amyloidosis, Tenosynovium |
| N-terminal fragment of Apolipoprotein A1 (apoAI) | Arg26 | Familial amyloid polyneuropathy (FAP), (mainly peripheral nerves) |
| N-terminal fragment of Apoliproprotein A1 (AapoAI) | Arg26, Arg50, Arg 60, others | Ostertag-type, non-neuropathic (predominantly visceral involvement) |
| AapoAII from Apolipoprotein AII | | Familial amyloidosis |
| Lysozyme (Alys) | Thr56, His67 | Ostertag-type, non-neuropathic (predominantly visceral involvement) |
| Fibrogen alpha chain fragment | Leu554, Val526 | Cranial neuropathy with lattic corneal dystrophy |
| Gelsolin fragment (Agel) | Asn187, Tyr187 | Cranial neuropathy with lattice corneal dystrophy |
| Cystatin C fragment (ACys) | Glu68 | Hereditary cerebral hemorrhage (cerebral amyloid angiopathy) - Icelandic type |
| β-amyloid protein (Aβ) derived from Amyloid Precursor Protein (APP) | Gln693 | Hereditary cerebral hemorrhage (cerebral amyloid angiopathy) - Dutch type |
| β-amyloid protein (Aβ) derived from Amyloid Precursor Protein (APP) | Ile717, Phe717, Gly717 | Familial Alzheimer's Disease |
| β-amyloid protein (Aβ) derived from Amyloid Precursor Protein (APP), e.g., bPP 695 | Gln 618 | Alzheimer's disease, Down's syndrome, hereditary cerebral hemorrhage with amyloidosis, Dutch type |
| β-amyloid protein (Aβ) derived from Amyloid Precursor Protein (APP) | Asn670, Leu671 | Familial Dementia - probably Alzheimer's Disease |
| Prion Protein (PrP, APrP$^{SC}$) derived from Prp precursor protein (51–91 insert) | Leu102, Val167, Asn178, Lys200 | Familial Creutzfeldt-Jakob disease; Gerstmann-Sträussler-Scheinker syndrome (hereditary spongiform encephalopathies, prion diseases) |
| AA derived from Serum amyloid A protein (ApoSAA) | | Familial Mediterranean fever, predominant renal involvement (autosomal recessive) |
| AA derived from Serum amyloid A protein (ApoSAA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |
| AH amyloid protein, derived from immunoglobulin heavy chain (gamma I) | AγI | Myeloma associated amyloidosis |
| ACal amyloid protein from (pro)calcitonin | (Pro) calcitonin | Medullary carcinomas of the thyroid |
| AANF amyloid protein from atrial natriuretic factor | | Isolated atrial amyloid |
| Apro from Prolactin | | Prolactinomas |
| Abri/ADan from ABri peptide | | British and Danish familial Dementia |

Data derived from Tan SY, Pepys MB. Amyloidosis. Histopathology, 25(5), 403–414 (November 1994), WHO/IUIS Nomenclature Subcommittee, Nomenclature of Amyloid and Amyloidosis. Bulletin of the World Health Organisation 1993; 71: 10508; and Merlini et al., Clin Chem Lab Med 2001; 39(11): 1065–75.

The data provided in Table 1 are exemplary and are not intended to limit the scope of the invention. For example, more than 40 separate point mutations in the transthyretin gene have been described, all of which give rise to clinically similar forms of familial amyloid polyneuropathy.

In general, any hereditary amyloid disorder can also occur sporadically, and both hereditary and sporadic forms of a disease present with the same characteristics with regard to amyloid. For example, the most prevalent form of secondary AA amyloidosis occurs sporadically, e.g. as a result of ongoing inflammation, and is not associated with Familial Mediterranean Fever. Thus general discussion relating to hereditary amyloid disorders below can also be applied to sporadic amyloidoses.

loid polyneuropathy. For example, substitution of proline for leucine at position 55 results in a particularly progressive form of neuropathy; substitution of methionine for leucine at position 111 resulted in a severe cardiopathy in Danish patients.

Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art (e.g., Gustavsson, A., et al., Laboratory Invest. 73: 703–708, 1995; Kametani, F., et al., Biochem. Biophys. Res. Commun. 125: 622-628, 1984; Pras, M., et al., PNAS 80: 539-42, 1983).

Persons having point mutations in the molecule apolipoprotein AI (e.g., Gly→Arg26; Trp→Arg50; Leu→Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199: 104-131, 1996).

Immunoglobulin light chains tend to form aggregates in various morphologies, including fibrillar (e.g., AL amyloidosis and AH amyloidosis), granular (e.g., light chain deposition disease (LCDD), heavy chain deposition disease (HCDD), and light-heavy chain deposition disease (LHCDD)), crystalline (e.g., Acquired Farconi's Syndome), and microtubular (e.g., Cryoglobulinemia). AL and AH amyloidosis is indicated by the formation of insoluble fibrils of immunoglobulin light chains and heavy chain, respectively, and/or their fragments. In AL fibrils, lambda ($\lambda$) chains such as $\lambda$VI chains ($\lambda$6 chains), are found in greater concentrations than kappa ($\kappa$) chains. $\lambda$III chains are also slightly elevated. Merlini et al., CLIN CHEM LAB MED 39(11):1065-75 (2001). Heavy chain amyloidosis (AH) is generally characterized by aggregates of gamma chain amyloid proteins of the IgG1 subclass. Eulitz et al., PROC NATL ACAD SCI USA 87:6542-46 (1990).

Comparison of amyloidogenic to non-amyloidogenic light chains has revealed that the former can include replacements or substitutions that appear to destabilize the folding of the protein and promote aggregation. AL and LCDD have been distinguished from other amyloid diseases due to their relatively small population monoclonal light chains, or fragments thereof, which are manufactured by neoplastic expansion of an antibody-producing B cell. AL aggregates typically are well-ordered fibrils of lambda chains. LCDD aggregates are relatively amorphous aggregations of both kappa and lambda chains, with a majority being kappa, in some cases $\kappa$IV. Bellotti et al., JOURNAL OF STRUCTURAL BIOLOGY 13:280-89 (2000). Comparison of amyloidogenic and non-amyloidogenic heavy chains in patients having AH amyloidosis has revealed missing and/or altered components. Eulitz et al., PROC NATL ACAD SCI USA 87:6542-46 (1990) (pathogenic heavy chain characterized by significantly lower molecular mass than non-amyloidogenic heavy chains); and Solomon et al. AM J HEMAT 45(2) 171-6 (1994) (amyloidogenic heavy chain characterized as consisting solely of the VH-D portion of the non-amyloidogenic heavy chain).

Accordingly, potential methods of detecting and monitoring treatment of subjects having or at risk of having AL, LCDD, AH, and the like, include but are not limited to immunoassaying plasma or urine for the presence or depressed deposition of amyloidogenic light or heavy chains, e.g., amyloid $\lambda$, amyloid $\kappa$, amyloid $\kappa$IV, amyloid $\gamma$, or amyloid $\gamma$1.

Brain Amyloidosis

The most frequent type of amyloid in the brain is composed primarily of A$\beta$ peptide fibrils, resulting in dementia associated with sporadic (non-hereditary) Alzheimer's disease. In fact, the incidence of sporadic Alzheimer's disease greatly exceeds forms shown to be hereditary. Nevertheless, fibril peptides forming plaques are very similar in both types. Brain amyloidosis includes those diseases, conditions, pathologies, and other abnormalities of the structure or function of the brain, including components thereof, in which the causative agent is amyloid. The area of the brain affected in an amyloid-related disease may be the stroma including the vasculature or the parenchyma including functional or anatomical regions, or neurons themselves. A subject need not have received a definitive diagnosis of a specifically recognized amyloid-related disease. The term "amyloid-related disease" includes brain amyloidosis.

Amyloid-$\beta$ peptide ("A$\beta$") is a 39-43 amino acid peptide derived by proteolysis from a large protein known as Beta Amyloid Precursor Protein ("$\beta$APP"). Mutations in $\beta$APP result in familial forms of Alzheimer's disease, Down's syndrome, cerebral amyloid angiopathy, and senile dementia, characterized by cerebral deposition of plaques composed of A$\beta$ fibrils and other components, which are described in further detail below. Known mutations in APP associated with Alzheimer's disease occur proximate to the cleavage sites of $\beta$ or $\gamma$-secretase, or within A$\beta$. For example, position 717 is proximate to the site of gamma-secretase cleavage of APP in its processing to A$\beta$, and positions 670/671 are proximate to the site of $\beta$-secretase cleavage. Mutations at any of these residues may result in Alzheimer's disease, presumably by causing an increase in the amount of the 42/43 amino acid form of A$\beta$ generated from APP. The familial form of Alzheimer's disease represents only 10% of the subject population. Most occurrences of Alzheimer's disease are sporadic cases where APP and A$\beta$ do not possess any mutation. The structure and sequence of A$\beta$ peptides of various lengths are well known in the art. Such peptides can be made according to methods known in the art, or extracted from the brain according to known methods (e.g., Glenner and Wong, Biochem. Biophys. Res. Comm. 129, 885-90 (1984); Glenner and Wong, Biochem. Biophys. Res. Comm. 122, 1131-35 (1984)). In addition, various forms of the peptides are commercially available. APP is expressed and constitutively catabolized in most cells. The dominant catabolic pathway appears to be cleavage of APP within the A$\beta$ sequence by an enzyme provisionally termed $\alpha$-secretase, leading to release of a soluble ectodomain fragment known as APPs$\alpha$. This cleavage precludes the formation of A$\beta$ peptide. In contrast to this non-amyloidogenic pathway, APP can also be cleaved by enzymes known as $\beta$- and $\gamma$-secretase at the N- and C-termini of the A$\beta$, respectively, followed by release of A$\beta$ into the extracellular space. To date, BACE has been identified as $\beta$-secretase (Vasser, et al., Science 286: 735-741, 1999) and presenilins have been implicated in $\gamma$-secretase activity (De Strooper, et al., Nature 391, 387-90 (1998)). The 39-43 amino acid A$\beta$ peptide is produced by sequential proteolytic cleavage of the amyloid precursor protein (APP) by the $\beta$ and $\gamma$ secretases enzyme. Although A$\beta$40 is the predominant form produced, 5-7% of total A$\beta$ exists as A$\beta$42 (Cappai et al., Int. J. Biochem. Cell Biol. 31. 885-89 (1999)).

The length of the A$\beta$ peptide appears to dramatically alter its biochemical/biophysical properties. Specifically, the additional two amino acids at the C-terminus of A$\beta$42 are very hydrophobic, presumably increasing the propensity of A$\beta$42 to aggregate. For example, Jarrett, et al. demonstrated that Aβ42 aggregates very rapidly in vitro compared to Aβ40, suggesting that the longer forms of Aβ may be the important pathological proteins that are involved in the initial seeding of the neuritic plaques in Alzheimer's disease (Jarrett, et al., *Biochemistry* 32, 4693-97 (1993); Jarrett, et al., *Ann. N.Y. Acad. Sci.* 695, 144-48 (1993)). This hypothesis has been further substantiated by the recent analysis of the contributions of specific forms of Aβ in cases of genetic familial forms of Alzheimer's disease ("FAD"). For example, the "London" mutant form of APP (APPV717I) linked to FAD selectively increases the production of Aβ 42/43 forms versus Aβ 40 (Suzuki, et al., *Science* 264, 1336-40 (1994)) while the "Swedish" mutant form of APP (APPK670N/M671L) increases levels of both Aβ40 and Aβ42/43 (Citron, et al., *Nature* 360, 672-674 (1992); Cai, et al., *Science* 259, 514-16, (1993)). Also, it has been observed that FAD-linked mutations in the Presenilin-1 ("PS1") or Presenilin-2 ("PS2") genes will lead to a selective increase in Aβ42/43 production but not Aβ40 (Borchelt, et al., *Neuron* 17, 1005-13 (1996)). This finding was corroborated in transgenic mouse models expressing PS mutants that demonstrate a selective increase in brain Aβ42 (Borchelt, op cit.; Duff, et al., *Neurodegeneration* 5(4), 293-98 (1996)). Thus the leading hypothesis regarding the etiology of Alzheimer's disease is that an increase in Aβ42 brain concentration due to an increased production and release of Aβ42 or a decrease in clearance (degradation or brain clearance) is a causative event in the disease pathology.

Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ; the Italian mutation of Aβ; the Iowa mutation of Aβ; familial British dementia; and familial Danish dementia. CAA may also be sporadic.

As used herein, the terms "β amyloid," "amyloid-β," and the like refer to amyloid β proteins or peptides, amyloid β precursor proteins or peptides, intermediates, and modifications and fragments thereof, unless otherwise specifically indicated. In particular, "Aβ" refers to any peptide produced by proteolytic processing of the APP gene product, especially peptides which are associated with amyloid pathologies, including Aβ1-39, Aβ1-40, Aβ1-41, Aβ1-42, and Aβ1-43. For convenience of nomenclature, "Aβ1-42" may be referred to herein as "Aβ(1-42)" or simply as "Aβ42" or "Aβ$_{42}$" (and likewise for any other amyloid peptides discussed herein). As used herein, the terms "β amyloid," "amyloid-β," and are synonymous.

Unless otherwise specified, the term "amyloid" refers to amyloidogenic proteins, peptides, or fragments thereof which can be soluble (e.g., monomeric or oligomeric) or insoluble (e.g., having fibrillary structure or in amyloid plaque). See, e.g., M P Lambert, et al., Proc. Nat'l Acad. Sci. USA 95, 6448-53 (1998). "Amyloidosis" or "amyloid disease" or "amyloid-related disease" refers to a pathological condition characterized by the presence of amyloid fibers. "Amyloid" is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Gelsolin is a calcium binding protein that binds to fragments and actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173-243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al. Human Mol. Genet. 5(9): 1237-1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland (Isselbacher, Harrison's Principles of Internal Medicine, McGraw-Hill, San Francisco, 1995; Benson, et al.). In at least some cases, patients with cerebral amyloid angiopathy (CAA) have been shown to have amyloid fibrils containing a non-mutant form of cystatin C in conjunction with amyloid beta protein (Nagai, A., et al. Molec. Chem. Neuropathol. 33: 63-78, 1998).

Certain forms of prion disease are now considered to be heritable, accounting for up to 15% of cases, which were previously thought to be predominantly infectious in nature. (Baldwin, et al., in Research Advances in *Alzheimer's Disease and Related Disorders*, John Wiley and Sons, New York, 1995). In hereditary and sporadic prion disorders, patients develop plaques composed of abnormal isoforms of the normal prion protein (PrP$^{Sc}$).

A predominant mutant isoform, PrP$^{Sc}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Sträussler-Scheinker syndrome (GSS), and fatal familial insomnia (FFI). (Baldwin, supra) Methods for extracting fibril peptides from scrapie fibrils, determining sequences and making such peptides are known in the art (e.g., Beekes, M., et al. J. Gen. Virol. 76: 2567-76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. The most common occurrences of cerebral amyloidosis are sporadic and not familial. For example, the incidence of sporadic Alzheimer's disease and sporadic CAA greatly exceeds the incidence of familial AD and CAA. Moreover, sporadic and familial forms of the disease cannot be distinguished from each other (they differ only in the presence or absence of an inherited genetic mutation); for example, the clinical symptoms and the amyloid plaques formed in both sporadic and familial AD are very similar, if not identical.

Cerebral amyloid angiopathy (CAA) refers to the specific deposition of amyloid fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)). CAA can occur sporadically or be hereditary.

Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate ($β_2$ microglobulin), joints and seminal vesicles.

Dialysis-related Amyloidosis (DRA)

Plaques composed of $β_2$ microglobulin ($β_2$M) fibrils commonly develop in patients receiving long term hemodialysis or peritoneal dialysis. $β_2$ microglobulin is a 11.8 kiloDalton polypeptide and is the light chain of Class I MHC antigens, which are present on all nucleated cells. Under normal circumstances, $β_2$M is usually distributed in the extracellular space unless there is an impaired renal function, in which case $β_2$M is transported into tissues where it polymerizes to form amyloid fibrils. Failure of clearance such as in the case of impaired renal function, leads to deposition in the carpal tunnel and other sites (primarily in collagen-rich tissues of the joints). Unlike other fibril proteins, $β_2$M molecules are not produced by cleavage of a longer precursor protein and are generally present in unfragmented form in the fibrils. (Benson, supra). Retention and accumulation of this amyloid precursor has been shown to be the main pathogenic process underlying DRA. DRA is characterized by peripheral joint osteoarthropathy (e.g., joint stiffness, pain, swelling, etc.). Isoforms of $β_2$M, glycated $β_2$M, or polymers of $β_2$M in tissue are the most amyloidogenic form (as opposed to native $β_2$M). Unlike other types of amyloidosis, $β_2$M is confined largely to osteoarticular sites. Visceral depositions are rare. Occasionally, these deposits may involve blood vessels and other important anatomic sites.

Despite improved dialysis methods for removal of $β_2$M, the majority of patients have plasmatic $β_2$M concentrations that remain dramatically higher than normal. These elevated $β_2$M concentrations generally lead to Diabetes-Related Amyloidosis (DRA) and cormorbidities that contribute to mortality.

Islet Amyloid Polypeptide and Diabetes

Islet hyalinosis (amyloid deposition) was first described over a century ago as the presence of fibrous protein aggregates in the pancreas of patients with severe hyperglycemia (Opie, E L., *J Exp. Med*. 5: 397-428, 1901). Today, islet amyloid, composed predominantly of islet amyloid polypeptide (IAPP), or amylin, is a characteristic histopathological marker in over 90% of all cases of Type II diabetes (also known as Non-Insulin Dependent Diabetes, or NIDDM). These fibrillar accumulations result from the aggregation of the islet amyloid polypeptide (IAPP) or amylin, which is a 37 amino acid peptide, derived from a larger precursor peptide, called pro-IAPP.

IAPP is co-secreted with insulin in response to β-cell secretagogues. This pathological feature is not associated with insulin-dependent (Type I) diabetes and is a unifying characteristic for the heterogeneous clinical phenotypes diagnosed as NIDDM (Type II diabetes).

Longitudinal studies in cats and immunocytochemical investigations in monkeys have shown that a progressive increase in islet amyloid is associated with a dramatic decrease in the population of insulin-secreting β-cells and increased severity of the disease. More recently, transgenic studies have strengthened the relationship between IAPP plaque formation and β-cell apoptosis and dysfunction, indicating that amyloid deposition is a principal factor in increasing severity of Type II diabetes.

IAPP has also been shown to induce β-islet cell toxicity in vitro, indicating that appearance of IAPP fibrils in the pancreas of Type II or Type I diabetic patients (post-islet transplantation) could contribute to the loss of the β-cell islets (Langerhans) and organ dysfunction. In patients with Type II diabetes, the accumulation of pancreatic IAPP leads to formation of oligomeric IAPP, leading to a buildup of IAPP-amyloid as insoluble fibrous deposits which eventually destroys the insulin-producing β cells of the islet, resulting in β cell depletion and failure (Westermark, P., Grimelius, L., *Acta Path. Microbiol. Scand., sect. A*. 81: 291-300, 1973; de Koning, E J P., et al., *Diabetologia* 36: 378-384, 1993; and Lorenzo, A., et al., *Nature* 368: 756-760, 1994). Accumulation of IAPP as fibrous deposits can also have an impact on the ratio of pro-IAPP to IAPP normally found in plasma by increasing this ratio due to the trapping of IAPP in deposits. Reduction of β cell mass can be manifested by hyperglycemia and insulinemia. This β-cell mass loss can lead to a need for insulin therapy.

Diseases caused by the death or malfunctioning of a particular type or types of cells can be treated by transplanting into the patient healthy cells of the relevant type of cell. This approach has been used for Type I diabetes patients. Often pancreatic islet cells from a donor are cultured in vitro prior to transplantation, to allow them to recover after the isolation procedure or to reduce their immunogenicity. However, in many instances islet cell transplantation is unsuccessful, due to death of the transplanted cells. One reason for this poor success rate is IAPP, which organizes into toxic oligomers. Toxic effects may result from intracellular and extracellular accumulation of fibril oligomers. The IAPP oligomers can form fibrils and become toxic to the cells in vitro. In addition, IAPP fibrils are likely to continue to grow after the cells are transplanted and cause death or dysfunction of the cells. This may occur even when the cells are from a healthy donor and the patient receiving the transplant does not have a disease that is characterized by the presence of fibrils. For example, compounds of the present invention may also be used in preparing tissues or cells for transplantation according to the methods described in International Patent Application (PCT) number WO 01/003680.

The compounds of the invention may also stabilize the ratio of the concentrations of Pro-IAPP/IAPP, pro-Insulin/Insulin and C-peptide levels. In addition, as biological markers of efficacy, the results of the different tests, such as the arginine-insulin secretion test, the glucose tolerance test, insulin tolerance and sensitivity tests, could all be used as markers of reduced β-cell mass and/or accumulation of amyloid deposits. Such class of drugs could be used together with other drugs targeting insulin resistance, hepatic glucose production, and insulin secretion. Such compounds might prevent insulin therapy by preserving β-cell function and be applicable to preserving islet transplants.

Hormone-derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), and atrial natriuretic peptide (isolated atrial amyloidosis). Sequences and structures of these proteins are well known in the art.

Miscellaneous Amyloidoses

There are a variety of other forms of amyloid disease that are normally manifest as localized deposits of amyloid. In general, these diseases are probably the result of the localized production or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid. Other amyloid-related diseases include those described in Table 1, such as familial amyloid polyneuropathy (FAP), senile systemic amyloidosis, Tenosynovium, familial amyloidosis, Ostertag-type, non-neuropathic amyloidosis, cranial neuropathy, hereditary cerebral hemorrhage, familial dementia, chronic dialysis, familial Creutzfeldt-Jakob disease; Gerstmann-Sträussler-Scheinker syndrome, hereditary spongiform encephalopathies, prion diseases, familial Mediterranean fever, Muckle-Well's syndrome, nephropathy, deafness, urticaria, limb pain, cardiomyopathy, cutaneous deposits, multiple myeloma, benign monoclonal gammopathy, maccoglobulinaemia, myeloma associated amyloidosis, medullary carcinomas of the thyroid, isolated atrial amyloid, and diabetes.

The compounds of the invention may be administered therapeutically or prophylactically to treat diseases associated with amyloid fibril formation, aggregation or deposition, regardless of the clinical setting. The compounds of the invention may act to ameliorate the course of an amyloid-related disease using any of the following mechanisms, such as, for example but not limited to: slowing the rate of amyloid fibril formation or deposition; lessening the degree of amyloid deposition; inhibiting, reducing, or preventing amyloid fibril formation; inhibiting amyloid induced inflammation; enhancing the clearance of amyloid from, for example, the brain; or protecting cells from amyloid induced (oligomers or fibrillar) toxicity.

In an embodiment, the compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; enhancing the clearance of amyloid-β from the brain; or favoring greater catabolism of Aβ.

Compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. In addition, compounds that penetrate the brain may control deposition by acting directly on brain Aβ, e.g., by maintaining it in a non-fibrillar form or favoring its clearance from the brain. The compounds may slow down APP processing; may increase degradation of Aβ fibrils by macrophages or by neuronal cells; or may decrease Aβ production by activated microglia. These compounds could also prevent Aβ in the brain from interacting with the cell surface and therefore prevent neurotoxicity, neurodegeneration, or inflammation.

In a preferred embodiment, the method is used to treat Alzheimer's disease (e.g., sporadic or familial AD). The method can also be used prophylactically or therapeutically to treat other clinical occurrences of amyloid-β deposition, such as in Down's syndrome individuals and in patients with cerebral amyloid angiopathy ("CAA"), hereditary cerebral hemorrhage, or early Alzheimer's disease.

In another embodiment, the method is used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, V., et al. (1996) *Proc. Natl. Acad. Sci. USA* 93: 1314-1319; Askanas, V. et al. (1995) *Current Opinion in Rheumatology* 7: 486-496). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., Proc. Natl. Acad. Sci. USA 99(18), 11830-5 (2002)).

In another embodiment, the invention also relates to a method of treating or preventing an amyloid-related disease in a subject (preferably a human) comprising administering to the subject a therapeutic amount of a compound according to the following Formulae or otherwise described herein, such that amyloid fibril formation or deposition, neurodegeneration, or cellular toxicity is reduced or inhibited. In another embodiment, the invention relates to a method of treating or preventing an amyloid-related disease in a subject (preferably a human) comprising administering to the subject a therapeutic amount of a compound according to the following Formulae or otherwise described herein, such that cognitive function is improved or stabilized or further deterioration in cognitive function is prevented, slowed, or stopped in patients with brain amyloidosis, e.g., Alzheimer's disease, Down's syndrome or cerebral amyloid angiopathy. These compounds can also improve quality of daily living in these subjects.

The therapeutic compounds of the invention may treat amyloidosis related to type II diabetes by, for example, stabilizing glycemia, preventing or reducing the loss of β cell mass, reducing or preventing hyperglycemia due to loss of β cell mass, and modulating (e.g., increasing or stabilizing) insulin production. The compounds of the invention may also stabilize the ratio of the concentrations of pro-IAPP/IAPP.

The therapeutic compounds of the invention may treat AA (secondary) amyloidosis and/or AL (primary) amyloidosis, by stabilizing renal function, decreasing proteinuria, increasing creatinine clearance (e.g., by at least 50% or greater or by at least 100% or greater), or by leading to remission of chronic diarrhea, or weight gain (e.g., 10% or greater).

The language "inhibition of amyloid deposition" includes reducing, preventing or stopping of amyloid formation, e.g., fibrillogenesis, inhibiting or slowing down of further amyloid deposition in a subject with amyloidosis, e.g., already having amyloid deposits, and reducing or reversing amyloid fibrillogenesis or deposits in a subject with ongoing amyloidosis. For example, the extent of the inhibition of amyloid deposition is contemplated by the instant application as a range, which can include, for example, substantially complete elimination of amyloid deposition or reduction of amyloid deposition. Inhibition of amyloid deposition is determined relative to an untreated subject, or relative to the treated subject prior to treatment, or, e.g., determined by clinically measurable improvement in pancreatic function in a diabetic patient, or in the case of a patient with brain amyloidosis, e.g., an Alzheimer's or cerebral amyloid angiopathy patient, stabilization of cognitive function or prevention of a further decrease in cognitive function (i.e., preventing, slowing, or stopping disease progression), or improvement of parameters such as the concentration of Aβ or tau in the CSF. In certain embodiments, amyloid deposition may be inhibited by, for example, inhibiting an interaction between an amyloidogenic protein and a constituent of basement membrane, enhancing clearance of amyloid β from the brain, or inhibiting neurodegeneration or cellular toxicity induced by amyloid (e.g., by soluble or insoluble amyloid, e.g., fibrils, by amyloid deposition and/or by amyloid-β, as described herein), or protecting brain cells from the detrimental effect of Aβ.

As used herein, "treatment" of a subject includes the application or administration of a composition of the invention to a subject, or application or administration of a composition of the invention to a cell or tissue from a subject, who has an amyloid-related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, ADAS-Cog, or another test known in the art. For example, the methods of the invention successfully treat a subject's dementia by slowing the rate of or lessening the extent of cognitive decline.

In one embodiment, the term "treating" includes maintaining a subject's CDR rating at its base line rating or at 0. In another embodiment, the term treating includes decreasing a subject's CDR rating by about 0.25 or more, about 0.5 or more, about 1.0 or more, about 1.5 or more, about 2.0 or more, about 2.5 or more, or about 3.0 or more. In another embodiment, the term "treating" also includes reducing the rate of the increase of a subject's CDR rating as compared to historical controls. In another embodiment, the term includes reducing the rate of increase of a subject's CDR rating by about 5% or more, about 10% or more, about 20% or more, about 25% or more, about 30% or more, about 40% or more, about 50% or more, about 60% or more, about 70% or more, about 80% or more, about 90% or more, or about 100%, of the increase of the historical or untreated controls.

In another embodiment, the term "treating" also includes maintaining a subject's score on the MMSE. The term "treating" includes increasing a subject's MMSE score by about 1, about 2, about 3, about 4, about 5, about 7.5, about 10, about 12.5, about 15, about 17.5, about 20, or about 25 points. The term also includes reducing the rate of the decrease of a subject's MMSE score as compared to historical controls. In another embodiment, the term includes reducing the rate of decrease of a subject's MMSE score may be about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In yet another embodiment, the term "treating" includes maintaining a subject's score on the ADAS-Cog. The term "treating" includes decreasing a subject's ADAS-Cog score by about 1 point or greater, by about 2 points or greater, by about 3 points or greater, by about 4 points or greater, by about 5 points or greater, by about 7.5 points or greater, by about 10 points or greater, by about 12.5 points or greater, by about 15 points or greater, by about 17.5 points or greater, by about 20 points or greater, or by about 25 points or greater. The term also includes reducing the rate of the increase of a subject's ADAS-Cog score as compared to historical controls. In another embodiment, the term includes reducing the rate of increase of a subject's ADAS-Cog score by about 5% or more, about 10% or more, about 20% or more, about 25% or more, about 30% or more, about 40% or more, about 50% or more, about 60% or more, about 70% or more, about 80% or more, about 90% or more or about 100% of the increase of the historical or untreated controls.

In another embodiment, the term "treating," for example, for AA or AL amyloidosis, includes an increase in serum creatinine clearance, e.g., an increase of creatinine clearance of 10% or greater, 20% or greater, 50% or greater, 80% or greater, 90% or greater, 100% or greater, 150% or greater, 200% or greater. The term "treating" also may include remission of nephrotic syndrome (NS). It may also include remission of chronic diarrhea and/or a gain in body weight, e.g., by 10% or greater, 15% or greater, or 20% or greater.

Without wishing to be bound by theory, in some aspects the pharmaceutical compositions of the invention contain a compound that prevents or inhibits amyloid fibril formation, either in the brain or other organ of interest (acting locally) or throughout the entire body (acting systemically). Pharmaceutical compositions of the invention may be effective in controlling amyloid deposition either following their entry into the brain (following penetration of the blood brain barrier) or from the periphery. When acting from the periphery, a compound of a pharmaceutical composition may alter the equilibrium of amyloidogenic peptide between the brain and the plasma to favor the exit of amyloidogenic peptide from the brain. It may also favor clearance (or catabolism) of the amyloid protein (soluble), and then prevent amyloid fibril formation and deposition due to a reduction of the amyloid protein pool in a specific organ, e.g., liver, spleen, pancreas, kidney, joints, brain, etc. An increase in the exit of amyloidogenic peptide from the brain would result in a decrease in amyloidogenic peptide brain concentration, and therefore, favor a decrease in amyloidogenic peptide deposition. In particular, an agent may lower the levels of amyloid β peptides, e.g., both Aβ40 and Aβ42 in the CSF and the plasma, or the agent may lower the levels of amyloid β peptides, e.g., Aβ40 and Aβ42 in the CSF and increase it in the plasma. Alternatively, compounds that penetrate the brain could control deposition by acting directly on brain amyloidogenic peptide e.g., by maintaining it in a non-fibrillar form or favoring its clearance from the brain, by increasing its degradation in the brain, or protecting brain cells from the detrimental effect of amyloidogenic peptide. An agent can also cause a decrease of the concentration of the amyloid protein (i.e., in a specific organ so that the critical concentration needed to trigger amyloid fibril formation or deposition is not reached). Furthermore, the compounds described herein may inhibit or reduce an interaction between amyloid and a cell surface constituent, for example, a glycosaminoglycan or proteoglycan constituent of a basement membrane. The compounds may also prevent an amyloid peptide from binding or adhering to a cell surface, a process that is known to cause cell damage or toxicity. Similarly, the compounds may block amyloid-induced cellular toxicity or microglial activation or amyloid-induced neurotoxicity, or inhibit amyloid induced inflammation. The compounds may also reduce the rate or amount of amyloid aggregation, fibril formation, or deposition, or the compounds may lessen the degree of amyloid deposition. The foregoing mechanisms of action should not be construed as limiting the scope of the invention inasmuch as the invention may be practiced without such information.

The language "basement membrane" refers to an extracellular matrix comprising glycoproteins and proteoglycans, including laminin, collagen type IV, fibronectin, agrin, perlecan, and heparan sulfate proteoglycan (HSPG). In one embodiment, amyloid deposition is inhibited by interfering with an interaction between an amyloidogenic protein and a sulfated glycosaminoglycan such as HSPG. Sulfated glycosaminoglycans are known to be present in all types of amyloids (see Snow, A. D., et al. Lab. Invest. 56, 120-123 (1987)) and amyloid deposition and HSPG deposition occur coincidentally in animal models of amyloidosis (see Snow, A. D., et al., Lab. Invest. 56, 665-675 (1987)). Consensus binding site motifs for HSPG in amyloidogenic proteins have been described, see, e.g., Cardin and Weintraub, Arteriosclerosis 9, 21-32 (1989).

In another embodiment, the therapeutic formulation is capable of inhibiting an interaction between an amyloidogenic protein and a glycoprotein or proteoglycan constituent of a basement membrane to thus inhibit amyloid deposition. The ability of a sulfonate derivatized compound of the invention to inhibit an interaction between an amyloidogenic protein and a glycoprotein or proteoglycan constituent of a basement membrane can be assessed by an in vitro binding assay, such as that described in the Exemplification or in U.S. Pat. No. 5,164,295 by Kisilevsky et al. Briefly, a solid support such as a polystyrene microtiter plate is coated with an amyloidogenic protein (e.g., serum amyloid A protein or β-amyloid precursor protein (β-APP)) and any residual hydrophobic surfaces are blocked. The coated solid support is incubated with various concentrations of a constituent of basement membrane, preferably HSPG, either in the presence or absence of a compound to be tested. The solid support is washed extensively to remove unbound material. The binding of the basement membrane constituent (e.g., HSPG) to the amyloidogenic protein (e.g., β-APP) is then measured using an antibody directed against the basement membrane constituent which is conjugated to a detectable substance (e.g., an enzyme, such as alkaline phosphatase) by detecting the detectable substance. A compound that inhibits an interaction between an amyloidogenic protein and a glycoprotein or proteoglycan constituent of a basement membrane will reduce the amount of substance detected (e.g., will inhibit the amount of enzyme activity detected).

Equivalents

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including reaction times, reaction size/volume, and experimental reagents, such as solvents, catalysts, pressures, atmospheric conditions, e.g., nitrogen atmosphere, and reducing/oxidizing agents, etc., with art-recognized alternatives and using no more than routine experimentation, are within the scope of the present application.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values that fall within these ranges, as well as the upper or lower limits of a range of values, are also contemplated by the present application.

Incorporation by Reference

The contents of all references, issued patents, and published patent applications cited throughout this application are hereby incorporated by reference. It should be understood that the use of any of the compounds described herein or in the applications identified in "The Related Applications" Section are within the scope of the present invention and are intended to be encompassed by the present invention and are expressly incorporated herein at least for these purposes, and are furthermore expressly incorporated for all other purposes

EXAMPLES

The invention is further illustrated by the following examples, which should not be construed as further limiting the subject invention. The following examples demonstrate the use of the methods of the invention in the preparation of a wide range of sulfonate derivatized compounds on small, large scale, and production scale. Particular examples of compounds prepared by the methods of the invention are shown below in Tables 2, 3, and 4. Further examples of compounds that may be prepared by the methods of the invention and further exemplification of specific experimental methods are described in U.S. provisional patent application No. 60/480,906, filed Jun. 23, 2003, and U.S. provisional patent application No. 60/512,047, filed Oct. 17, 2003, U.S. application Ser. No. 10/871,514, filed Jun. 18, 2004, and U.S. application Ser. No. 10/871,365, filed Jun. 18, 2004, all entitled *Methods and Compositions for Treating Amyloid-Related Diseases*, which are hereby expressly incorporated herein by reference in their entireties.

Example 1

Large Scale Synthesis of 1,3-propanedisulfonic acid disodium salt

To degassed water (550 mL) under a nitrogen atmosphere sodium sulfite (150 g. 1.19 mol) was loaded in one-portion. The mixture was stirred for 10 min. at room temperature. (In fact, effective stirring was applied throughout the entire reaction process.) After the dissolution of the sodium sulfite, the mixture was cooled to around 10° C. (internal temperature). To the cooled mixture was added a solution of 1,3-propane sultone (155 g, 1.27 mol) in acetone (100 mL) dropwise, or through a cannula over a 60-min. period. The rate of the addition was adjusted to maintain the internal temperature below 15° C.

The internal temperature was kept at a temperature below 15° C. for 15 min. after the completion of the addition, and then warmed to 15° C. The mixture was then stirred for 3 h at 15° C. The mixture was subsequently cooled to an internal temperature of 10° C. To the cold, stirred mixture, absolute ethanol (900 g, 1.1 L) was added through an addition funnel or a cannula over a period of 45-60 min. Moreover, the temperature was maintained below 15° C. during the ethanol addition.

The suspension was stirred for a minimum 2 h at 5° C. (internal temperature). The solid material was collected from the cold mixture by suction-filtration. The filter cake was washed with 90% ethanol (2×300 mL), and air-dried under reduced pressure for about 60 min. The air-dried filter-cake was dissolved in Millipore water (about 300 mL), such that the total weight of the filter cake and the water added did not exceed 770 g, (which required heating the mixture briefly to make sure a complete dissolution occurred). The pH of the solution was adjusted to 9-10 using 1 N sodium hydroxide.

The solution was filtered through filter-paper (or on-line filter). The filtrate was then stirred and cooled to 10° C. (internal temperature). To the stirred, cold mixture, absolute ethanol (980 g, 1.2 L) was added through an addition funnel or a cannula over a period of 60-90 min. The temperature was maintained below 15° C. during the addition period, and the suspension thus obtained was stirred at 5° C. (internal temperature) for a minimum 2 h after the completion of the ethanol addition. The solid material was collected from the cold mixture by suction-filtration. The filter cake was washed with cold (0° C.), 90% ethanol (2×300 mL), and air-dried under suction for 1 h. The air-dried filter cake was transferred to a clean container, broken into small piece, and dried in an vacuum oven (70° C., <2 mmHg) for 15-18 h. The final product was obtained as a white, crystalline solid, 260-262 g (90-91% yield): NMR ($^1$H, and $^{13}$C), MS (ESI$^-$), and FTIR conform to the structure; Br (% w/w), not detected (<0.1%); SO$_4^=$, <1%; 3-hydroxy-1-propanesulfonic acid, not detected (<0.1%); residual solvents (acetone, ethanol, toluene (if toluene-denatured ethanol used), not detected; water content, <1%; crystalline form, anhydrous; apparent density, 0.77±0.05 g/mL.

Example 2

Production Scale Synthesis of 1,3-propanedisulfonic acid disodium salt

To degassed water (550 kg) under a nitrogen atmosphere, sodium sulfite (150 kg) is loaded in one-portion. The mixture is then stirred for 30 min. at room temperature. Heating is applied if necessary to speed up the dissolution of the sodium sulfite. (Effective stirring is applied throughout the entire reaction process.) After the dissolution of the sodium sulfite, the mixture is cooled to around 10° C. (internal temperature). To the cooled mixture a solution of 1,3-propane sultone (155 kg) in acetone (100 L) is added over a 2 h period. The rate of the addition is adjusted to maintain the internal temperature below 15° C.

The internal temperature is kept at a temperature that is below 15° C. for 1 h after the completion of the addition, and then warmed to 15° C. The mixture is stirred for 3 to 5 h at 15° C., cooled to an internal temperature of 10° C., and absolute ethanol (900 kg) is added to the cold, stirring mixture, over a period of 1-2 h. The temperature is maintained below 15° C. during the ethanol addition. The suspension is stirred for a minimum of 2 h at 5° C. (internal temperature).

The solid material is collected from the cold mixture by suction-filtration. The filter cake is subsequently washed with 90% ethanol (2×300 L), and air-dried on the filter under a stream of nitrogen gas for about 1-2 h. The dried filter-cake is dissolved in Millipore water (about 300 kg) such that the total weight of the filter cake and the water added did not exceed 770 kg (which may require heating the mixture briefly to ensure complete dissolution). The pH of the solution is adjusted to 7-8 using 1 N sodium hydroxide. The solution is then filtered (e.g. using an on-line filter).

The filtrate is stirred and cooled to 10° C. (internal temperature). To the stirred, cold mixture absolute ethanol (980 kg) is added over a period of 1-2 h. The temperature is maintained below 15° C. during the addition period, and the suspension thus obtained is stirred at 5° C. (internal temperature) for a minimum 2 h after the completion of the ethanol addition. The solid material is collected from the cold mixture by filtration. The filter cake is washed with cold (0° C.), 90% ethanol (2×300 L), and dried on the filter under a stream of nitrogen gas for about 1 h. The dried filter cake is transferred to a vacuum oven (100° C., <2 mmHg) for 15-18 h. The final product is expected to be obtained as a white, crystalline solid, about 260 kg. The following specifications for the product are expected: (90-91% yield): NMR ($^1$H, and $^{13}$C), MS (ESI$^-$), and FTIR conform to the structure; Br (% w/w), not detectable (<0.1%); SO$_4^=$, <1%; 3-hydroxy-1-propanesulfonic acid, not detectable (<0.1%); residual solvents (acetone, ethanol, toluene (if toluene-denatured ethanol used), not detectable; water content, <1%; crystalline form, anhydrous; apparent density, 0.77±0.05 g/mL.

Example 3

Additional Synthetic Examples (1) Disulfonic Acid Derivatives (a) 1,4-Butanedisulfonic acid sodium salt: At room temperature sodium sulfite (9.16 g, 72.2 mmol) was added to degassed water (37 mL). Once the dissolution was complete, a solution of 1,4-butane sultone (10.38 g, 76.3 mmol) in acetone (22 mL) was added dropwise over a 5-min. period. The reaction mixture was stirred for 1 h at room temperature, 5 h at 60° C., and 10 min. at reflux. The mixture was cooled to room temperature, and further cooled in an ice bath. To the suspension, ethanol (200 mL) was added. The solid material was collected, and redissolved in water (50 mL). The product was precipitated out from the aqueous solution with ethanol (250 mL). The precipitate was collected, washed with ethanol, and dried under vacuum to give the title compound, 13.6 g (71%).

(2) 3-Amino-1-propanesulfonic acid and its sodium salt—ammonia in acetone (a) 3-Amino-1-propanesulfonic acid: 1,3-Propane sultone (61.1 g, 0.5 mole) was dissolved in acetone (600 mL). To the stirred acetone solution gaseous ammonia was introduced at room temperature at a flow rate of 200 to 250 cc/min. The introduction of ammonia was continued for 8 h (the temperature of the mixture rose to ~45° C. during the reaction). The reaction mixture was cooled to room temperature, and diluted with acetone (900 mL) and hexanes (300 mL), and stirred for 30 min. The solid material was collected, washed with acetone (3×60 mL), and dried at 70° C., to give a crystalline product (68.5 g, 98%) that contained a trace amount of a by-product [bis(3-sulfopropyl)amine according to $^1$H and $^{13}$C NMR spectroscopic analyses].

The crude product was dissolved in distilled water (90 mL) by heating on a steam bath. The aqueous solution was filtered while hot, and the funnel was washed with hot distilled water (30 mL). To the combined aqueous solution (filtrate and washing) was added absolute ethanol (600 mL). The mixture was heated at reflux temperature for 30 min, and cooled to room temperature. The solid material was collected, washed with 90% ethanol (3×70 mL), and then treated with 90% ethanol (500 mL) at reflux temperature for 20 min. The mixture was cooled to room temperature. The solid material was collected, washed with 95% ethanol (3×70 mL), and dried at 70° C., to afford the title compound as a white crystalline powder (61.8 g, 89%): NMR ($^1$H and $^{13}$C), MS (ESI$^-$), and FTIR conform the structure; mp >250° C.

(b) 3-Amino-1-propanesulfonic acid, sodium salt: 3-Amino-1-propanesulfonic acid (50.1 g, see above for preparation) was dissolved in distilled water (200 mL) by heating on a steam bath. To the aqueous solution was added sodium hydroxide (15.8 g). The mixture was heated on a steam bath until the sodium hydroxide had dissolved in the solution. The aqueous solution was filtered, and the funnel was washed with distilled water (50 mL). The combined aqueous solution (filtrate and washing) was evaporated to dryness on a rotary evaporator, and further dried in a vacuum oven at 80° C. overnight. The solid material was stirred in absolute ethanol (150 mL) at reflux temperature for 30 min. The mixture was cooled in an ice-water bath for 1 h. The solid material was collected, washed with absolute ethanol (50 mL), and dried in a vacuum oven at 80° C. overnight, to afford the title compound as a white crystalline powder (55.6 g, 96%), mp 198-199° C.

(3) 3-Amino-1-propanesulfonic acid and its sodium salt—ammonium hydroxide aqueous solution (a) 3-Amino-1-propanesulfonic acid: To a stirred mixture of ammonium hydroxide (28% aqueous solution, 100 mL) and acetone (1200 mL) was added a solution of 1,3-propane sultone (61.1 g, 0.5 mol) in acetone (100 mL) at room temperature. The mixture, while a low speed stirring was applied, was heated slowly to gentle reflux in 30 min. The mixture was refluxed gently for 2 h., and then cooled to room temperature. The solid material was collected and washed with acetone (2×100 mL). The solid was then treated with ethanol (95%, 500 mL) at reflux temperature for 20 min. The white solid was collected by filtration, washed with ethanol (2×50 mL), and dried at 70° C., to give a white solid (56.0 g). The crude product was dissolved in water (90 mL) by heating briefly. Ethanol (630 mL) was added to the hot solution. The mixture was kept at room temperature for 1 h, and the solid was collected and washed with 95% ethanol (3×50 mL), and dried at 70° C., to give a white crystalline solid, 47.5 g (68%).

(4) 3-Amino-1-propanesulfonic acid and its sodium salt—two step reactions (a) Step 1: 3-Benzylamino-1-propanesulfonic acid. A solution of 1,3-propane sultone (12.2 g, 0.1 mol) in butanol (50 mL) was added slowly to a solution of benzylamine (10.7 g, 0.1 mol) in butanol (100 mL). The mixture was stirred at room temperature for 2 h, heated under reflux for 2 h, and then cooled to room temperature. Acetone (150 mL) was added to the mixture. The precipitate was collected by filtration, washed with acetone (3×100 mL), and dried in vacuo to give a colorless solid, 16.5 g. The obtained crude product was dissolved in hot methanol (200 mL) and water (10 mL). The hot solution was filtered to remove impurities. The filtration was cooled, and a large amount of crystals was formed. In a subsequent step, acetone (200 mL) was added to the crystal-containing solution. The crystalline product was collected by filtration, washed with acetone, and dried in vacuo at 70° C. overnight, to give the compound as a colorless crystalline solid. Yield 15.3 g. mp>200° C.

(b) Step 2: 3-Amino-1-propanesulfonic acid: Debenzylation of the above-obtained intermediate is anticipated to afford the target compound in high quality and good yield.

(5) 3-Amino-1-propanesulfonic acid and its sodium salt—two step reactions (a) Step 1: 3-Azido-1-propanesulfonic acid, sodium salt: At room temperature, a solution of 1,3-propane sultone (0.5 g, 4 mmol) in tetrahydrofuran (5 mL) was added to a solution of sodium azide (0.26 g, 4 mmol) in a mixture of tetrahydrofuran (5 mL) and water (10 mL), and was stirred for 24 h. The tetrahydrofuran was removed under reduced pressure and a white precipitate formed. The white solid was collected by filtration and dried in-vacuo. The desired material was obtained as a fine white solid (0.27 g, 18%). The $^1$H NMR and MS were consistent with the expected structure.

(b) Step 2: 3-Amino-1-propanesulfonic acid, sodium salt: Hydrogenolysis or Staudinger reduction of the azide (followed by treatment with concentrated hydrochloric acid if the free acid form is desired).

(6) Dimethylamino Derivatives (a) 3-(Dimethylamino)-1-propanesulfonic acid—aqueous dimethylamine:

(1) Dimethylamine (40% aqueous solution, 250 mL) was placed in a round-bottom flask equipped with a magnetic stirring rod. The solution was cooled in an ice-acetone bath. While stirring was applied, a solution of 1,3-propane sultone (40.0 g, 327 mmol) in dichloromethane (250 mL) was added to the cold solution dropwise,. The internal temperature was maintained between −5 to −10° C. After the completion of the addition, the bath was removed and the mixture was stirred for 30 min. The internal temperature reached 10° C. The mixture was transferred into a separatory funnel, and the organic layer was discarded. The aqueous layer was washed with dichloromethane (2×50 mL), and then filtered through a sintered glass funnel. The filtrate was concentrated on a rotary evaporator to give a solid residue. The solid residue was heated with ethanol (400 mL) at reflux for 10 min., and then cooled in an ice bath. The solid material was collected by filtration, washed with ethanol (2×50 mL), and dried at 70° C., to give a white crystalline solid 50.0 g (91%). (The product contained 1.0 to 1.5% of di-N-substituted product, which can be further purified according to the required specifications.)

(2) A solution of 1,3-propanesultone (164 g, 1.34 mol) in THF (82 mL) was added dropwise to a cooled (−10° C.) solution of dimethylamine (40 wt % in water, 1700 mL, 13.4 mol) over a 1.5 hours period. The temperature in the reaction vessel was controlled to remain within −10 to −5° C. under this rate of addition. Samples were taken for analysis at the interval of 1 hour and 3 hours.

Upon completion of the reaction, the solvent and the excess reagent were removed under reduced pressure. Ammonium hydroxide (5 M, 100 mL) was added to dissolve the solid and the solution was concentrated to dryness, twice. The residue was dissolved in water (80 mL) and recrystallized by slowly addition of ethanol (1000 mL) at −10° C. yield, 179 g (80%). In process control (IPC) analysis indicated that the impurity:

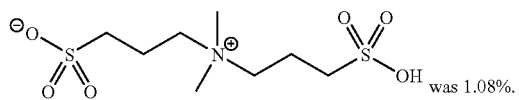 was 1.08%.

The $^1$H NMR and MS of the major product were consistent with the expected structure.

(b) 3-(Dimethylamino)-1-propanesulfonic acid—dimethylamine gas: 1,3-Propane sultone (61.1 g, 0.5 mole) is dissolved in acetone (600 mL). To the stirred acetone solution at room temperature, gaseous dimethylamine is introduced at a flow rate of 100 to 150 cc/min. The introduction of dimethylamine is continued for 8 h (the temperature of the mixture should rise to ~45° C. during the reaction). The reaction mixture is cooled to room temperature, and diluted with acetone (900 mL) and hexanes (300 mL). The mixture is then stirred for 30 min.

The solid material is collected, washed with acetone (3×60 mL), and dried at 70° C., to give a crystalline product The crude product is suspended in methanol (5 volumes) and the mixture is warmed to reflux. Water is added dropwise until a clear solution is obtained. The solid material is collected by filtration, washed with cold (5° C.) methanol (2×70 mL), and then is dried at 70° C., to afford the title compound as a white crystalline powder (about 80 g expected).

(7) 3-(Dimethylamino)-1-propanesulfonic acid—a two step reaction (a) Step 1: 3-(Benzydimethylamino)-1-propanesulfonic acid, inner salt (the intermediate): At room temperature, a solution of benzyldimethylamine (35.7 g, 264 mmol) in 1,4-dioxane (30 mL) was added, dropwise over 15 min., to a solution of 1,3-propane sultone (31.1 g, 254 mmol) in 1,4-dioxane. The milky mixture was then heated to refluxing and kept heated (100-100.5° C.) for 4 h. The mixture was cooled to room temperature and left at room temperature overnight, and further cooled to 9.0° C. with an ice-bath. The white solid was collected by filtration, washed with acetone (2×50 mL), and dried in a vacuum oven at 60° C. overnight. The solid obtained (70.37 g) contained 0.25 equivalent of 1,4-dioxane, detected by $^1$H NMR.

The solid was subsequently suspended in 3 volumes of anhydrous ethanol, and the resulting suspension was heated at reflux for 2 h. The mixture was then cooled at 2.0° C. in an ice-water bath. The solid material was collected by filtration, rinsed with cold (~1° C.) ethanol (2×40 mL). The filter cake was air-dried for 30 min., and then in a vacuum oven at 60° C. for 18 h. The final product was obtained as a white solid (61.28 g, 94%). The $^1$H and $^{13}$C NMR and MS were consistent with the expected structure.

(b) Step 2: 3-(Dimethylamino)-1-propanesulfonic acid: Debenzylation of the above-obtained intermediate was achieved by treating the intermediate with ammonium formate and catalytic amount of 10% palladium on carbon in 80% degassed methanol, followed by proper work-up, in 96% yield.

(c) Step 2: 3-(Dimethylamino)-1-propanesulfonic acid: Debenzylation of the above-obtained intermediate was achieved by treating the intermediate with 10% Pd/C (w/w) and 50 p.s.i. H$_2$ in 90% methanol at room temperature. The mixture was filtered over a pad of Celite, which was washed with methanol, obtaining the desired product in quantitative yield.

As such, in one embodiment, the sultone ring opening reaction may be represented by:

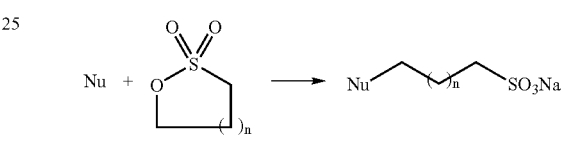

wherein n=1, Nu is benzydimethylamino, with the further step of removing the the benzyl moiety using palladium on carbon under an atmosphere of hydrogen gas.

(8) 3-(1,2,3,6-Tetrahydropyridinyl)-1-propanesulfonic acid and derivatives (a) 3-(1,2,3,6-Tetrahydropyridinyl)-1-propanesulfonic acid: At room temperature, a solution of 1,3-propane sultone (8.1 g) in butanone (50 mL) was added to a stirred solution of 1,2,3,6-tetrahydropyridine (4.6 g) in butanone (100 mL). The mixture was heated briefly at 50° C. The precipitate was collected through filtration, washed with butanone and diethyl ether, dried at 70° C., to give the title compound, 11.0 g (87%), in NMR pure form. Further purification from water (40 mL) and ethanol (600 mL) resulted in a white crystalline solid product.

(b) 3-(1,2,3,4-Tetrahydroisoquinolinyl)-1-propanesulfonic acid: A mixture of 1,2,3,4-tetrahydoisoquinoline (26.6 g, 200 mmol) and 1,3-propane sultone (24.5 g, 200 mmol) in butanone (250 mL) was refluxed for 2 h. The reaction mixture was cooled in an ice-bath. The precipitate was collected by filtration, washed with acetone (3×100 mL), and dried in a vacuum oven (70° C.), to give a crude product (48 g). The crude product was recrystallized from 99% ethanol (900 mL), providing the final product as a white crystalline solid, 36 g (70%).

(c) 3-(4-Cyano-4-phenylpiperidin-1-yl)-1-propanesulfonic acid: The 4-cyano-4-phenylpiperidine hydrochloride (2.0 g, 9.0 mmol) was mixed with 1N NaOH (20 mL), and CH$_2$Cl$_2$ (20 mL) was added. The phases were separated. The aqueous phase was extracted two more times with CH$_2$Cl$_2$ (20 mL). The organic layers were combined, dried over MgSO$_4$, filtered, and evaporated to dryness under reduced pressure. To a solution of piperidine (1.43 g, 7.7 mmol) in acetone (20 mL) was added 1,3-propane sultone (1.02 g, 8.5 mmol) at room temperature. The mixture was then heated at reflux for 2 h. The resultant suspension was cooled to room temperature. The solid was collected by filtration, washed with acetone and dried under reduced pressure. The solid was recrystallized from MeOH (and traces of water) to afford 800 mg (34%) of pure 3-(4-cyano-4-phenylpiperidin-1-yl)-1-propanesulfonic acid.

(d) 3-[4-(4-fluorophenyl)-1,2,3,6-tetrahydropyridin-1-yl]-1-propanesulfonic acid: The 4-(4-fluorophenyl)-1,2,3,6-tetrahydropyridine hydrochloride (2.58 g, 14.5 mmol) was mixed with 1N NaOH (20 mL), and $CH_2Cl_2$ (20 mL) was added. The biphasic solution was shaken. The organic layer was dried over $MgSO_4$, and the solvents were removed by evaporation under reduced pressure. The resulting free amine (1.96 g, 13.7 mmol) was dissolved in acetone (30 mL). 1,3-propane sultone (1.74 g, 14.5 mmol) ws added to the solution at room temperature. The mixture was then heated at reflux overnight.

Only a small amount of compound precipitated. The resulting suspension was cooled to room temperature with stirring and a larger amount of solid precipitated. The suspension was heated with the addition of a small amount of MeOH until complete dissolution of the solid. The resulting solution was heated under reflux for a few minutes and was cooled to room temperature with stirring. The solid was collected by filtration, washed with MeOH and dried under vacuum. This procedure allowed for the isolation of 1.33 g (32%) of 3-[4-(4-fluorophenyl)-1,2,3,6-tetrahydropyridin-1-yl]-1-propanesulfonic acid.

(e) 3-[4-(4-bromophenyl)-4-hydroxypiperidin-1-yl]-1-propanesulfonic acid: To a solution of 4-(4-bromophenyl)-4-piperidinol (2.51 g, 9.8 mmol) in MeOH (25 mL) was added 1,3-propane sultone (1.28 g, 10.7 mmol) at room temperature. The mixture was then heated at reflux for 2 h. Only a small amount of compound precipitated. The resulting suspension was cooled to room temperature with stirring and a solution of 50% MeOH/Acetone was added to precipitate the maximum amount of compound. The solid was collected by filtration, washed with 50% MeOH/Acetone (2×25 mL) and dried in vacuo. This procedure allowed for the isolation of 2.11 g (57%) of pure 3-[4-(4-bromophenyl)-4-hydroxypiperidin-1-yl]-1-propanesulfonic acid.

(f) 3-[4-(4-chlorophenyl)-4-hydroxypiperidin-1-yl]-1-propanesulfonic acid: To a solution of 4-(4-chlorophenyl)-4-piperidinol (2.5 g, 11.8 mmol) in acetone (25 mL) was added 1,3-propane sultone (1.56 g, 13.0 mmol) at room temperature. The mixture was then heated at reflux for 2 h. The reaction was cooled to room temperature. The solid was collected by filtration, washed with acetone (2×20 mL) and dried in vacuo. This procedure allowed for the isolation of 2.83 g (72%) of pure 3-[4-(4-chlorophenyl)-4-hydroxypiperidin-1-yl]-1-propanesulfonic acid.

(g) 3-(4-acetyl-4-phenylpiperidin-1-yl)-1-propanesulfonic acid: 4-Acetyl-4-phenylpiperidine hydrochloride (3.32 g, 12.5 mmol) was mixed with 1N NaOH (20 mL), and $CH_2Cl_2$ (20 mL) was added. The biphasic solution was shaken, and the organic layer was dried over $Na_2SO_4$, filtered and evaporated under reduced pressure.

1,3-propane sultone (1.20 g, 10.0 mmol) was added to a solution of 4-acetyl-4-phenylpiperidine (1.83 g, 9.0 mmol) in acetone (22 mL) at room temperature. The mixture was then heated at reflux for 2 h, and subsequently was cooled to room temperature. The solid was collected by filtration, washed with acetone (2×20 mL) and dried in vacuo. This procedure allowed for the isolation of 2.65 g (90%) of 3-(4-acetyl-4-phenylpiperidin-1-yl)-1-propanesulfonic acid.

(h) 3-[4-(4-chlorophenyl)-1,2,3,6-tetrahydropyridin-1-yl]-1-propanesulfonic acid: The 4-(4-chlorophenyl)-1,2,3,6-tetrahydropyridine hydrochloride (2.52 g, 10.9 mmol) was mixed with 1N NaOH (20 mL) and $CH_2Cl_2$ (20 mL) was added. The biphasic solution was shaken. The organic layer was dried over $Na_2SO_4$, filtered and the solvent was removed by evaporation under reduced pressure.

1,3-propane sultone (1.41 g, 11.8 mmol) was added to a solution of 4-(4-chlorophenyl)-1,2,3,6-tetrahydropyridine (2.07 g, 10.7 mmol) in acetone (25 mL) at room temperature. The mixture was then heated at reflux for 2 h, and subsequently was cooled to room temperature. The solid was collected by filtration, washed with acetone (2×20 mL) and dried in vacuo.

The product was then purified by addition to a solution of 50% MeOH/acetone (75 mL). The suspension was kept at reflux for 5 min before 25 mL of cold acetone was added. The solid was collected by filtration, and washed with acetone (2×25 mL). This procedure allowed for the isolation of 1.48 g (44%) of 3-[4-(4-chlorophenyl)-1,2,3,6-tetrahydropyridin-1-yl]-1-propanesulfonic acid.

(9) Miscellaneous Compounds (a) 3-Tryptamino-1-propanesulfonic acid: Tryptamine (24 g, 0.15 mol) was dissolved in a mixture of butanone (200 mL) and acetone (100 mL). To the mixture was added a solution of 1,3-propane sultone (18.3 g) in acetone (100 mL). The mixture was heated at reflux temperature for 1 h, then cooled to room temperature. The precipitate was collected by filtration, washed with acetone (2×100 mL). The solid was dissolved in a mixture of 95% ethanol (600 mL) and water (100 mL) at refluxing temperature, and the mixture was filtered through a pad of Celite. The filtrate was concentrated on a rotary evaporator to a volume of about 100 mL. The residue was cooled at 4° C. for 1 h. The crystalline solid was collected by filtration, washed with ethanol (3×70 mL), dried at 70° C., to give the final product (16 g).

(b) 3-(1,2,3,4-Tetrahydro-naphthylamino)-1-propanesulfonic acid: 1,2,3,4-tetrahydro-1-naphthylamine (24.8 g, 0.168 mol) and 1,3-propane sultone (20.58 g, 0.168 mol) were stirred in toluene (300 mL) at 80° C. for 3 h. The mixture was cooled to room temperature. To the mixture was added hexanes (500 mL). The precipitate was collected by filtration, washed with hexanes (2×100 mL), and dried at 60° C., to give a crude product (40 g). The crude product was dissolved in a mixture of ethanol (800 mL) and water (80 mL) at reflux temperature. After filtration of the hot solution, the filtrate was cooled at −10° C. The crystalline solid was collected by filtration, washed with ethanol (2×50 mL), and dried at 70° C. under vacuum, providing the final product as white crystals, 26 g. From mother liquid was recovered 13 g of the product which was slightly pink-colored.

(c) 3-(1-Adamantylamino)-1-propanesulfonic acid: 1-Adamantanamine hydrochloride (80 g, 0.426 mol) was treated with NaOH (10% aqueous solution, 400 mL). The free amine was extracted with dichloromethane (1×400 mL, and 2×100 mL). The combined organic layers were washed with brine (50 mL) and dried over sodium sulfate (10 g). The solvent was then removed under reduced pressure. The resulting white waxy solid was coevaporated with acetonitrile (50 mL).

The resulting solid was suspended in acetonitrile (200 mL). The suspension mixture was added dropwise over 20 min to a solution of 1,3-propane sultone (53 g, 0.426 mol) in acetonitrile (300 mL) and THF (200 mL). The thick mixture was stirred for 2 h at reflux with the aid of a mechanical stirrer. The suspension was then cooled to 13° C. The solid was collected by filtration, rinsed with acetonitrile (2×100 mL), ether (1×100 mL), and then air-dried for 30 min. The solid was further dried in vacuo at 60° C. overnight to give the first crop of the product (104.17 g). A second crop of product was collected from the filtrate and dried in vacuo in the same manner (3.39 g).

The NMR spectra of both crops were identical. The two crops were combined and suspended in methanol (720 mL), and the mixture was then heated to reflux. Water (490 mL) was added dropwise over 45 min. Once the solid had been dissolved, the solution was kept at reflux for 30 min. The mixture was left to cool slowly to 40° C. during 1.5 h. The mixture was cooled further to 5° C. and stirred overnight at this temperature. The white flaky solid was collected by filtration, rinsed with cold (0° C.) methanol (2×125 mL), air-dried for 60 min., and then dried in the vacuum oven at 60° C. overnight, to give a white flaky solid (97.1 g, 83%).

(d) 3-(2-Norbornylamino)-1-propanesulfonic acid: A solution of 1,3-propane sultone (8.1 g, 65.7 mmol) in 2-butanone (10 mL) was added to a solution of 2-aminonorbornane (7.3 g, 65.7 mmol) in 2-butanone (50 mL). The mixture was heated at 60° C. for 1 h. The suspension was cooled to room temperature, and the solid material was collected by filtration, and washed with ethanol (2×20 mL). The crude product was recrystallized from 95% ethanol to afford the desired compound as a white crystalline solid (8.2 g, 53%).

(e) 3-(2-Admantylamino)-1-propanesulfonic acid: 2-Aminoadamantane hydrochloride (10 g) was treated with NaOH in water. The free amine, thus released, was extracted with dichloromethane. The organic layer was dried over magnesium sulfate and the solvent was removed in vacuo. The resulting white solid was dried 30 minutes at room temperature under vacuum.

The freed 2-aminoadamantane (7.98 g, 52 mmol) was dissolved in THF (52 mL). To this solution was added a solution of 1,3-propane sultone (7.4 g, 60 mmol in THF). The mixture was heated at reflux for 4 h, and cooled in an ice-bath. The solid material was collected by filtration, air-dried for 15 min., and further dried in vacuo to give a crude product (11.2 g). The crude material was recrystallized in methanol/water (60 mL/35 mL). After cooled at 4° C. in a refrigerator, the solid was collected by filtration, rinsed with methanol, and dried in a vacuum oven at 60° C. overnight, affording a white crystalline sandy solid (10.45 g, 74%).

(f) 3-((4-Hydroxy-2-pentyl)amino)-1-propanesulfonic acid: 2-Amino-1-pentanol (10 g, 94 mmol) was added to a solution of 1,3-propane sultone (12.6 g, 100 mmol) in 2-butanone (95 mL). The mixture was heated at reflux for 3.5 h. The mixture was then cooled to room temperature, and cooled in an ice-bath. The solid was subsequently collected by filtration, rinsed with cold THF, and air-dried for 20 min. A suspension of the solid in ethanol (80 mL) was heated at reflux for 1 h, and then cooled in an ice-water bath.

The solid was collected by filtration, rinsed with cold ethanol. The material was air-dried for 15 min., and then in a vacuum oven at 60° C. overnight. The final product was obtained as a fine white powder (14.49 g, 68%).

(g) 3-(t-Butylamino)-1-propanesulfonic acid: tert-Butylamine (53.1 mL, 0.5 mol) was added, dropwise over 25 min., to a solution of 1,3-propane sultone (63.5 g, 0.52 mol) in THF (425 mL). The mixture was heated at 45° C. for 1.5 h, followed by refluxing for 1.5 h. While the reflux was maintained, 155 mL of THF was distilled off. The resulting suspension was cooled to 5° C. with an ice-bath.

The solid was collected by suction filtration and rinsed with cold THF (0° C., 2×50 mL). The wet cake was air-dried under suction for 30 min., and then dried in a vacuum oven at 60° C. overnight, to give a crude product (75.59 g). The crude material was suspended in absolute ethanol (275 mL), and the mixture was heated at reflux for 2 h. The mixture was then cooled to 10° C. The solid was collected by suction filtration, air-dried under suction for 30 min., and then dried in a vacuum oven at 60° C. overnight, resulting in the final product as a fine white powder (74.6 g, 77%). The $^1$H NMR and MS were consistent with the structure.

Likewise, the following compounds that are listed in Tables 2 and 3 may be prepared in a similar fashion.

TABLE 2

Product from 1,3-propane sultone opening reactions

Compound 3-amino-1-propanesulfonic acid and sodium salt
3-dimethylamino-1-propanesulfonic acid and sodium salt
3-(1-piperidinyl)-1-propanesulfonic acid
3-phenylamino-1-propanesulfonic acid and sodium salt
1,4-piperazinebis(propanesulfonic acid)
3-[1-(1,2,3,6-tetrahydropyridinyl)]-1-propanesulfonic acid
3-[2-(1,2,3,4-tetrahydroisoquinolinyl)]-1-propanesulfonic cid
3-(4-pyridinylamino)-1-propanesulfonic acid and sodium salt
3-(4-benzylpiperazinylamino)-1-propanesulfonic acid
3-(3-pyridinyloxy)-1-propanesulfonic acid
3-(4-quinazolinyloxy)-1-propanesulfonic acid
3-(benzylamino)-1-propanesulfonic acid
(3-sulfopropyl)triethylammonium hydroxide, inner salt
3-((2-(3-indolyl)ethyl)amino)-1-propanesulfonic acid
3-(2-(6,7-dimethoxy-1,2,3,4-tetrahydroisoquinolinyl))-1-propanesulfonic acid
3-(1-(1,2,3,4-tetrahydroquinolinyl))-1-propanesulfonic acid
3-(1,2,3,4-tetrehydro-9H-pyrido[3,4-b]indolyl)-1-propanesulfonic acid and sodium salt
3-(2-(6-methoxy-1,2,3,4-tetrahydroisoquinolinyl))-1-propanesulfonic acid
3-(2-(3-methoxycarbonyl-1,2,3,4-tetrahydroisoquinolinyl))-1-propanesulfonic acid
3-(N,N-diethylamino)-1-propanesulfonic acid
3-(1,2,3,4-tetrahydro-1-naphthylamino)-1-propanesulfonic acid
3-(1-pyrrolidinyl)-1-propanesulfonic acid
3-(4-Benzyl-1-piperidinyl)-1-propanesulfonic acid
3-(2-(1,2,3,4,5,6,7,8-octahydroisoquinolinyl))-1-propanesulfonic acid
3-((3-hydroxy-1-propyl)amino)-1-propanesulfonic acid
3-(2-(3-carboxyl-1,2,3,4-tetrahydroisoquinolinyl))-1-propanesulfonic acid and disodium salt
3-phthalimido-1-propanesulfonic acid, potassium salt
L-alpha-(3-sulfopropyl)amino-ε-caprolactam, sodium salt
3-((3,5-dimethyl-1-adamantyl)amino)-1-propanesulfonic acid
3-((4-methoxyphenyl)amino)-1-propanesulfonic acid
3-(ethylamino)-1-propanesulfonic acid
3-((1-adamantyl)amino)-1-propanesulfonic acid
3-((4-aminophenyl)amino)-1-propanesulfonic acid and sodium salt
3-azido-1-propanesulfonic acid, sodium salt
3-(methylamino)-1-propanesulfonic acid and sodium salt
3-(t-butylamino)-1-propanesulfonic acid
3-((1-adamantylmethyl)amino)-1-propanesulfonic acid
N,N'-(bis-propanesulfonic acid)-imidazole, sodium salt
3-((2-(1-adamantyl)ethyl)amino)-1-propanesulfonic acid

TABLE 2-continued

Product from 1,3-propane sultone opening reactions

Compound 3-(3-quinuclidinylamino)-1-propanesulfonic acid
3-(2-norbornylamino)-1-propanesulfonic acid
3-(2-Adamantyl)amino-1-propanesulfonic acid
1-Imidazole propanesulfonic acid, sodium salt
N,N-bis-(3-sulfopropyl)imidazole hydrochloride
3-(4-Fluorophenyl)aminopropanesulfonic acid, sodium salt
3-(2-hydroxyphenyl)aminopropanesulfonic acid
3-Pyrrole-1-propanesulfonic acid, sodium salt
3-(N-(3-imidazol 1-propane)imidazol)-1-propanesulfonic acid chloride, sodium salt
3-Hydroxilamino-1-propanesulfonic acid
3-Nitro-1-propanesulfonic acid, sodium salt
N,N'-(1,1'-ethenediamine)dipropanesulfonic acid, disodium salt
alpha-N-(3-Sulfopropyl)-L-lysine
N-(3-sulfopropyl)glycine
3-(5-Methoxytryptamino)-1-propanesulfonic acid
3-(Dibenzylamino)-1-propanesulfonic acid. Sodium salt
N-tert-Butyloxycarbonyl-3-aminopropanesulfonic acid, sodium salt
N-Benzyloxycarbonyl-3-aminopropanesulfonic acid, mono hydrate, mono sodium chloride
4-Iodo-N-(3-sulfopropyl)-L-phenylalnine methyl ester
1-(3-Sulfopropyl)-4-phenylpyridinium
4-Phenyl-1-sulfopropyl-1,2,3,6-tetrahydropyridine, sodium salt
3-[2-(7-Methoxy-1,2,3,4-tetrahydroisoquinolinyl)]-1-propane sulfonic acid
3-[2-(6-Methoxy-1,2,3,4-tetrahydroisoquinolinyl)]-1-propane sulfonic acid, sodium salt
3-[2-(8-Methoxy-1,2,3,4-tetrahydroisoquinolinyl)]-1-propane sulfonic acid, sodium salt
3-phosphonopropanesulfonic acid, trisodium salt
3-(2-hydroxyethyl)amino-1-propanesulfonic acid
3-(3-hydroxy-1-propyl)amino-1-propanesulfonic acid
3-[(R)-2-hydroxy-1-propyl]amino-1-propanesulfonic acid
3-[(dl)-1-hydroxy-2-propyl]amino-1-propanesulfonic acid
3-(4-hydroxy-1-butyl)amino-1-propanesulfonic acid
3-(5-hydroxy-1-pentyl)amino-1-propanesulfonic acid
3-(6-hydroxy-1hexyl)amino-1-propanesulfonic acid
3-(4-hydroxyphenyl)amino-1-propanesulfonic acid
(+)-3-[(S)-2-hydroxy-1-propyl]amino-1-propanesulfonic acid
(+)-3-[(S)-1-hydroxy-2-propyl]amino-1-propanesulfonic acid
(−)-3-[(R)-1-hydroxy-2-propyl]amino-1-propanesulfonic acid
(+)-3-[(S)-1-hydroxy-2-butyl]amino-1-propanesulfonic acid
(−)-3-[(R)-1-hydroxy-2-butyl]amino-1-propanesulfonic acid
3-[(dl)-1-hydroxy-2-pentyl]amino-1-propanesulfonic acid
3-[(dl)-6-hydroxy-2-hexyl]amino-1-propanesulfonic acid
3-(1-hydroxymethyl-1-cyclopentyl)amino-1-propanesulfonic acid
3-amylamino-1-propanesulfonic acid
3-hexylamino-1-propanesulfonic acid
3-heptylamino-1-propanesulfonic acid
3-octylamino-1-propanesulfonic acid
3-nonylamino-1-propanesulfonic acid
3-decylamino-1-propanesulfonic acid
3-undecylamino-1-propanesulfonic acid
3-tridecylamino-1-propanesulfonic acid
3-tetradecylamino-1-propanesulfonic acid
3-hexadecylamino-1-propanesulfonic acid
3-octadecylamino-1-propanesulfonic acid
3-(isobutylamino)-1-propanesulfonic acid
3-(isopropylamino)-1-propanesulfonic acid
3-(isoamylamino)-1-propanesulfonic acid
3-(cyclopropylamino)-1-propanesulfonic acid
3-(cyclopentylamino)-1-propanesulfonic acid
3-(cycloheptylamino)-1-propanesulfonic acid
N,N-bis-3-sulfopropyldimethylammonium, sodium salt
5-phenyl-1-sulfopropyl-1,2,3,6-tetrahydropyridine
2-phenyl-1-sulfopropyl-1,2,3,6-tetrahydropyridine
3-[2-(5-amino-1,2,3,4-tetrahydro isoquinolinyl)]-1-propane sulfonic acid hydrochloride

TABLE 2-continued

Product from 1,3-propane sultone opening reactions

Compound

3-[2-(5-diacetylaminoisoquinolinyl)]-1-propanesulfonic acid inner salt
3-[2-(5-nitroisoquinolinyl)]-1-propanesulfonic acid inner salt
3[2-(5-bromo-1,2,3,4-tetrahydro isoquinolinyl)]-1-propanesulfonic acid
4-(3-phenylpropyl)-1-sulfopropylpyridine
4-(3-phenylpropyl)-1-sulfopropyl-2,3,6-tetrahydropyridine
2-(3-sulfopropyl)-7-nitro-1,2,3,4,-tetrahydroisooquinoline
2-(3-sulfopropyl)-7-amino-1,2,3,4-tetrahydroiosquinoline hydrochloride
2-(3-sulfopropyl)-7-bromo-1,2,3,4-tetrahydroisoquinoline)
2-(3-sulfopropyl)-5-iodo-1,2,3,4-tetrahydroisoquinoline isobutyl ester hydrochloride
2-(3-sulfopropyl)-5-iodo-1,2,3,4-tetrahydroisoquinoline
2-(3-sulfopropyl)-9H-Pyrido(3,4-b)indole, inner salt
N-benzyloxycarbonyl-3-amino-2-hydroxypropanesulfonic acid sodium salt
N-benzyloxycarbonyl-3-aminopropanesulfonic acid sodium salt
2-(3-sulfopropyl)-6-amino-1,2,3,4-tetrahydro-9H-pyrido[3,4b]indole hydrochloride
2-(3-sulfopropyl)-6-nitro-1,2,3,4-tetrahydro-9H-pyrido[3,4b]indole
2-(3-sulfopropyl)-1,2,3,4-tetrahydro-9H-pyrido[3,4b]indole
2-(3-sulfopropyl)-6-bromo-1,2,3,4-tetrahydro-9H-pyrido[3,4b]indole
N-(3-sulfopropyl)-6-carboxylic acid-1,2,3,4-tetrahydro-beta-carboline hydrochloride
N-benzyl-N,N-dimethyl-3-aminopropanesulfonic acid, inner salt
N,N-dibenzyl-3-aminopropanesulfonic acid
4-iodo-N-(3-sulfopropyl)-L-phenylalanine amide
3-[(1,3-benzodioxol-5ylmethy)amino]-1-propanesulfonic acid
3-[3,4-dimethoxybenzyl)amino]-1-propanesulfonic acid
3-[3,4,5-trimethoxybenzyl)amino}-1-propanesulfonic acid
3-[2,3-dimethoxybenzyl)amino]-1-propanesulfonic acid
3-[(3,5-dimethoxybenzyl)amino]-1-propanesulfonic acid
3-[2,4-dimethoxybenzyl)amino]-1-propanesulfonic acid
3-[(3,4-dihydroxybenzyl)amino]-1-propanesulfonic acid
6-methoxy-2-(3-sulfopropyl)-1,2,3,4-tetrahydro-9H-pyrido[3,4-b]indole, sodium salt
N-(N-methylnicotinoyl)amino-3-propanesulfonic acid, inner salt with triethylamine salt
4-(3-cyclohexen-1-yl)-1-(3-sulfopropyl)-pyridine
N-(sulfopropyl)-9H-indeno[2,1-c]pyridin-9-one inner salt
N-(sulfopropyl)-1,2,3,4-tetrahydrobenzo[b]thieno-[2,3-c]-pyridine
3-(trimethylamino)propanesulfonic acid inner salt

TABLE 3

Product from 1,4-butane sultone opening reactions

Compound 4-hydroxy-1-butanesulfonic acid, sodium salt
4-(1-piperdinyl)-1-butanesulfonic acid
4-(4-pyridinylamino)-1-butanesulfonic acid and sodium salt
4-amino-1-butanesulfonic acid and sodium salt
4-(benzylamino)-1-butanesulfonic acid
4-[2-(1,2,3,4-tetrahydroisoquinolinyl)]-1-butanesulfonic acid
4-amino-1-butanesulfonic acid
4-(benzyloxycarbonylamino)-1-butanesulfonic acid sodium salt
4-(4-cyclohex-3-enylpyridyl)butanesulfonic acid inner salt

TABLE 4

Miscellaneous products of sultone opening reactions
Structure/
Name of Compound 2-phenyl-1-sulfopropyl-1,2,3,6-tetrahydropyridine

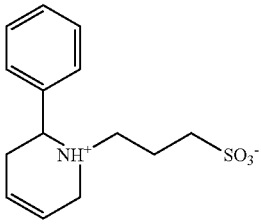

4-(3-phenylpropyl)-1-sulfopropylpyridine

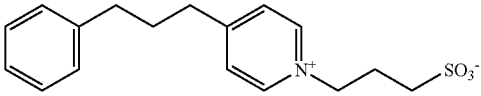

4-(3-phenylpropyl)-1-sulfopropyl-2,3,6-tetrahydropyridine

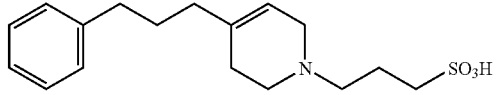

3-(4-cyano-4-phenylpiperidin-1-yl)-1-propanesulfonic acid

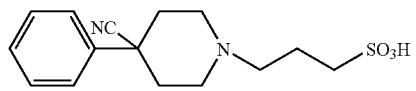

3-[4-(4-fluorophenyl)-1,2,3,6-tetrahydropyridin-1-yl]-1-propanesulfonic acid

3-[4-(4-bromophenyl)-4-hydroxypiperidin-1-yl]-1-propanesulfonic acid

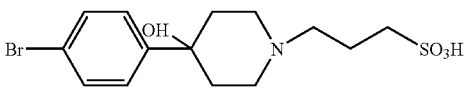

3-[4-(4-chlorophennyl)-4-hydroxypiperidin-1-yl]-1-propanesulfonic acid

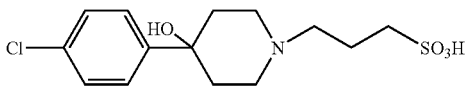

3-(4-acetyl-4-phenylpiperidin-1-yl)-1-propanesulfonic acid

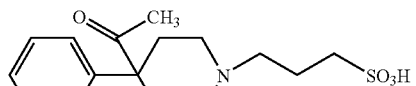

3-[4-(4-chlorophenyl)-1,2,3,6-tetrahydropyridin-1-yl]-1-propanesulfonic acid

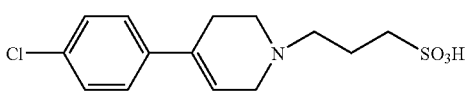

TABLE 4-continued

Miscellaneous products of sultone opening reactions
Structure/
Name of Compound 3-(4-phenylpiperazin-1-yl)-1-propanesulfonic acid

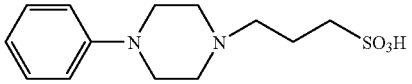

3-[4-(4-chlorophenyl)piperazin-1-yl]-1-propanesulfonic acid

3-[4-(2-fluorophenyl)piperazin-1-yl]-1-propanesulfonic acid

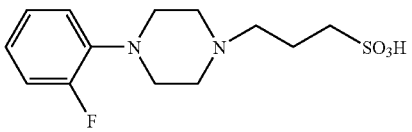

3-[4-(4-nitrophenyl)piperazin-1-yl]-1-propanesulfonic acid

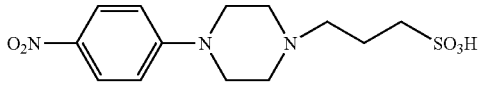

3-[4-(4-fluorophenyl)piperazin-1-yl]-1-propanesulfonic acid

3-(3,4-dimethoxybenzyl) amino)-1-propanesulfonic acid

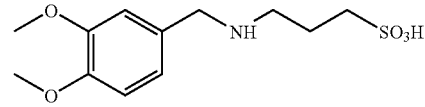

L-Phe-L-Phe-Taurine

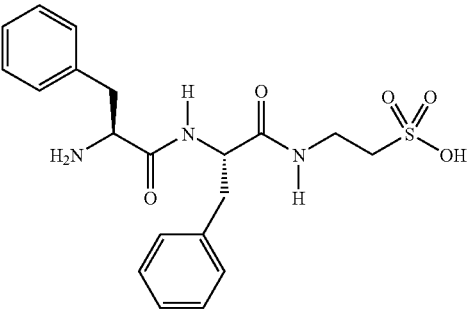

N-benzyloxycarbonyl-3-amino-2-hydroxy-1-propanesulfonic acid sodium salt

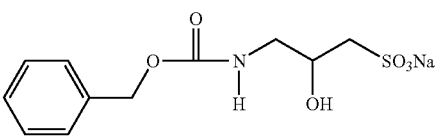

TABLE 4-continued

Miscellaneous products of sultone opening reactions
Structure/
Name of Compound

N-benzyloxycarbonyl-4-amino-1-butanesulfonic acid sodium salt

N-benzyloxycarbonyl-3-amino-1-propanesulfonic acid sodium salt

3-{[(benzhydrylamino) carbonyl]amino}-1-propanesulfonic acid

3-[(phenylacetyl)amino]-1-propanesulfonic acid, sodium salt

3-{[(benzylamino) carbonyl] amino} -1-propanesulfonic acid, sodium salt

3-{[(hexylamino)carbonyl]amino}-1-propanesulfonic acid, sodium salt

3-{[(dodecylamino)carbonyl]amino}-1-propanesulfonic acid, sodium salt

TABLE 4-continued

Miscellaneous products of sultone opening reactions
Structure/
Name of Compound

3-{[(adamantylamino)carbonyl]amino}-1-propanesulfonic acid, sodium salt

3-{[2-(4-isobutylphenyl)propanoyl]amino}-1-propanesulfonic acid, sodium salt

3-{[(benzylamino)carbonothioyl]amino}-1-propanesulfonic acid, sodium salt 3-dibenzylamino-1-propanesulfonic acid 3-[((1,3-benzodioxol-5-yl)methyl)amino]-1-propanesulfonic acid 3-(3,4-dimethoxybenzyl amino)-1-propanesulfonic acid 3-(3,4,5-trimethoxybenzylamino)-1-propanesulfonic acid TABLE 4-continued Miscellaneous products of sultone opening reactions
Structure/
Name of Compound 3-(2,3-dimethoxybenzylamino)-1-propane sulfonic acid 3-(3,5-dimethoxybenzylamino)-1-propane sulfonic acid 3-(2,4-dimethoxybenzylamino)-1-propanesulfonic acid 3-(3,4-dihydroxybenzyl amino)-1-propanesulfonic acid 3-(1-adamantyl)amino-1-propanesulfonic acid 3-(t-butyl)amino-1-propanesulfonic acid 3-(2-norbornyl)amino-1-propanesulfonic acid TABLE 4-continued Miscellaneous products of sultone opening reactions
Structure/
Name of Compound 3-(2-adamantyl)amino-1-propanesulfonic acid

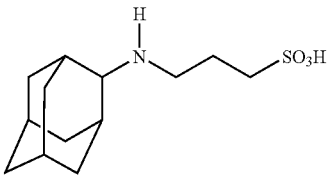

4-amino-1-butanesulfonic acid

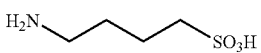

5-amino-1-pentanesulfonic acid

6-amino-1-hexanesulfonic acid

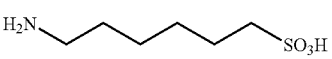

3-isobutylamino-1-propanesulfonic acid

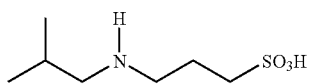

3-isopropylamino-1-propanesulfonic acid

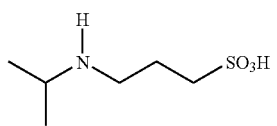

3-isoamylamino-1-propanesulfonic acid

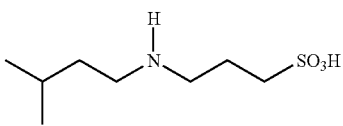

3-(cyclopropylamino)-1-propanesulfonic acid

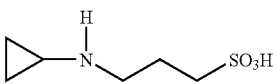

3-(cyclopentylamino)-1-propanesulfonic acid

3-(cycloheptylamino)-1-propanesulfonic acid

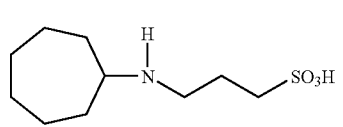

TABLE 4-continued

Miscellaneous products of sultone opening reactions
Structure/
Name of Compound 3-(amidinothio)-1-propanesulfonic acid 3-(ethylamino)-1-propanesulfonic acid 3-(3,5-dimethyl-1-adamantylamino)-1-propanesulfonic acid 3-cyclohexylamino-2-hydroxy-1-propanesulfonic acid 3-(3-pentyl)amino-1-propanesulfonic acid 3-(tert-amyl)amino-1-propanesulfonic acid 3-(1,1-dimethyl-2-hydroxyethyl)amino-1-propanesulfonic acid 3-(1-carboxy-1-methylethylamino)-1-propanesulfonic acid TABLE 4-continued Miscellaneous products of sultone opening reactions
Structure/
Name of Compound 3-[(1R,2S)-2-methylcyclohexyl]amino-1-propanesulfonic acid 3-(2,3-dimethylcyclohexyl)amino-1-propanesulfonic acid 3-neopentylamino-1-propanesulfonic acid 3-cumylamino-1-propanesulfonic acid 3-[(1R)-1-indanamino]-1-propanesulfonic acid 3-(N-tert-butylcarbamyl)amino-1-propanesulfonic acid 3-(1,2-dimethyl-1-propyl)amino-1-propanesulfonic acid 3-(4-methylcyclohexyl)amino-1-propanesulfonic acid TABLE 4-continued Miscellaneous products of sultone opening reactions
Structure/
Name of Compound 3-(2-methyl-1-butyl)amino-1-propanesulfonic acid 3-pivaloylamino-1-propanesulfonic acid 2-(tert-butyl)amino-1-ethanesulfonic acid 3-(cyclohexanemethyl)amino-1-propanesulfonic acid 3-(1,1-diethylpropargyl)amino-1-propanesulfonic acid 3-(1-ethynylcyclohexyl)amino-1-propanesulfonic acid 3-(2-hydroxy-2-phenyl)amino-1-propanesulfonic acid 3-[(S)-1-(4-methoxyphenyl)ethyl]amino-1-propanesulfonic acid 3-(4-bromophenethyl)amino-1-propanesulfonic acid TABLE 4-continued Miscellaneous products of sultone opening reactions
Structure/
Name of Compound 3-[(S)-1-indanamino]-1-propanesulfonic acid 3-cyclobutylamino-1-propanesulfonic acid 3-(3,3,5-trimethylcyclohexyl)amino]-1-propanesulfonic acid 3-(2-indanamino)-1-propanesulfonic acid 3-(4-biphenylamino)-1-propanesulfonic acid 3-[(1R,2S)-2-hydroxy-1-(methoxymethyl)-2-phenylethyl]amino-1-propanesulfonic acid 3-[(1R,2R,3R,5S)-1,2,6,6-tetramethylbicyclo[3.1.1]hept-3-yl]amino-1-propanesulfonic acid 3-(2-methoxy-1-methylethyl)amino-1-propanesulfonic acid TABLE 4-continued Miscellaneous products of sultone opening reactions
Structure/
Name of Compound 3-[(1R)-2-benzyl-1-hydroxyethyl]amino-1-propanesulfonic acid 3-[(1S)-2-benzyl-1-hydroxyethyl]amino-1-propanesulfonic acid 3-(N-methyl-N-tert-butylamino)-1-propanesulfonic acid 3-[(1R,2S)-2-hydroxyindan-1-amino]-1-propanesulfonic acid 3-[(1S)-1-(hydroxymethyl)-2-methylpropyl]amino-1-propanesulfonic acid 3-[(1S)-1-carbamoyl-2-methylpropyl]amino-1-propanesulfonic acid 4-(tert-butylamino)-1-butanesulfonic acid TABLE 4-continued
Miscellaneous products of sultone opening reactions
Structure/
Name of Compound
4-(tert-butylamino)-2-butanesulfonic acid
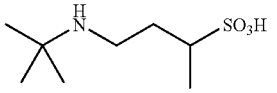
3-(2,2-diphenylethyl)amino-1-propanesulfonic acid
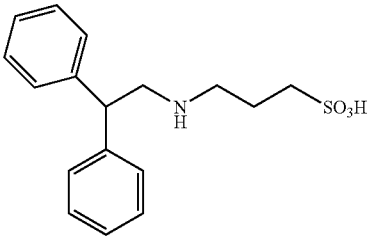
3-(4- mexiletino)-1-propanesulfonic acid
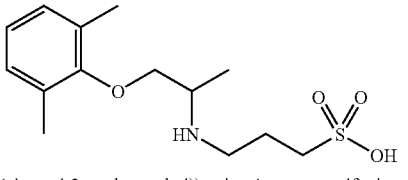
3-(1-benzyl-2-methoxyethyl))amino-1-propanesulfonic acid
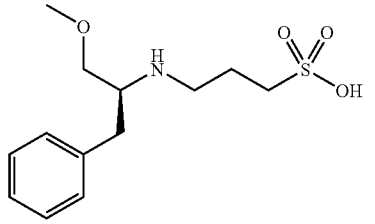
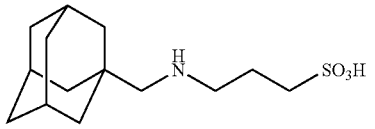
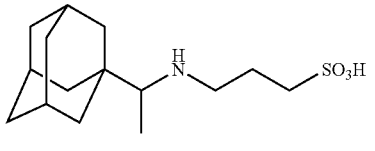
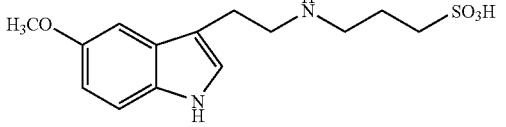
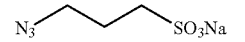
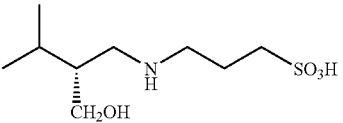

TABLE 4-continued
Miscellaneous products of sultone opening reactions
Structure/
Name of Compound
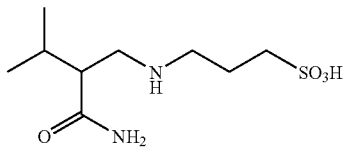
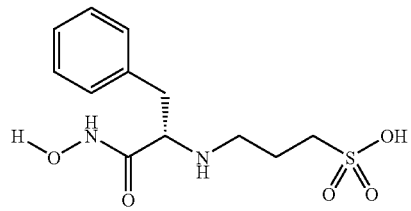
3-[1-(N-hydroxycarbamoyl)-2-phenylethyl)amino-1-propanesulfonic acid
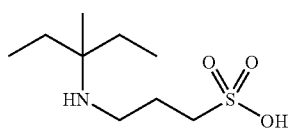
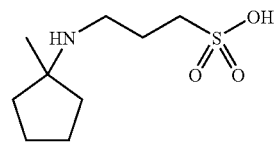
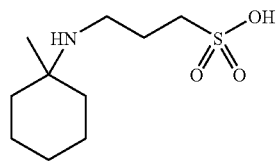
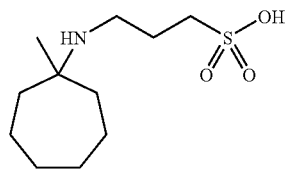
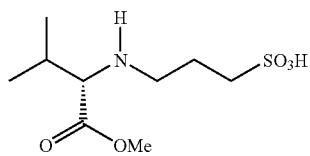

TABLE 4-continued

Miscellaneous products of sultone opening reactions
Structure/
Name of Compound

TABLE 4-continued

Miscellaneous products of sultone opening reactions
Structure/
Name of Compound

TABLE 4-continued
Miscellaneous products of sultone opening reactions
Structure/
Name of Compound
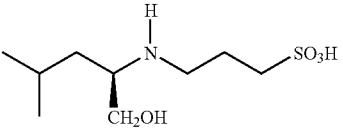
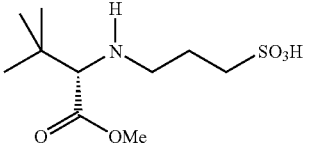
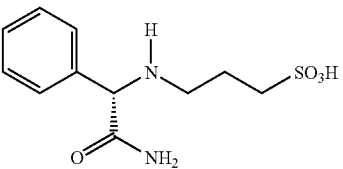
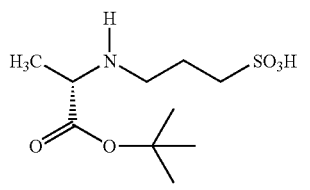
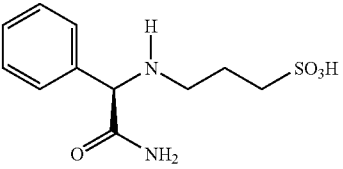
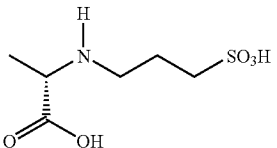
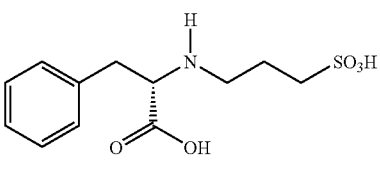
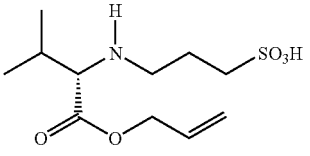
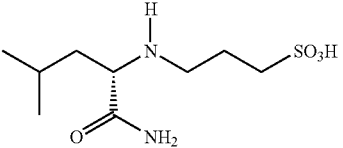

TABLE 4-continued

Miscellaneous products of sultone opening reactions
Structure/
Name of Compound

TABLE 4-continued
Miscellaneous products of sultone opening reactions
Structure/
Name of Compound
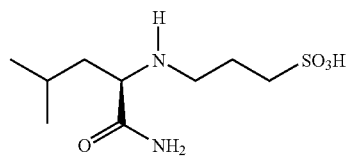
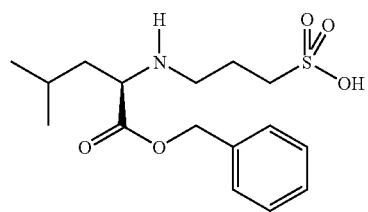
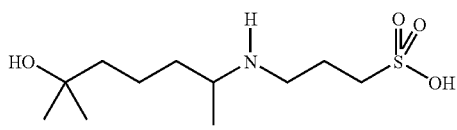
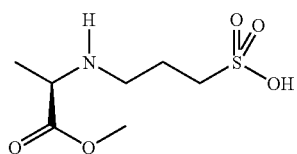
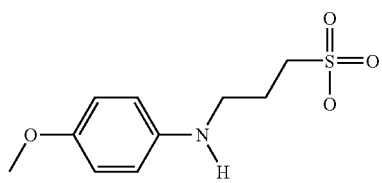
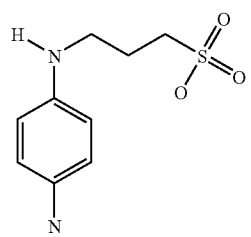
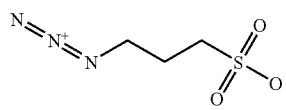
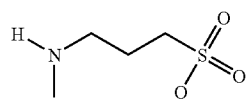

TABLE 4-continued
Miscellaneous products of sultone opening reactions
Structure/
Name of Compound
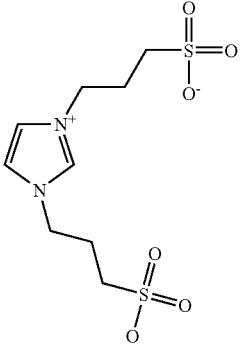
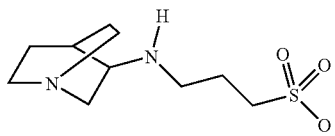
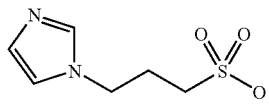
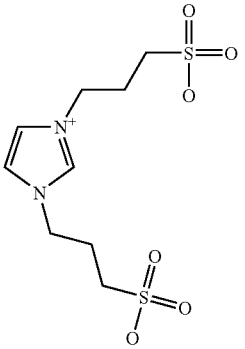
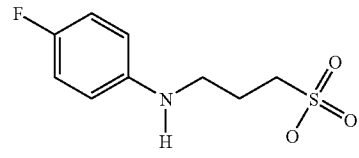
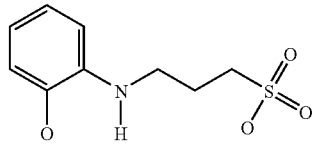
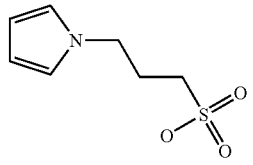

TABLE 4-continued
Miscellaneous products of sultone opening reactions
Structure/
Name of Compound
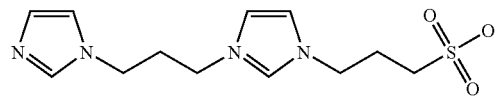
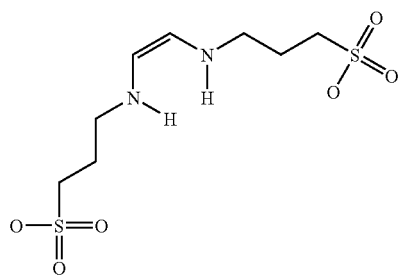
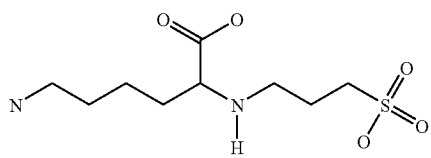
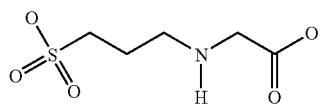
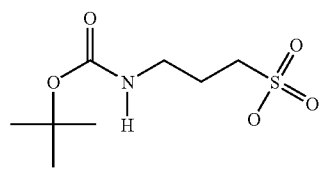
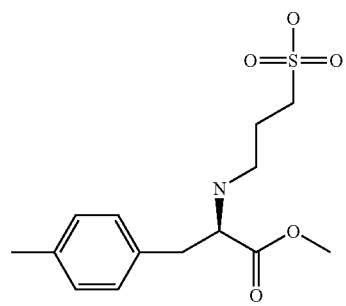

| Structure/ Name of Compound |
|---|
| 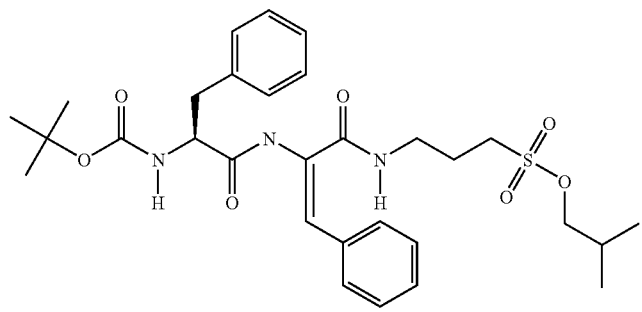 |
| 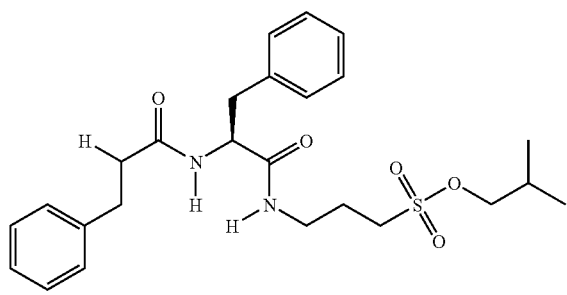 |
| 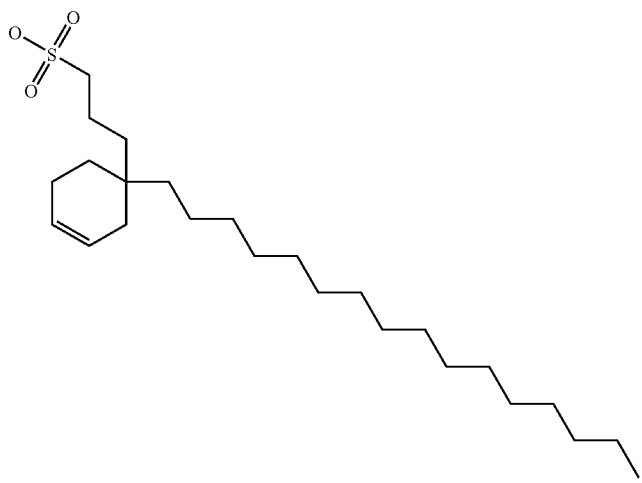 |
| 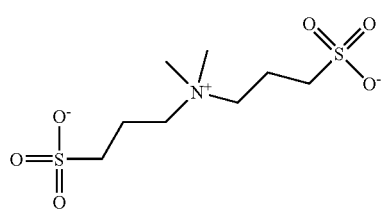 |

-continued
| Structure/<br>Name of Compound |
|---|
| 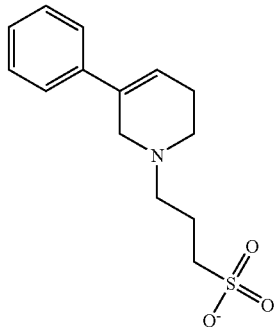 |
| 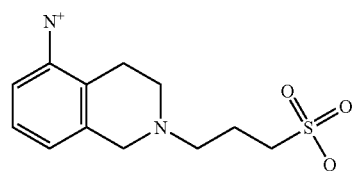 |
| 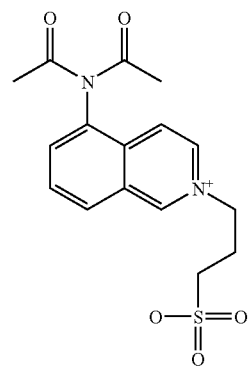 |
| 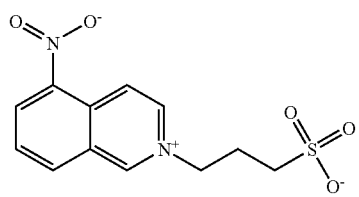 |
| 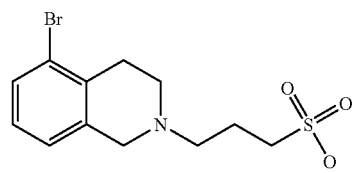 |
| 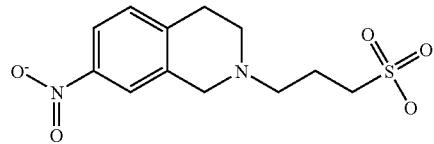 |
| 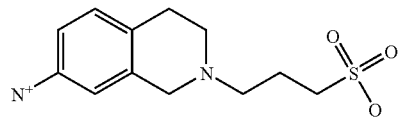 |

-continued
| Structure/Name of Compound |
|---|
| 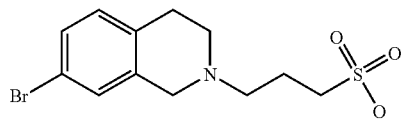 |
| 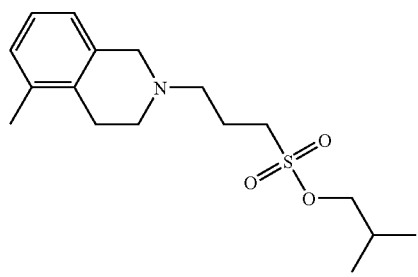 |
| 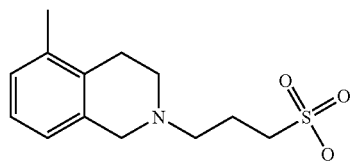 |
| 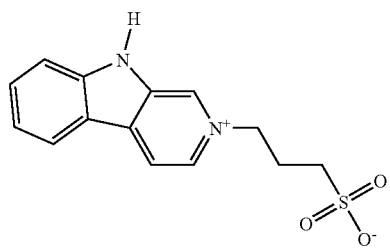 |
| 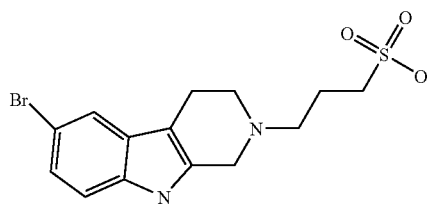 |
| 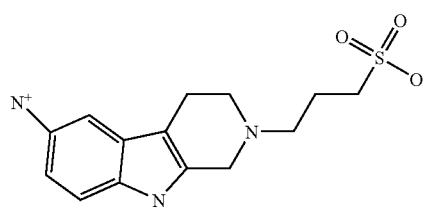 |
| 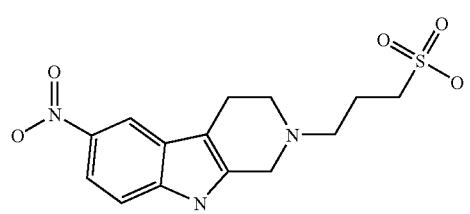 |

-continued
| Structure/<br>Name of Compound |
|---|
| 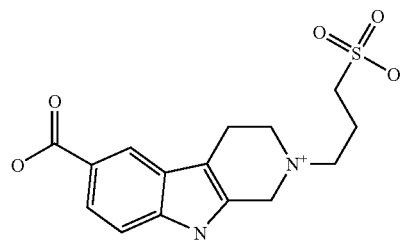 |
| 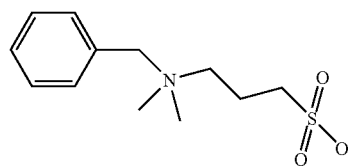 |
| 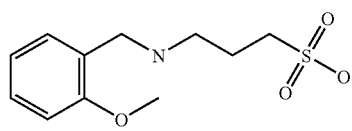 |
| 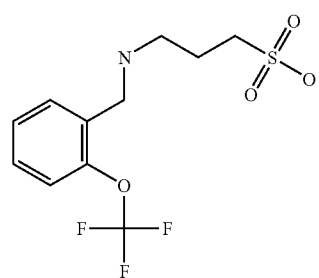 |
| 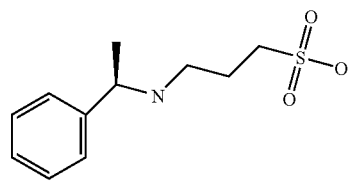 |
| 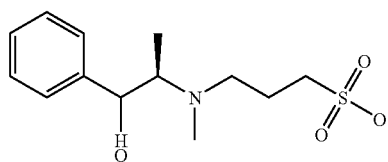 |
| 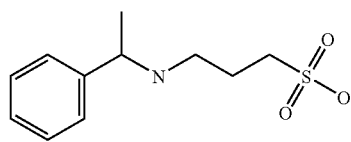 |
| 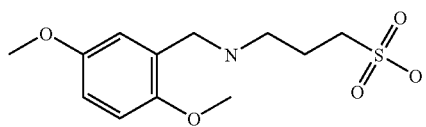 |

-continued
| Structure/ Name of Compound |
|---|
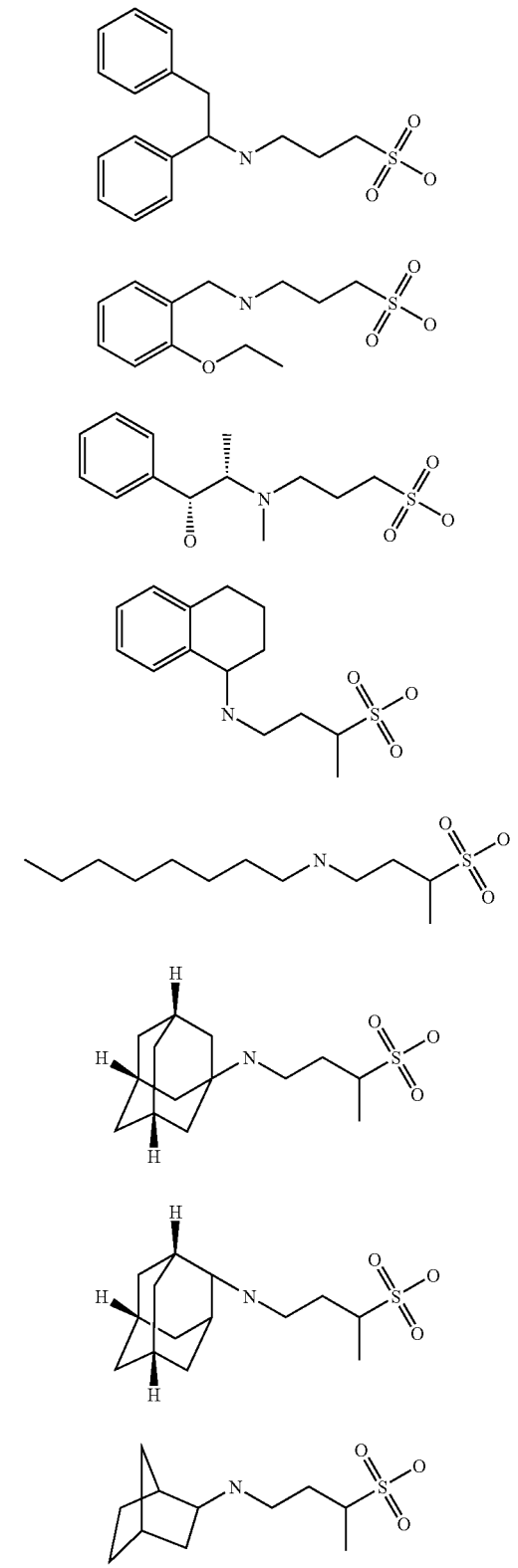

-continued
| Structure/<br>Name of Compound |
|---|
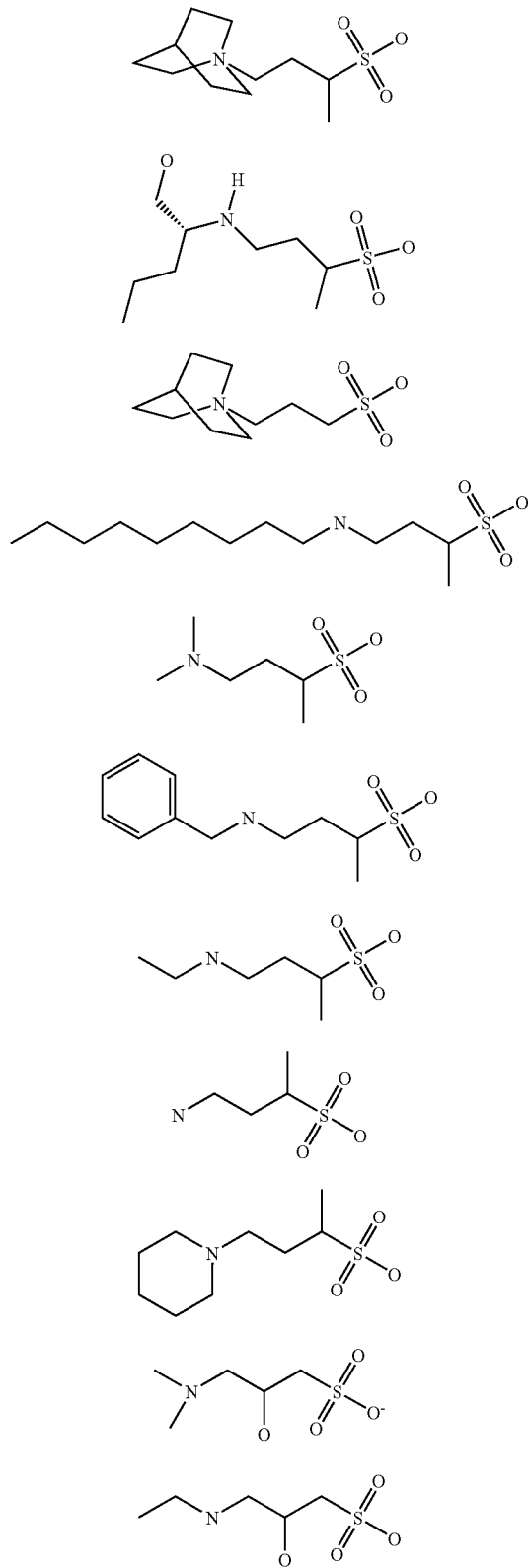

-continued
| Structure/ Name of Compound |
|---|
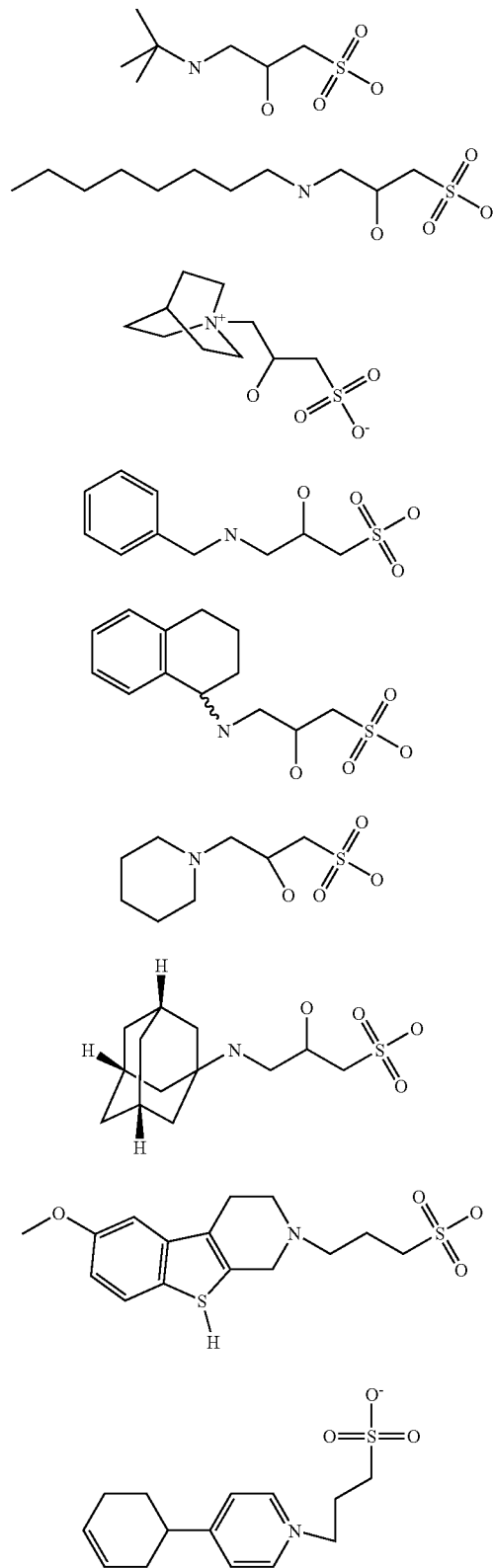

-continued
| Structure/<br>Name of Compound |
|---|
| 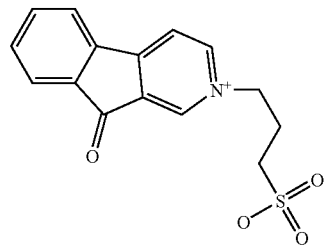 |
| 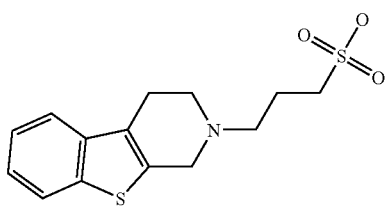 |
| 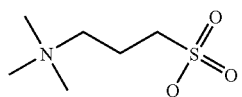 |
| 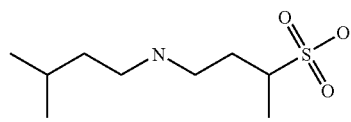 |
| 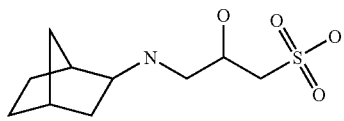 |
| 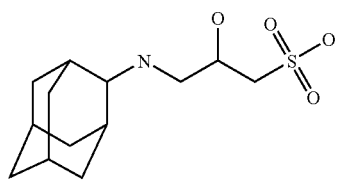 |
| 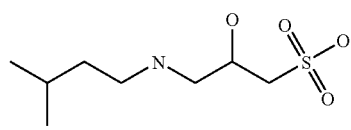 |
| 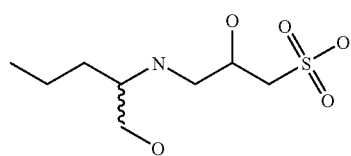 |
| 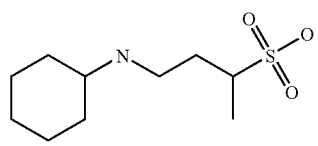 |

-continued
| Structure/<br>Name of Compound |
|---|
| 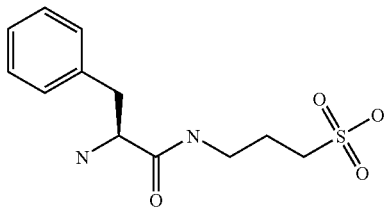 |
| 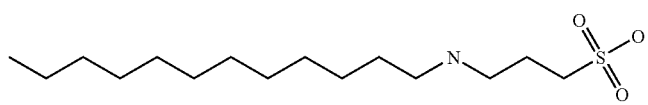 |
| 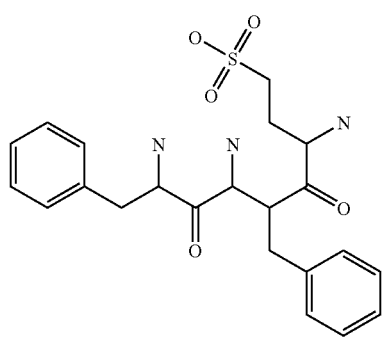 |
| 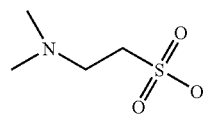 |
| 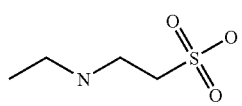 |
| 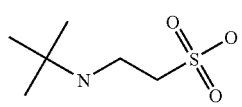 |
| 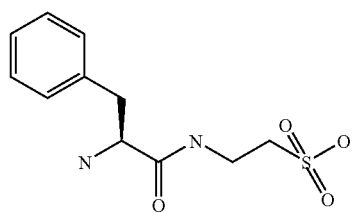 |
| 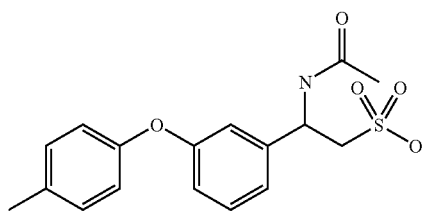 |

-continued
Structure/
Name of Compound
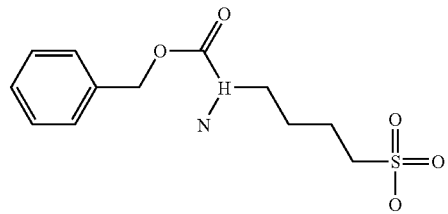
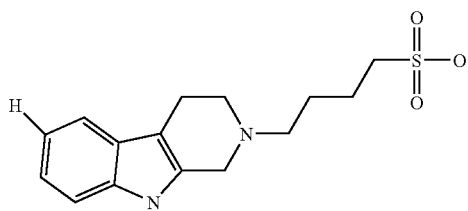
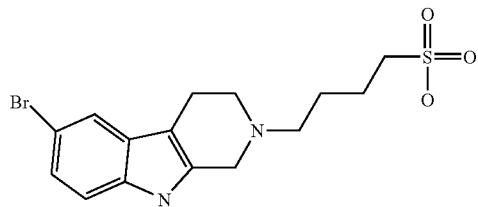
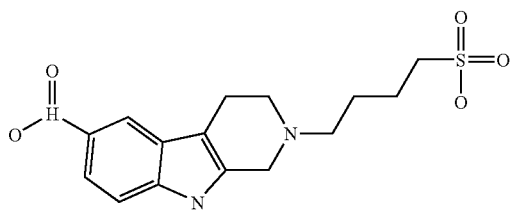
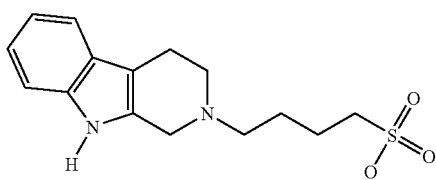
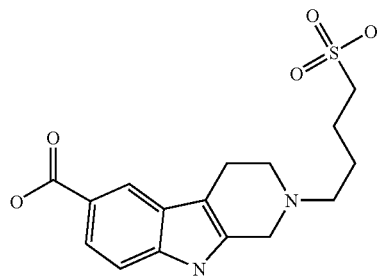
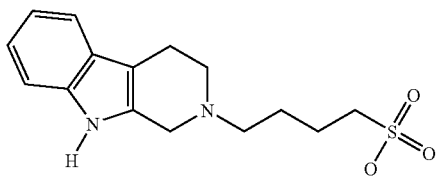

-continued
Structure/
Name of Compound
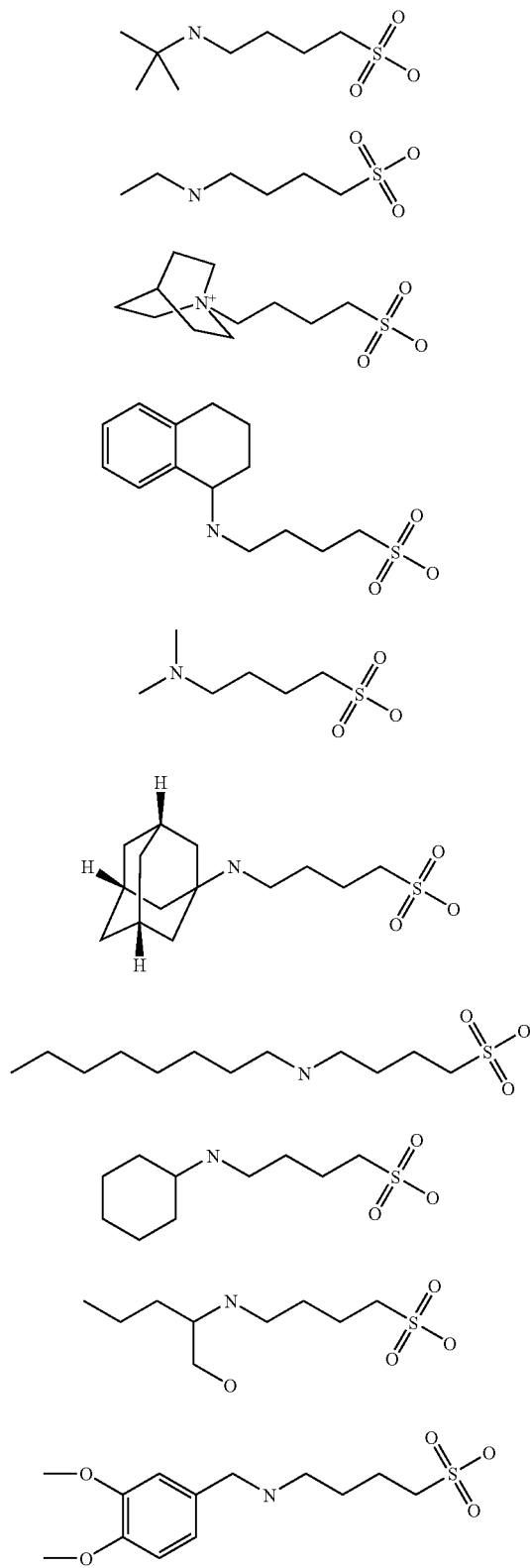

-continued

Structure/
Name of Compound

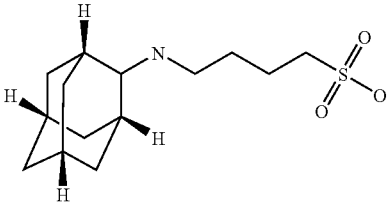

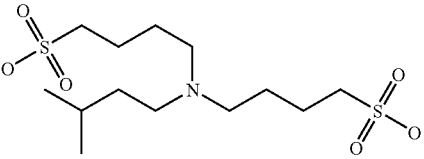

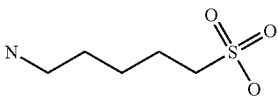

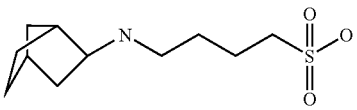

Example 3

Mass Spectroscopy Assay

The ability of a sulfonate derivatized compound of the invention to inhibit an interaction between an amyloidogenic protein and a glycoprotein or proteoglycan constituent of a basement membrane can be used to assess the pharmaceutical applicability of the compounds. In particular, the binding of a sulfonate derivatized compound of the invention to amyloid fibrils may be measured using a mass spectroscopy ("MS") assays as described herein below. The resulting MS assay data provides insight into the ability of compounds to bind to Aβ.

Samples are prepared as aqueous solutions containing 20% ethanol, 200 βM of a test compound and 20 μM of solubilized Aβ40. The pH value of each sample is adjusted to 7.4 (±0.2) by addition of 0.1% aqueous sodium hydroxide. The solutions are then analyzed by electrospray ionization mass spectroscopy using a Waters ZQ 4000 mass spectrometer. Samples are introduced by direct infusion at a flow-rate of 25 μL/min within 2 hours after sample preparation. The source temperature was kept at 70° C. and the cone voltage was 20 V for all the analysis. Data is processed using Masslynx 3.5 software.

The invention claimed is:

1. A method of preparation of a purity-enhanced pharmaceutical drug candidate comprising:
opening a sultone ring with a nucleophile, such that a purity-enhanced sulfonate derivatized pharmaceutical drug candidate is produced,
wherein the sulfonate derivatized pharmaceutical drug candidate is selected from the group consisting of 1,3-propanedisulfonic acid disodium salt, 1,3-propanedisulfonic acid, 1,4-butanedisulfonic acid disodium salt, 3-amino-1-propanesulfonic acid, 3-amino-1-propanesulfonic acid, sodium salt, 3-(dimethylamino)-1-propanesulfonic acid, 3-(1,2,3,6-tetrahydropyridinyl)-1-propanesulfonic acid, 3-(1,2,3,4-tetrahydroisoquinolinyl)-1-propanesulfonic acid, 3-(4-cyano-4-phenylpiperidin-1-yl)-1-propanesulfonic acid, 3-[4-(4-fluorophenyl)-1,2,3,6-tetrahydropyridin-1-yl]-1-propanesulfonic acid, 3-[4-(4-bromophenyl)-4-hydroxypiperidin-1-yl]-1-propanesulfonic acid, 3-[4-(4-chlorophenyl)-4-hydroxypiperidin-1-yl]-1-propanesulfonic acid, 3-(4-acetyl-4-phenylpiperidin-1-yl)-1-propanesulfonic acid, 3-[4-(4-chlorophenyl)-1,2,3,6-tetrahydropyridin-1-yl]-1-propanesulfonic acid, 3-tryptamino-1-propanesulfonic acid, 3-(1,2,3,4-tetrahydro-naphthylamino)-1-propanesulfonic acid, 3-(1-adamantylamino)-1-propanesulfonic acid, 3-(2-norbornylamino)-1-propanesulfonic acid, 3-(2-admantylamino)-1-propanesulfonic acid, 3-(4-(hydroxy-2-pentyl)amino)-1-propanesulfonic acid, 3-nonylamino-1-propanesulfonic acid, and 3-(t-butylamino)-1-propanesulfonic acid.

2. The method of claim 1, wherein the purity-enhanced pharmaceutical drug candidate comprises less than or equal to 5% of by-products.

3. The method of claim 1, wherein the purity-enhanced pharmaceutical drug candidate is significantly free of organic by-products.

4. The method of claim 1, wherein the purity-enhanced pharmaceutical drug candidate is significantly free of nitrogen-containing organic by-products.

5. The method of claim 1, wherein the purity-enhanced pharmaceutical drug candidate is significantly free of inorganic by-products.

6. The method of claim 1, wherein the purity-enhanced pharmaceutical drug candidate comprises a sulfonate derivatized compound that is prepared in large scale.

7. The method of claim 1, wherein the sultone ring opening reaction is represented by:

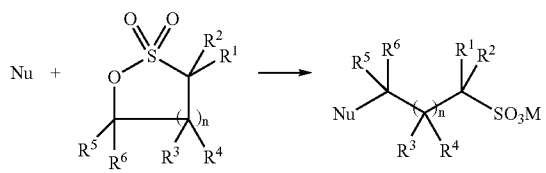

wherein n=1 or 2; Nu is the nucleophile; M is a hydrogen or a salt-forming group; $R^1$, $R^2$, $R^3$, $R^4$, $R^5$, and $R^6$ are independently hydrogen, or a substituted or unsubstituted alkyl group.

8. The method of claim 1, wherein the sultone ring opening reaction is represented by:

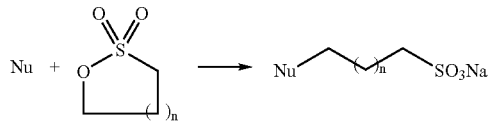

wherein n=1 or 2, and Nu is the nucleophile.

9. The method of claim 1, wherein the pharmaceutical drug candidate is useful in inhibiting amyloid deposition in a subject.

10. The method of claim 1, wherein the pharmaceutical drug candidate is useful in treating amyloidosis in a subject.

11. The method of claim 1, wherein the pharmaceutical drug candidate is useful in treating or preventing an amyloid-related disease in a subject.

12. The method of claim 11, wherein the amyloid related disease is selected from the group consisting of Alzheimer's disease, cerebral amyloid angiopathy, inclusion body myositis, macular degeneration, AA amyloidosis, AL amyloidosis, Down's syndrome, Mild Cognitive Impairment, type II diabetes, and hereditary cerebral hemorrhage.

13. The method of claim 1, wherein the sulfonate derivatized pharmaceutical drug candidate is 1,3-propanedisulfonic acid or a pharmaceutically acceptable salt thereof.

14. The method of claim 1, wherein the sulfonate derivatized pharmaceutical drug candidate is 3-amino-1-propanesulfonic acid or a pharmaceutically acceptable salt thereof.

15. The method of claim 1, wherein the sulfonate derivatized pharmaceutical drug candidate is 3-(dimethylamino)-1-propanesulfonic acid or a pharmaceutically acceptable salt thereof.

16. The method of claim 1, wherein the sulfonate derivatized pharmaceutical drug candidate is 3-(1-adamantylamino)-1-propanesulfonic acid or a pharmaceutically acceptable salt thereof.

17. The method of claim 1, wherein the sulfonate derivatized pharmaceutical drug candidate is 3-(t-butylamino)-1-propanesulfonic acid or a pharmaceutically acceptable salt thereof.

* * * * *